US012807713B2

(12) United States Patent
Cao et al.

(10) Patent No.: US 12,807,713 B2
(45) Date of Patent: Nov. 24, 2026

(54) PROTEIN SPECIFICALLY BINDING TO PD-1 AND PHARMACEUTICAL USE THEREOF

(71) Applicants: JIANGSU HENGRUI PHARMACEUTICALS CO., LTD., Lianyungang (CN); SHANGHAI SHENGDI PHARMACEUTICAL CO., LTD., Shanghai (CN)

(72) Inventors: Zhiliang Cao, Shanghai (CN); Baohui Wang, Shanghai (CN); Yuan Lin, Shanghai (CN); Kan Lin, Shanghai (CN); Cheng Liao, Shanghai (CN)

(73) Assignees: Jiangsu Hengrui Pharmaceuticals Co., Ltd., Lianyungang (CN); Shanghai Shengdi Pharmaceutical Co., Ltd., Shanghai (CN)

( * ) Notice: Subject to any disclaimer, the term of this patent is extended or adjusted under 35 U.S.C. 154(b) by 428 days.

(21) Appl. No.: 18/691,870

(22) PCT Filed: Sep. 15, 2022

(86) PCT No.: PCT/CN2022/118979

§ 371 (c)(1),
(2) Date: Mar. 13, 2024

(87) PCT Pub. No.: WO2023/040945

PCT Pub. Date: Mar. 23, 2023

(65) Prior Publication Data

US 2024/0376204 A1 Nov. 14, 2024

(30) Foreign Application Priority Data

Sep. 15, 2021 (CN) ......................... 202111078222.1

(51) Int. Cl.

| | |
|---|---|
| ***C07K 16/28*** | (2006.01) |
| ***A61P 35/00*** | (2006.01) |
| ***C07K 16/46*** | (2006.01) |
| *A61K 39/00* | (2006.01) |

(52) U.S. Cl.

CPC .......... *C07K 16/2818* (2013.01); *A61P 35/00* (2018.01); *C07K 16/468* (2013.01); *A61K 2039/505* (2013.01); *C07K 2317/24* (2013.01); *C07K 2317/31* (2013.01); *C07K 2317/522* (2013.01); *C07K 2317/565* (2013.01)

(58) Field of Classification Search

None

See application file for complete search history.

(56) References Cited

U.S. PATENT DOCUMENTS 11,225,523 B2 * 1/2022 Liang ................... A61K 39/395

FOREIGN PATENT DOCUMENTS

| | | | |
|---|---|---|---|
| CN | 112794909 | A | 5/2021 |
| WO | 2017079115 | A1 | 5/2017 |
| WO | 2018222711 | A2 | 12/2018 |
| WO | 2019232484 | A1 | 12/2019 |
| WO | 2021154761 | A1 | 8/2021 |

OTHER PUBLICATIONS

Lieping Chen et al., Molecular mechanisms of T cell co-stimulation and co-inhibition, Nature Reviews Immunology, Mar. 2013, vol. 13, pp. 227-242 (30 pages). doi.org/10.1038/nri3405.

H. Dong et al., B7-H1, A third member of the B7 family, co-stimulates T-cell proliferation and interleukin 10 secretion, Natural Medicinee, Dec. 1999, vol. 5, No. 12 (1 page). doi: 10.1038/70932. PMID: 10581077.

Ludovic Martinet et al., DNAM-1 expression marks an alternative program of NK cell maturation, Cell Reports, Apr. 7, 2015, vol. 11, No. 1, pp. 85-97 (14 pages). doi: 10.1016/j.celrep.2015.03.006.

Alice L. Hung et al., TIGIT and PD-1 dual checkpoint blockade enhances antitumor immunity and survival in GBM, Oncoimmunology, May 24, 2018; vol. 7, No. 8 (26 pages). doi: 10.1080/2162402X.2018.1466769.

Ailin Lepletier et al., Tumor CD155 Expression Is Associated with Resistance to Anti-PD1 Immunotherapy in Metastatic Melanoma, Clinical Cancer Research, Jul. 15, 2020, vol. 26, No. 14, pp. 3671-3681 (11 pages). doi: 10.1158/1078-0432.CCR-19-3925.

Ryan Sullivan et al., Abstract CT031: COM701 demonstrates preliminary antitumor activity as monotherapy and in combination with nivolumab in patients with advanced solid tumors, Cancer Research, Oral Presentations—Proffered Abstracts, Aug. 15, 2020 (5 pages). doi.org/10.1158/1538-7445.AM2020-CT031.

James L. Riley, PD-1 signaling in primary T cells, Immunological Reviews, May 2009, vol. 229, No. 1, pp. 114-125 (19 pages). doi: 10.1111/j.1600-065X.2009.00767.x.

Sarah Whelan et al., PVRIG and PVRL2 Are Induced in Cancer and Inhibit CD8+ T-cell Function, Cancer Immunology Research, Feb. 2019, vol. 7, No. 2, pp. 257-268 (24 pages). doi: 10.1158/2326-6066.CIR-18-0442.

Yuwen Zhu, Identification of CD112R as a novel checkpoint for human T cells, Journal of Experimental Medicine, Feb. 8, 2016, vol. 213, No. 2, pp. 167-176 (10 pages).

* cited by examiner

*Primary Examiner* — Meera Natarajan

(74) *Attorney, Agent, or Firm* — Morgan, Lewis & Bockius LLP

(57) ABSTRACT

The present disclosure relates to a protein specifically binding to PD-1 and a pharmaceutical use thereof. Specifically, the present disclosure provides a protein specifically binding to PD-1, a protein specifically binding to PD-1/PVRIG/TIGIT, and a use thereof in the treatment of a disease (such as cancer).

24 Claims, 14 Drawing Sheets

Specification includes a Sequence Listing.

PROTEIN SPECIFICALLY BINDING TO PD-1 AND PHARMACEUTICAL USE THEREOF

CROSS-REFERENCE TO RELATED APPLICATIONS

The present application is a national stage application of International Patent Application No. PCT/CN2022/118979, filed Sep. 15, 2022, which claims the benefit of and priority to Chinese Patent Application No. 202111078222.1, filed on Sep. 15, 2021, which is incorporated herein by reference in its entirety.

SEQUENCE LISTING

The instant application contains a Sequence Listing which has been submitted electronically in XML format and is hereby incorporated by reference in its entirety. Said XML copy, created on Mar. 13, 2024, is named "722116CPUS_126268-5078-US_Sequence_Listing.xml" and is approximately 108,632 bytes in size.

TECHNICAL FIELD

The present disclosure relates to the field of biopharmaceutics and particularly to a protein that specifically binds to PD-1, a protein that specifically binds to PD-1/PVRIG/TIGIT, a method for treating cancer using same, and pharmaceutical use thereof.

BACKGROUND

Immunotherapy is a popular topic in the area of cancer treatment. Anti-PD-1 antibodies, as representative immunotherapy drugs, have been clinically shown to be highly effective and highly safe.

PD-1 (programmed cell death-1), an immunosuppressive receptor, belongs to the CD28 receptor family (Riley et al., 2009, Immunol. Rev. 29:114-25). This family also includes CD28, CTLA-4, ICOS, PD-1, and BTLA. PD-1 is a type I transmembrane protein and is structurally similar to CTLA-4, but PD-1 lacks the MYPPPY sequence that binds to B7-1 and B7-2. PD-1 is expressed mainly by activated B cells, T cells, and bone marrow cells (Chen et al., 2013, Nat. Rev. Immunol. 13:227-42).

There are two cell surface glycoprotein ligands for PD-1, which are PD ligand 1 (PD-L1, also known as CD274, B7-H1) and PD ligand 2 (PD-L2, also known as B7-DC). Neither PD-L1 nor PD-L2 binds to other members of the CD28 receptor family. PD-L1 is widely expressed by lymphocytes (e.g., $CD4^+$ T cells, $CD8^+$ T cells, and macrophages), peripheral tissues, various tumor cells, virus-infected cells, etc. PD-L2 is expressed mainly by activated dendritic cells and macrophages (Dong et al., 1999, Nat. Med. 5:1365-9). After binding to its ligand PD-L1 or PD-L2, PD-1 down-regulates T cell function, including reducing T cell activation, differentiation, proliferation, cytokine secretion, etc.

PVRIG (poliovirus receptor-related Ig domain containing protein), also known as CD112R, belongs to the B7/CD28 superfamily as TIGIT (T cell immunoglobulin and ITIM domain), CD96, and CD226 do and plays an important role in the immune system. When PVRIG's ligand PVRL2 (also known as CD112) binds to PVRIG, it activates the ITIM domain in the intracellular region of PVRIG, causing PVRIG to play an immunosuppressive role. PVRIG is expressed mainly on the surfaces of $CD4^+$ T cells, $CD8^+$ T cells, and NK cells. PVRIG and its ligand PVRL2 are highly expressed in many solid tumors, including lung cancer, breast cancer, ovarian cancer, renal cancer, gastric cancer, endometrial cancer, head and neck cancer, and the like. The expression of PVRIG in these cancers is highly correlated with TIGIT and PD-1. Similar to PD-1 and TIGIT, PVRIG-positive T cells are also Eomes-positive and Tbet-negative, indicating that PVRIG is associated with T cell depletion. Thus, PVRIG may represent a new immune checkpoint other than PD-1 and TIGIT and plays the role of redundancy. In vitro cell experiments and mouse model experiments show that knocking out or inhibiting mouse PVRIG can effectively inhibit cancer growth and act synergistically with PD-1 and TIGIT inhibitors. TIGIT is highly expressed on lymphocytes, including tumor-infiltrating lymphocytes (TILs) and Tregs that infiltrate different types of cancer. TIGIT binding to its cognate ligand PVR (also known as CD155) has been shown to directly suppress the cytotoxicity of NK cells through its cytoplasmic ITIM domain. PVR is also widely expressed in cancer, suggesting that the TIGIT-PVR signaling axis may be a major immune escape mechanism in cancer. The inhibiting receptors TIGIT and PVRIG bind to the ligands CD155 and CD112 as the activating receptor DNAM-1 does, but the affinities of the inhibiting receptors are higher (Y. Zhu et al., 2016, J Exp Med. 213:167-176). In patients with tumors, DNAM-1 expression is down-regulated in isolated NK cells, making NK cells more susceptible to inhibition by TIGIT or PVRIG. Blocking the binding of TIGIT and PVRIG can activate NK cells' cell killing function (L. Martinet et al., 2015, Cell Reports. 11:85-97).

PD-1/PD-L1 antibodies are currently the most clinically successful immune checkpoint inhibitor mAbs; however, up-regulation of the expression of other immune checkpoints on the surfaces of T cells can limit their efficacy. TIGIT and PVRIG also regulate NK cell activity in addition to T cell function, suggesting a possible synergy with the function of PD-1/PD-L1 in NK cells. There are reports that the high expression of CD155 and CD112, the ligands for TIGIT and PVRIG, in lung cancer, ovarian cancer, colorectal cancer, and melanoma is significantly correlated with poor prognoses following PD-1/PD-L1 treatment. For example, patients with high CD155 expression respond poorly to anti-PD-1 antibodies, whereas patients with low CD155 expression respond well to PD-1 (S. Whelan et al., 2019, Cancer Immunol Res. 7:257-268; A. Lepletier et al., 2020, Clin Cancer Res. 26:3671-3681).

There has not been any PVRIG antibody or anti-PVRIG/TIGIT bispecific antibody drug on the market. COM701 of Compugen is the world's first anti-PVRIG humanized antibody approved by the FDA to enter clinical trials, and it is currently in phase I clinical trials for treating cancer. Surface Oncology is also developing an anti-PVRIG antibody, which is SRF-813. Anti-TIGIT antibodies include tiragolumab of Genentech, BMS-986207 developed by Ono Pharmaceutical in cooperation with BMS, MK-7684 of MSD, EOS-884448 of iTeos Therapeutics, and AB-154 of Arcus Biosciences, all of which are in phase II clinical trials.

Therefore, the present disclosure provides an anti-PD-1 antibody of a new structure and a related anti-PD-1/PVRIG/TIGIT trispecific antibody, which are expected to enhance T cell and NK cell activation, overcome the drug resistance of PD-1/PD-L1, expand the population of responsive patients, and thereby improve the effect of cancer immunotherapy. Moreover, the anti-PD-1/PVRIG/TIGIT trispecific antibody can bind to multiple immune checkpoints on the same cell surface simultaneously and has a potential avidity effect, and therefore has the potential to provide better clinical efficacy than the existing PD-1, TIGIT, and PVRIG antibody drugs or their combinations.

SUMMARY

The present disclosure provides a PD-1-binding protein, PD-1/PVRIG/TIGIT-binding protein, PD-1/PVRIG-binding protein, or PD-1/TIGIT-binding protein, a coding nucleic acid therefor, a vector thereof, a host cell thereof, a pharmaceutical composition thereof, a method for treating or preventing cancer using same, and related pharmaceutical use thereof.

PD-1-Binding Protein

The present disclosure provides a PD-1-binding protein, comprising an immunoglobulin single variable domain, wherein the immunoglobulin single variable domain comprises:

- a CDR1, a CDR2, and a CDR3 from the amino acid sequence set forth in any of SEQ ID NOs: 3, 13-15, and 17-35, or
- a CDR1, a CDR2, and a CDR3 from the amino acid sequence set forth in any of SEQ ID NOs: 2 and 16;
- the CDR1, CDR2, and CDR3 are defined according to the Kabat, IMGT, Chothia, AbM, or Contact numbering scheme. The immunoglobulin single variable structure specifically binds to PD-1 antigen or a fragment thereof.

In some embodiments, the PD-1-binding protein comprises at least one immunoglobulin single variable structure.

In some embodiments, provided is a PD-1-binding protein, comprising any of the CDR1, CDR2, and CDR3 described above, or any combination thereof.

In some embodiments, provided is a PD-1-binding protein; according to the Kabat numbering scheme, the amino acid sequences of the CDR1, CDR2, and CDR3 of the immunoglobulin single variable domain are set forth in SEQ ID NOs: 7, 36, and 37, respectively, or SEQ ID NOs: 4, 5, and 6, respectively.

In some embodiments, of the immunoglobulin single variable domain in the aforementioned PD-1-binding protein, the amino acid sequence of the CDR1 is set forth in SEQ ID NO: 7, the amino acid sequence of the CDR2 is set forth in any of SEQ ID NOs: 8, 38-40, and 101, and the amino acid sequence of the CDR3 is set forth in any of SEQ ID NOs: 9, 41, and 42.

In some embodiments, the amino acid sequences of the CDR1, CDR2, and CDR3 of the immunoglobulin single variable domain in the aforementioned PD-1-binding protein are set forth in SEQ ID NOs: 7, 38, and 41, respectively.

In some embodiments, the immunoglobulin single variable domain in the aforementioned PD-1-binding protein is modified by humanization, affinity maturation, T cell epitope removal, reduction of antibody deamidation, and/or reduction of antibody isomerization. In some embodiments, the immunoglobulin single variable domain is obtained by affinity maturation and has one or more changes in one or more CDRs that result in an increase in the affinity for PD-1 as compared to the parent immunoglobulin single variable domain.

In some specific embodiments, the humanization modification process uses the heavy chain framework region of the human germline template, IGHV3-23*01 or IGHV3-23*04.

In some embodiments, the amino acid sequence of the immunoglobulin single variable domain in the aforementioned PD-1-binding protein is set forth in any of SEQ ID NOs: 3, 13-15, and 17-35, or any of SEQ ID NOs: 2 and 16, or has at least 80% sequence identity to any of the aforementioned sequences.

In the present disclosure, "at least 90% (sequence) identity" encompasses at least 90%, at least 91%, at least 92%, at least 93%, at least 94%, at least 95%, at least 96%, at least 97%, at least 98%, at least 99%, or 100% (sequence) identity; "at least 80% (sequence) identity" encompasses at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% (sequence) identity.

In some embodiments, the aforementioned PD-1-binding protein comprises or is an antibody that specifically binds to PD-1 or a fragment thereof, or an antigen-binding fragment thereof. The antibody or the antigen-binding fragment thereof is, for example, a camelid antibody, a chimeric antibody, a humanized antibody, a fully human antibody, or an antigen-binding fragment thereof. The antibody or the antigen-binding fragment thereof is, for example, a recombinant antibody or a fragment thereof.

In some specific embodiments, the antigen-binding fragment is a linear antibody, a single-chain antibody, a nanobody, a peptibody, a domain antibody, or a multispecific antibody (a bispecific antibody, a diabody, a triabody, a tetrabody, a tandem di-scFv, or a tandem tri-scFv).

In some embodiments, the immunoglobulin single variable domain in the aforementioned PD-1-binding protein is a VHH.

In some embodiments, the present disclosure provides a PD-1-binding protein, comprising one or more (e.g., 2, 3, 4, 5, or 6) aforementioned immunoglobulin single variable domains, and the immunoglobulin single variable domains may be identical or different and may form a dimeric or multimeric molecule.

In some embodiments, the aforementioned PD-1-binding protein further comprises a human immunoglobulin Fc region; for example, the Fc region is the Fc region of human IgG1, IgG2, or IgG4. The Fc region may have a mutation; exemplary mutations are selected from any of the following or a combination thereof:

- L234A/L235A on IgG1;
- S267E/L328F on IgG1;
- L234F/L235E/D265A on IgG1;
- L234A/L235A/G237A/P238S/H268A/A330S/P331S on IgG1;
- K214T/E233P/L234V/L235A/G236 deletion/A327G/P331A/D365E/L358M on IgG1;
- V234A/G237A on IgG2;
- H268Q/V309L/A330S/P331S on IgG2;
- V234A/G237A/P238S/H268A/V309L/A330S/P331S on IgG2;
- F234A/L235A on IgG4;
- S228P/F234A/L235A on IgG4;
- S228P/F234A/L235A/G237A/P238S on IgG4;
- S228P/F234A/L235A/G236 deletion/G237A/P238S on IgG4; and
- N297A on IgG1, IgG2, IgG3, or IgG4.

A hybrid IgG2/4Fc domain may also be used, e.g., an Fc with residues 117-260 from IgG2 and residues 261-447 from IgG4. In some specific embodiments, the Fc region of human IgG4 has mutations 228P, 234A, 235A, and/or 447A.

In the context of the mutations contained in the Fc region herein, "/" represents "and"; for example, "F234A/L235A" represents "F234A and L235A"; that is, the Fc comprises the mutations F234A and L235A; the amino acid positions of the mutations are numbered according to the EU numbering scheme.

In some embodiments, the Fc region contained in the aforementioned PD-1-binding protein enables the binding protein to form a dimeric molecule to extend the in vivo half-life of the binding protein.

In some embodiments, in the aforementioned PD-1-binding protein, the immunoglobulin single variable domain is linked to the Fc region, either directly or by a linker. The linker may be a non-functional amino acid sequence of 1-20 or more amino acids without a secondary or higher structure. For example, the linker is a flexible linker, for example, $G_4S$, GS, GAP, $(G_4S)_2$, $(G_4S)_3$, $(G_4S)_4$, $(G_4S)_5$, or ASGS.

In some embodiments, the PD-1-binding protein of the present disclosure is an anti-PD-1 antibody or an antigen-binding fragment thereof, or a conjugate or fusion protein comprising the antibody or antigen-binding fragment.

In some embodiments, the aforementioned PD-1-binding protein has an activity selected from at least one of the following:

(a) binding to human PD-1 or an epitope thereof with a $K_D$ value of $\leq 10^{-7}$
(b) inhibiting the binding of PD-1 to PD-L1;
(c) inhibiting the binding of PD-1 to PD-L2;
(d) inducing $CD4^+$ T cells to secrete IFN-γ;
(e) enhancing PBMC activation;
(f) enhancing T cell activation; and
(g) inhibiting tumor growth.

In some embodiments, the aforementioned PD-1-binding protein of the present disclosure may bind to PD-1 with a $K_D$ value of $\leq 1\times10^{-7}$ M, e.g., $\leq 1\times10^{-8}$ M, or $\leq 1\times10^{-9}$ M, or $\leq 1\times10^{-10}$ M.

In some embodiments, the PD-1-binding protein of the present disclosure is capable of specifically binding to human PD-1 and blocking the interaction between PD-1 and PD-L1, and/or blocking the interaction of PD-1 between PD-L2.

In some embodiments, the aforementioned PD-1-binding protein of the present disclosure is capable of inhibiting tumor growth by at least about 10%, e.g., at least about 20%, about 30%, about 40%, about 50%, about 60%, about 70%, or about 80%.

In some embodiments, the aforementioned PD-1-binding protein of the present disclosure encompasses a variant, wherein the variant has one or more (e.g., 1, 2, 3, 4, 5, 6, 7, 8, 9, or 10) amino acid mutations as compared to any of SEQ ID NOs: 2-3 and 13-35; the amino acid mutations may be conservative replacements, substitutions, or modifications, and/or deletions or additions that do not affect function; the amino acid mutations may occur in the CDRs and/or FRs.

In some embodiments, provided is an anti-PD-1 antibody or an antigen-binding fragment thereof that binds to or competes for binding to the same epitope with the immunoglobulin single variable domain in the aforementioned PD-1-binding protein of the present disclosure.

In some embodiments, provided is an anti-PD-1 antibody or an antigen-binding fragment thereof that blocks the binding of the immunoglobulin single variable domain in the aforementioned PD-1-binding protein of the present disclosure to PD-1 (e.g., human PD-1).

In some embodiments, provided is an anti-PD-1 antibody or an antigen-binding fragment thereof whose binding to PD-1 (e.g., human PD-1) is blocked by the immunoglobulin single variable domain in the aforementioned PD-1-binding protein of the present disclosure.

In some embodiments, the aforementioned PD-1-binding protein of the present disclosure reduces the binding of PD-1 to PD-L1 and/or PD-L2 by at least 60%, at least 70%, at least 80%, at least 90%, at least 95%, or at least 98% or more.

In some embodiments, provided is a protein or molecule, comprising any one or more (e.g., 1, 2, 3, 4, 5, 6, 7, 8, 9, or 10) of the immunoglobulin single variable domains in the aforementioned PD-1-binding proteins of the present disclosure, and the immunoglobulin single variable domains are identical or different. For example, the protein or molecule is a conjugate, and the conjugate may, for example, comprise any detectable label.

PD-1/PVRIG/TIGIT-Binding Protein

The present disclosure provides a PD-1/PVRIG/TIGIT-binding protein, comprising a first antigen-binding domain that specifically binds to PD-1, a second antigen-binding domain that specifically binds to PVRIG, and a third antigen-binding domain that specifically binds to TIGIT, which is capable of specifically binding to PD-1, PVRIG, and TIGIT simultaneously or separately.

In some embodiments, the aforementioned PD-1/PVRIG/TIGIT-binding protein comprises or is an anti-PD-1/PVRIG/TIGIT trispecific antibody.

In some embodiments, each of the antigen-binding domains in the aforementioned PD-1/PVRIG/TIGIT-binding protein is selected from the group consisting of a Fab, an Fv, an sFv, a Fab', a $F(ab')_2$, a linear antibody, a single-chain antibody, an scFv, an sdAb, an sdFv, a nanobody, a peptibody, a domain antibody, and any combination thereof. In a specific embodiment, the first antigen-binding domain that specifically binds to PD-1 comprises or is a VHH, the second antigen-binding domain that specifically binds to PVRIG comprises or is a VHH, and the third antigen-binding domain that specifically binds to TIGIT is a Fab or $F(ab')_2$.

In some embodiments, the aforementioned PD-1/PVRIG/TIGIT-binding protein is modified by humanization, affinity maturation, T cell epitope removal, reduction of antibody deamidation, and/or reduction of antibody isomerization.

In some embodiments, the aforementioned PD-1/PVRIG/TIGIT-binding protein is a recombinant antibody, a camelid antibody, a chimeric antibody, a humanized antibody, a fully human antibody, or an antigen-binding fragment thereof.

In some embodiments, in the aforementioned PD-1/PVRIG/TIGIT-binding protein, the first antigen-binding domain that specifically binds to PD-1 comprises an (at least one) immunoglobulin single variable domain, and the immunoglobulin single variable domain comprises:

a CDR1, a CDR2, and a CDR3 from the amino acid sequence set forth in any of SEQ ID NOs: 3, 13-15, and 17-35, or a CDR1, a CDR2, and a CDR3 from the amino acid sequence set forth in any of SEQ ID NOs: 2 and 16;

the CDR1, CDR2, and CDR3 are defined according to the Kabat, IMGT, Chothia, AbM, or Contact numbering scheme.

In some embodiments, according to the Kabat numbering scheme, the amino acid sequences of the CDR1, CDR2, and CDR3 of the immunoglobulin single variable domain are set forth in:

SEQ ID NOs: 7, 36, and 37, respectively, or

SEQ ID NOs: 4, 5, and 6, respectively.

In some specific embodiments, of the immunoglobulin single variable domain, the amino acid sequence of the CDR1 is set forth in SEQ ID NO: 7, the amino acid sequence of the CDR2 is set forth in any of SEQ ID NOs: 8, 38-40, and 101, and the amino acid sequence of the CDR3 is set forth in any of SEQ ID NOs: 9, 41, and 42.

In some specific embodiments, the amino acid sequences of the CDR1, CDR2, and CDR3 of the immunoglobulin single variable domain are set forth in SEQ ID NOs: 7, 38, and 41, respectively.

In some embodiments, in the aforementioned PD-1/PVRIG/TIGIT-binding protein, the second antigen-binding domain that specifically binds to PVRIG comprises an (at least one) immunoglobulin single variable domain, and the immunoglobulin single variable domain comprises:

a CDR1, a CDR2, and a CDR3 from the amino acid sequence set forth in any of SEQ ID NOs: 45, 62-66, and 95-96, or a CDR1, a CDR2, and a CDR3 from the amino acid sequence set forth in any of SEQ ID NOs: 44 and 57-61.

In some specific embodiments, according to the Kabat numbering scheme, the amino acid sequences of the CDR1, CDR2, and CDR3 of the immunoglobulin single variable domain are set forth in:

SEQ ID NOs: 49, 50, and 51, respectively, or

SEQ ID NOs: 46, 47, and 48 or 99, respectively.

In some embodiments, in the aforementioned PD-1/PVRIG/TIGIT-binding protein, the third antigen-binding domain that specifically binds to TIGIT comprises a heavy chain variable region (VH) and a light chain variable region (VL), wherein:

the heavy chain variable region comprises a HCDR1, a HCDR2, and a HCDR3, the amino acid sequences of which are set forth in SEQ ID NOs: 73, 74, and 75, respectively; the light chain variable region comprises a LCDR1, a LCDR2, and a LCDR3, the amino acid sequences of which are set forth in SEQ ID NOs: 76, 77, and 78, respectively.

In some embodiments, in the aforementioned PD-1/PVRIG/TIGIT-binding protein, the first antigen-binding domain that specifically binds to PD-1 comprises:

the amino acid sequence set forth in any of SEQ ID NOs: 3, 13-15, and 17-35 or an amino acid sequence having at least 80% or at least 90% sequence identity thereto; or the amino acid sequence set forth in any of SEQ ID NOs: 2 and 16 or an amino acid sequence having at least 80% or at least 90% sequence identity thereto.

In some embodiments, in the aforementioned PD-1/PVRIG/TIGIT-binding protein, the second antigen-binding domain that specifically binds to PVRIG comprises: the amino acid sequence set forth in any of SEQ ID NOs: 45, 62-66, and 95-96 or an amino acid sequence having at least 80% or at least 90% sequence identity thereto; or the amino acid sequence set forth in any of SEQ ID NOs: 44 and 57-61 or an amino acid sequence having at least 80% or at least 90% sequence identity thereto.

In some embodiments, in the aforementioned PD-1/PVRIG/TIGIT-binding protein, the third antigen-binding domain that specifically binds to TIGIT comprises a heavy chain variable region (VH) and a light chain variable region (VL), wherein: the heavy chain variable region comprises the amino acid sequence set forth in any of SEQ ID NOs: 79-81 or an amino acid sequence having at least 80% or at least 90% identity thereto; the light chain variable region comprises the amino acid sequence set forth in SEQ ID NO: 82 or 83 or an amino acid sequence having at least 80% or at least 90% identity thereto.

In some specific embodiments, the third antigen-binding domain that specifically binds to TIGIT comprises a full-length heavy chain (HC) and a full-length light chain (LC).

For example, the full-length heavy chain is of the IgG1, IgG2, or IgG4 isotype, and the full-length light chain is of the Kappa isotype;

for example, the heavy chain sequence is the amino acid sequence set forth in SEQ ID NO: 67 or has at least 80% or at least 90% sequence identity thereto, and the light chain sequence is the amino acid sequence set forth in SEQ ID NO: 68 or has at least 80% or at least 90% sequence identity thereto.

In some embodiments, in the aforementioned PD-1/PVRIG/TIGIT-binding protein, the first antigen-binding domain that specifically binds to PD-1, the second antigen-binding domain that specifically binds to PVRIG, and the third antigen-binding domain that specifically binds to TIGIT are linked, either directly or by a linker. For example, the linker is an amino acid sequence represented by $(G_4S)_x$, wherein x is independently selected from an integer of 1-20; for example, the linker is an amino acid sequence represented by $(G_4S)_2$, $(G_4S)_3$, or $(G_4S)_4$.

In some embodiments, in the aforementioned PD-1/PVRIG/TIGIT-binding protein, the antigen-binding domain that specifically binds to PD-1 is located at the N-terminus or C-terminus of the antigen-binding domain that specifically binds to PVRIG.

In some embodiments, in the aforementioned PD-1/PVRIG/TIGIT-binding protein, the antigen-binding domain that specifically binds to PD-1 is located at the N-terminus or C-terminus of the antigen-binding domain that specifically binds to TIGIT.

In some embodiments, in the aforementioned PD-1/PVRIG/TIGIT-binding protein, the antigen-binding domain that specifically binds to PVRIG is located at the N-terminus or C-terminus of the antigen-binding domain that specifically binds to TIGIT.

In some embodiments, the first antigen-binding domain, the second antigen-binding domain, and the third antigen-binding domain are on the same polypeptide chain or not.

In some embodiments, the aforementioned PD-1/PVRIG/TIGIT-binding protein comprises a first polypeptide chain and a second polypeptide chain represented by structures selected from the group consisting of the following:

(I) a first polypeptide chain: [the first antigen-binding domain that specifically binds to PD-1]-[linker 1]a-[the second antigen-binding domain that specifically binds to PVRIG]-[linker 2]b-[the VH of the third antigen-binding domain that specifically binds to TIGIT]-CH1-Fc, and a second polypeptide chain: [the VL of the third antigen-binding domain that specifically binds to TIGIT]-Cκ; or (II) a first polypeptide chain: [the second antigen-binding domain that specifically binds to PVRIG]-[linker 2]b-[the VH of the third antigen-binding domain that specifically binds to TIGIT]-CH1-Fc, and a second polypeptide chain: [the first antigen-binding domain that specifically binds to PD-1]-[linker 3]c-[the VL of the third antigen-binding domain that specifically binds to TIGIT]-Cκ; or (III) a first polypeptide chain: [the second antigen-binding domain that specifically binds to PVRIG]-[linker 2]b-[the VH of the third antigen-binding domain that specifically binds to TIGIT]-CH1-Fc-[linker 4]d-[the first antigen-binding domain that specifically binds to PD-1], and a second polypeptide chain: [the VL of the third antigen-binding domain that specifically binds to TIGIT]-Cκ; or (IV) a first polypeptide chain: [the second antigen-binding domain that specifically binds to PVRIG]-[linker 2]b-

[the VH of the third antigen-binding domain that specifically binds to TIGIT]-CH1-Fc, and a second polypeptide chain: [the VL of the third antigen-binding domain that specifically binds to TIGIT]-Cκ-[linker 5]e-[the first antigen-binding domain that specifically binds to PD-1].

The above first and second polypeptide chains are shown in order from N-terminus to C-terminus.

represents a peptide bond; the linkers are polypeptides capable of fulfilling the function of linking; linker 1, linker 2, linker 3, linker 4, and linker 5 may be identical or different; a. b, c, d, and e may optionally independently be 0 or 1.

For example, each of the linkers is independently a linker of EPKSS or $(G_xS)_y$, wherein x is selected from an integer of 1-5 (e.g., 1, 2, 3, 4, or 5), and y is selected from an integer of 1-6 (e.g., 1, 2, 3, 4, 5, or 6).

When a linker is a linker of $(G_xS)_y$, it is a linker represented by, for example, any of $(G_4S)_2$, $(G_4S)_3$, and $(G_4S)_4$.

In some embodiments, provided is a PD-1/PVRIG/TIGIT-binding protein, comprising a first polypeptide chain and a second polypeptide chain, wherein:

- the first and second polypeptide chains comprise the amino acid sequences set forth in SEQ ID NOs: 87 and 68, respectively;
- the first and second polypeptide chains comprise the amino acid sequences set forth in SEQ ID NOs: 84 and 88, respectively;
- the first and second polypeptide chains comprise the amino acid sequences set forth in SEQ ID NOs: 89 and 68, respectively;
- the first and second polypeptide chains comprise the amino acid sequences set forth in SEQ ID NOs: 84 and 90, respectively; or the first and second polypeptide chains comprise the amino acid sequences set forth in SEQ ID NOs: 91 and 68, respectively;
- the first and second polypeptide chains comprise the amino acid sequences set forth in SEQ ID NOs: 85 and 92, respectively;
- the first and second polypeptide chains comprise the amino acid sequences set forth in SEQ ID NOs: 93 and 68, respectively;
- the first and second polypeptide chains comprise the amino acid sequences set forth in SEQ ID NOs: 85 and 94, respectively;
- the first and second polypeptide chains comprise the amino acid sequences set forth in SEQ ID NOs: 97 and 68, respectively;
- the first and second polypeptide chains comprise the amino acid sequences set forth in SEQ ID NOs: 98 and 68, respectively;

or a combination of amino acid sequences having at least 80% or at least 90% sequence identity to any of the aforementioned first and second polypeptide chains.

In some embodiments, the aforementioned PD-1/PVRIG/TIGIT-binding protein of the present disclosure comprises two identical or different first polypeptide chains and two identical or different second polypeptide chains.

In some specific embodiments, the PD-1/PVRIG/TIGIT-binding protein comprises two identical first polypeptide chains and two identical second polypeptide chains.

In some embodiments, comprising the antigen-binding domain of the present disclosure that specifically binds to PD-1, the PD-1/PVRIG/TIGIT-binding protein of the present disclosure has all or any of its properties and functions.

Comprising the PVRIG/TIGIT-binding domains, the PD-1/PVRIG/TIGIT-binding protein further has at least one of the following characteristics:

(a) binding to human PVRIG with a $K_D$ value of less than $1\times10^{-7}$ M;

(b) blocking the interaction of PVRIG with its ligand (e.g., PVRL2);

(c) eliminating the inhibition of T cells by dendritic cells (DCs) and activating T cells; and (d) eliminating the inhibition of NK cells by tumor cells.

In some embodiments, the aforementioned PD-1/PVRIG/TIGIT-binding protein of the present disclosure is capable of inhibiting tumor growth by at least about 10%, e.g., at least about 20%, about 30%, about 40%, about 50%, about 60%, about 70%, about 80%, or about 90%.

In some embodiments, the aforementioned PD-1/PVRIG/TIGIT-binding protein of the present disclosure encompasses a variant, wherein the variant has one or more (e.g., 1, 2, 3, 4, 5, 6, 7, 8, 9, or 10) amino acid mutations as compared to any of the combinations of first and second polypeptide chains; the amino acid mutations may be conservative replacements, substitutions, or modifications, and/or deletions or additions that do not affect function. The mutations may occur in the antigen-binding domain that specifically binds to PD-1, the antigen-binding domain that specifically binds to PVRIG, or the antigen-binding domain that specifically binds to TIGIT (e.g., the CDRs and/or FRs).

In some embodiments, provided is a PD-1/PVRIG/TIGIT-binding protein that binds to or competes for binding to the same PD-1, PVRIG, and/or TIGIT or epitopes thereof with the aforementioned PD-1/PVRIG/TIGIT-binding protein of the present disclosure; or blocks the binding of the aforementioned PD-1/PVRIG/TIGIT-binding protein of the present disclosure to PD-1, PVRIG, and/or TIGIT; or whose binding to PD-1, PVRIG, and/or TIGIT is blocked by the aforementioned PD-1/PVRIG/TIGIT-binding protein of the present disclosure.

PD-1/PVRIG-Binding Protein, PD-1/TIGIT-Binding Protein

The present disclosure provides a PD-1/PVRIG-binding protein, comprising an antigen-binding domain that specifically binds to PD-1 and an antigen-binding domain that specifically binds to PVRIG, which is capable of specifically binding to PD-1 and PVRIG simultaneously or separately.

The present disclosure provides a PD-1/TIGIT-binding protein, comprising an antigen-binding domain that specifically binds to PD-1 and an antigen-binding domain that specifically binds to TIGIT, which is capable of specifically binding to PD-1 and TIGIT simultaneously or separately.

In some embodiments, the aforementioned PD-1/PVRIG-binding protein comprises or is an anti-PD-1/PVRIG bispecific antibody, and the aforementioned PD-1/TIGIT-binding protein comprises or is an anti-PD-1/TIGIT bispecific antibody.

In some embodiments, each of the antigen-binding domains in the aforementioned PD-1/PVRIG-binding protein or PD-1/TIGIT-binding protein is selected from the group consisting of a Fab, an Fv, an sFv, a Fab', a $F(ab')_2$, a linear antibody, a single-chain antibody, an scFv, an sdAb, an sdFv, a nanobody, a peptibody, a domain antibody, and any combination thereof.

In some embodiments, the antigen-binding domain that specifically binds to PD-1 comprises or is a VHH, the antigen-binding domain that specifically binds to PVRIG comprises or is a VHH, and the antigen-binding domain that specifically binds to TIGIT is a Fab or $F(ab')_2$.

In some embodiments, the aforementioned PD-1/PVRIG-binding protein or PD-1/TIGIT-binding protein is modified by humanization, affinity maturation, T cell epitope removal, reduction of antibody deamidation, and/or reduction of antibody isomerization.

In some embodiments, the aforementioned PD-1/PVRIG-binding protein or PD-1/TIGIT-binding protein is a recombinant antibody, a camelid antibody, a chimeric antibody, a humanized antibody, a fully human antibody, or an antigen-binding fragment thereof.

In some embodiments, in the PD-1/PVRIG-binding protein or PD-1/TIGIT-binding protein, the antigen-binding domain that specifically binds to PD-1 comprises at least one immunoglobulin single variable domain, and the immunoglobulin single variable domain comprises:

a CDR1, a CDR2, and a CDR3 from the amino acid sequence set forth in any of SEQ ID NOs: 3, 13-15, and 17-35, or a CDR1, a CDR2, and a CDR3 from the amino acid sequence set forth in any of SEQ ID NOs: 2 and 16;

the CDR1, CDR2, and CDR3 are defined according to the Kabat, IMGT, Chothia, AbM, or Contact numbering scheme.

In some embodiments, according to the Kabat numbering scheme, the amino acid sequences of the CDR1, CDR2, and CDR3 of the immunoglobulin single variable domain are set forth in:

SEQ ID NOs: 7, 36, and 37, respectively, or

SEQ ID NOs: 4, 5, and 6, respectively.

In some specific embodiments, of the immunoglobulin single variable domain, the amino acid sequence of the CDR1 is set forth in SEQ ID NO: 7, the amino acid sequence of the CDR2 is set forth in any of SEQ ID NOs: 8, 38-40, and 101, and the amino acid sequence of the CDR3 is set forth in any of SEQ ID NOs: 9, 41, and 42.

In some specific embodiments, the amino acid sequences of the CDR1, CDR2, and CDR3 of the immunoglobulin single variable domain are set forth in SEQ ID NOs: 7, 38, and 41, respectively.

In some embodiments, in the aforementioned PD-1/PVRIG-binding protein, the antigen-binding domain that specifically binds to PVRIG comprises at least one immunoglobulin single variable domain, and the immunoglobulin single variable domain comprises:

a CDR1, a CDR2, and a CDR3 from the amino acid sequence set forth in any of SEQ ID NOs: 45, 62-66, and 95-96, or a CDR1, a CDR2, and a CDR3 from the amino acid sequence set forth in any of SEQ ID NOs: 44 and 57-61.

In some specific embodiments, according to the Kabat numbering scheme, the amino acid sequences of the CDR1, CDR2, and CDR3 of the immunoglobulin single variable domain are set forth in:

SEQ ID NOs: 49, 50, and 51, respectively, or

SEQ ID NOs: 46, 47, and 48 or 99, respectively.

In some embodiments, in the aforementioned PD-1/TIGIT-binding protein, the antigen-binding domain that specifically binds to TIGIT comprises a heavy chain variable region (VH) and a light chain variable region (VL), wherein:

the heavy chain variable region comprises a HCDR1, a HCDR2, and a HCDR3, the amino acid sequences of which are set forth in SEQ ID NOs: 73, 74, and 75, respectively; the light chain variable region comprises a LCDR1, a LCDR2, and a LCDR3, the amino acid sequences of which are set forth in SEQ ID NOs: 76, 77, and 78, respectively.

In some embodiments, in the aforementioned PD-1/PVRIG-binding protein or PD-1/TIGIT-binding protein, the antigen-binding domain that specifically binds to PD-1 comprises the amino acid sequence set forth in any of SEQ ID NOs: 3, 13-15, and 17-35; or the amino acid sequence set forth in any of SEQ ID NOs: 2 and 16; or an amino acid sequence having at least 80%, at least 85%, or at least 90% sequence identity to any of the sequences.

In some embodiments, in the aforementioned PD-1/PVRIG-binding protein, the antigen-binding domain that specifically binds to PVRIG comprises: the amino acid sequence set forth in any of SEQ ID NOs: 45, 62-66, and 95-96; or the amino acid sequence set forth in any of SEQ ID NOs: 44 and 57-61; or an amino acid sequence having at least 80%, at least 85%, or at least 90% sequence identity to any of the sequences.

In some embodiments, in the aforementioned PD-1/TIGIT-binding protein, the antigen-binding domain that specifically binds to TIGIT comprises a heavy chain variable region (VH) and a light chain variable region (VL), wherein:

the heavy chain variable region comprises the amino acid sequence set forth in any of SEQ ID NOs: 79-81 or an amino acid sequence having at least 80% or at least 90% identity thereto; the light chain variable region comprises the amino acid sequence set forth in SEQ ID NO: 82 or 83 or an amino acid sequence having at least 80% or at least 90% identity thereto.

In some specific embodiments, the third antigen-binding domain that specifically binds to TIGIT comprises a full-length heavy chain (HC) and a full-length light chain (LC).

For example, the full-length heavy chain is of the IgG1, IgG2, or IgG4 isotype, and the full-length light chain is of the Kappa isotype.

For example, the heavy chain sequence is the amino acid sequence set forth in SEQ ID NO: 67 or has at least 80% or at least 90% sequence identity thereto, and the light chain sequence is the amino acid sequence set forth in SEQ ID NO: 68 or has at least 80% or at least 90% sequence identity thereto.

In some embodiments, in the aforementioned PD-1/PVRIG-binding protein or PD-1/TIGIT-binding protein, different antigen-binding domains are linked, either directly or by a linker; for example, the linker is independently an amino acid sequence represented by $(G_4S)_x$, wherein x is independently selected from an integer of 1-20 (e.g., 1, 2, 3, 4, 5, 6, 7, or 8); for example, the linker is independently an amino acid sequence represented by $(G_4S)_2$ or $(G_4S)_3$.

In some embodiments, in the aforementioned PD-1/PVRIG-binding protein, the antigen-binding domain that specifically binds to PD-1 is located at the N-terminus or C-terminus of the antigen-binding domain that specifically binds to PVRIG.

In some embodiments, in the aforementioned PD-1/TIGIT-binding protein, the antigen-binding domain that specifically binds to PD-1 is located at the N-terminus or C-terminus of the antigen-binding domain that specifically binds to TIGIT.

In some embodiments, the aforementioned PD-1/PVRIG-binding protein or PD-1/TIGIT-binding protein further comprises a human immunoglobulin Fc region; for example, the Fc region is the Fc region of human IgG1, IgG2, or IgG4. The Fc region may have a mutation; exemplary mutations are mutations S228P, F234A, L235A, and/or K447A. In some embodiments, the Fc region enables the binding protein to form a dimeric molecule to extend the in vivo half-life of the binding protein.

In some embodiments, having the antigen-binding domain of the present disclosure that specifically binds to PD-1, the PD-1/PVRIG-binding protein or PD-1/TIGIT-binding protein of the present disclosure has all or any of its properties and functions.

In some embodiments, the aforementioned PD-1/PVRIG-binding protein of the present disclosure is capable of inhibiting tumor growth by at least about 10%, e.g., at least about 20%, about 30%, about 40%, about 50%, about 60%, about 70%, about 80%, or about 90% or more.

In some embodiments, the PD-1/PVRIG-binding protein or PD-1/TIGIT-binding protein of the present disclosure encompasses a variant, wherein the variant has one or more (e.g., 1, 2, 3, 4, 5, 6, 7, 8, 9, or 10) amino acid mutations as compared to the aforementioned PD-1/PVRIG-binding protein or PD-1/TIGIT-binding protein; the amino acid mutations may be conservative replacements, substitutions, or modifications, and/or deletions and additions that do not affect function; the mutations may occur in the CDRs and/or FRs of the antigen-binding domain that specifically binds to PD-1, the antigen-binding domain that specifically binds to PVRIG, or the antigen-binding domain that specifically binds to TIGIT.

In some embodiments, provided is a PD-1/PVRIG-binding protein or PD-1/TIGIT-binding protein that binds to or competes for binding to the same PD-1, PVRIG, and/or TIGIT or epitopes thereof with the aforementioned PD-1/PVRIG-binding protein or PD-1/TIGIT-binding protein of the present disclosure; or blocks the binding of the aforementioned PD-1/PVRIG-binding protein or PD-1/TIGIT-binding protein of the present disclosure to PD-1, PVRIG, and/or TIGIT; or whose binding to PD-1, PVRIG, and/or TIGIT is blocked by the aforementioned PD-1/PVRIG-binding protein or PD-1/TIGIT-binding protein of the present disclosure.

In some embodiments, provided is a PVRIG-binding protein, comprising the antigen-binding domain of the aforementioned PD-1/PVRIG-binding protein that specifically binds to PVRIG.

In the present disclosure, when referring to a PVRIG-binding protein or an antigen-binding domain that specifically binds to PVRIG, it may comprise or be selected from a PVRIG antibody from WO2016134333, WO2016134335, WO2018033798, WO2018220446, WO2019079777, WO2019232484, WO2020018879, WO2021021837, WO2021097294, WO2021091605, or WO2021113831. For example, the PVRIG antibody may be any of CPA.7.002, CPA.7.005, CPA.7.021, and CPA.7.050 (see WO2016134333). The above patents are incorporated herein by reference in their entirety.

In some embodiments, provided is a TIGIT-binding protein, comprising the antigen-binding domain of the aforementioned PD-1/TIGIT-binding protein that specifically binds to TIGIT.

In the present disclosure, when referring to a TIGIT-binding protein or an antigen-binding domain that specifically binds to TIGIT, it may comprise or be selected from a TIGIT antibody from WO2019062832, WO2009126688, WO2014089113, WO2015009856, WO2015143343, WO2015174439, WO2016028656, WO2016106302, WO2017053748, WO2017030823, US20160176963, US20130251720, WO2019232484, or WO2019062832. For example, the TIGIT antibody may be any of CPA.9.083.H4 (S241P), CPA.9.086.H4(S241P), CHA.9.547.7.H4(S241P), and CHA.9.547.13.H4(S241P) (see WO2019232484). The above patents are incorporated herein by reference in their entirety.

In some embodiments, provided is a PVRIG/TIGIT-binding protein, comprising, of the aforementioned PD-1/PVRIG/TIGIT-binding protein, the antigen-binding domain that specifically binds to TIGIT and the antigen-binding domain that specifically binds to PVRIG.

Polynucleotide and Vector

The present disclosure provides a polynucleotide encoding the PD-1-binding protein, PD-1/PVRIG/TIGIT-binding protein, PD-1/PVRIG-binding protein, PD-1/TIGIT-binding protein, PVRIG-binding protein, or TIGIT-binding protein of the present disclosure. The polynucleotide of the present disclosure may be an RNA, DNA, or cDNA. According to some embodiments of the present disclosure, the polynucleotide of the present disclosure is a substantially isolated polynucleotide.

The polynucleotide of the present disclosure may be in the form of, may be present in, and/or may be part of a vector, such as a plasmid, cosmid, YAC, or viral vector. The vector may especially be an expression vector, i.e., a vector that provides for the in vitro and/or in vivo (i.e., in suitable host cells, host organisms and/or expression systems) expression of the PD-1-binding protein. The expression vector generally comprises at least one of the polynucleotides of the present disclosure, which is operably linked to one or more suitable expression regulatory elements (e.g., promoters, enhancers, terminators, and the like). The selection of the elements and their sequences for expression in a particular host is within the knowledge of those skilled in the art. Regulatory elements and other elements useful or necessary for expression of the PD-1-binding protein, PD-1/PVRIG/TIGIT-binding protein, PD-1/PVRIG-binding protein, PD-1/TIGIT-binding protein, PVRIG-binding protein, or TIGIT-binding protein of the present disclosure include, for example, promoters, enhancers, terminators, integration factors, selection labels, leader sequences, and reporter genes.

The polynucleotide of the present disclosure may be prepared or obtained by known means (e.g., by automatic DNA synthesis and/or recombinant DNA techniques) based on information on the amino acid sequence of the polypeptide of the present disclosure, and/or may be isolated from a suitable natural source.

Host Cell

The present disclosure provides a recombinant host cell that expresses or is capable of expressing one or more of the PD-1-binding proteins, PD-1/PVRIG/TIGIT-binding proteins, PD-1/PVRIG-binding proteins, PD-1/TIGIT-binding proteins, PVRIG-binding proteins, or TIGIT-binding proteins of the present disclosure, and/or contains the nucleic acid or vector of the present disclosure. In some embodiments, the host cell is a bacterial cell, a fungal cell or a mammalian cell.

Bacterial cells include, for example, cells of gram-negative bacterial strains (e.g., *Escherichia coli* strains, *Proteus* strains, and *Pseudomonas* strains), and gram-positive bacterial strains (e.g., *Bacillus* strains, *Streptomyces* strains, *Staphylococcus* strains, and *Lactococcus* strains).

Fungal cells include, for example, cells of species of *Trichoderma, Neurospora*, and *Aspergillus*; or cells of species of *Saccharomyces* (e.g., *Saccharomyces cerevisiae*), *Schizosaccharomyces* (e.g., *Schizosaccharomyces pombe*), *Pichia* (*Pichia pastoris* and *Pichia methanolica*), and *Hansenula.*

Mammalian cells include, for example, HEK293 cells, CHO cells, BHK cells, HeLa cells, COS cells, and the like.

However, amphibian cells, insect cells, plant cells, and any other cells used in the art for expressing heterologous proteins may also be used in the present disclosure. The cells of the present disclosure are unable to develop into complete plants or individual animals.

Production or Preparation Method

The present disclosure provides a method for preparing the PD-1-binding protein, PD-1/PVRIG/TIGIT-binding protein, PD-1/PVRIG-binding protein, PD-1/TIGIT-binding protein, PVRIG-binding protein, or TIGIT-binding protein of the present disclosure.

The method generally comprises the following steps:

culturing the host cell of the present disclosure under conditions that allow expression of the binding protein of the present disclosure; and collecting the binding protein expressed by the host cell from the culture; and optionally, further purifying and/or modifying the binding protein of the present disclosure.

The PD-1-binding protein, PD-1/PVRIG/TIGIT-binding protein, PD-1/PVRIG-binding protein, PD-1/TIGIT-binding protein, PVRIG-binding protein, or TIGIT-binding protein of the present disclosure can be produced intracellularly (e.g., in the cytoplasm, in the periplasm, or in inclusion bodies) in the cell described above, followed by isolation from the host cell and optionally further purification; or it may be produced extracellularly (e.g., in the medium in which the host cell is cultured), followed by isolation from the medium and optionally further purification.

Methods and reagents for recombinant production of polypeptides, e.g., specific suitable expression vectors, transformation or transfection methods, selection labels, methods for inducing protein expression, culture conditions, and the like, are known in the art. Similarly, isolation and purification techniques suitable for use in the manufacture of the binding protein or antibody of the present disclosure are well known to those skilled in the art. Methods for producing and purifying antibodies are well known in the prior art and can be found in, for example, "Antibodies: A Laboratory Manual", Cold Spring Harbor Press (chapters 5-8 and 15). The engineered antibodies of the present disclosure may also be prepared and purified by conventional methods. For example, cDNA sequences encoding the heavy and light chains can be cloned and recombined into an expression vector. The expression vector can stably transfect cells. Mammalian expression systems may result in glycosylation of antibodies, particularly at the highly conserved N-terminus of the Fc region. Stable clones are obtained by expression of antibodies specifically binding to the human-derived antigen. Positive clones are expanded in a serum-free medium of a bioreactor to produce antibodies. The culture medium with the secreted antibody can be purified and collected by conventional techniques. The antibody can be filtered and concentrated by conventional methods. Soluble mixtures and multimers can also be removed by conventional methods, such as molecular sieves and ion exchange. The resulting product needs to be immediately frozen, e.g., at −70° C., or lyophilized.

However, the PD-1-binding protein, PD-1/PVRIG/TIGIT-binding protein, PD-1/PVRIG-binding protein, PD-1/TIGIT-binding protein, PVRIG-binding protein, or TIGIT-binding protein of the present disclosure may also be obtained by other methods for producing proteins known in the art, such as chemical synthesis, including solid-phase or liquid-phase synthesis.

Composition/Pharmaceutical Composition

The present disclosure provides a composition, comprising the aforementioned PD-1-binding protein, PD-1/PVRIG/TIGIT-binding protein, PD-1/PVRIG-binding protein, PD-1/TIGIT-binding protein, PVRIG-binding protein, and/or TIGIT-binding protein.

For example, provided is a pharmaceutical composition, comprising an amount, effective in treating, alleviating, or preventing cancer, of the PD-1-binding protein, PD-1/PVRIG/TIGIT-binding protein, PD-1/PVRIG-binding protein, and/or PD-1/TIGIT-binding protein described above and at least one pharmaceutically acceptable excipient, diluent, or carrier.

In some specific embodiments, a unit dose of the pharmaceutical composition may comprise 0.01 to 99 weight % of the PD-1-binding protein, PD-1/PVRIG/TIGIT-binding protein, PD-1/PVRIG-binding protein, and/or PD-1/TIGIT-binding protein, or the amount of the PD-1-binding protein, PD-1/PVRIG/TIGIT-binding protein, PD-1/PVRIG-binding protein, and/or PD-1/TIGIT-binding protein in a unit dose of the pharmaceutical composition is 0.1-2000 mg, and in some embodiments, 1-1000 mg.

In some embodiments, provided is a product or kit, comprising at least one container, and each container independently contains the aforementioned PD-1-binding protein, PD-1/PVRIG/TIGIT-binding protein, PD-1/PVRIG-binding protein, and/or PD-1/TIGIT-binding protein. Optionally, the kit comprises a container and a label. Examples of containers are bottles, syringes, and test tubes. The container accommodates a composition effective in treating a disorder. The label on or associated with the container indicates that the composition is used for treating the disorder of choice. The composition comprises the aforementioned PD-1-binding protein, PD-1/PVRIG/TIGIT-binding protein, PD-1/PVRIG-binding protein, and/or PD-1/TIGIT-binding protein.

In some embodiments, provided is a pharmaceutical composition, comprising the PD-1-binding protein and PVRIG-binding protein of the present disclosure. Some other pharmaceutical compositions comprise the PD-1-binding protein and TIGIT-binding protein of the present disclosure. Some other pharmaceutical compositions comprise the PD-1-binding protein, TIGIT-binding protein, and PVRIG-binding protein of the present disclosure. The PD-1-binding protein, TIGIT-binding protein, and/or PVRIG-binding protein may be present in an amount effective in treating or alleviating a disease (e.g., cancer). The pharmaceutical composition may further comprise at least one pharmaceutically acceptable excipient, diluent, or carrier.

By way of example, provided is a composition, product, or kit, comprising any of the following or a combination thereof.

any PD-1-binding protein provided by the present disclosure;

any PD-1/PVRIG/TIGIT-binding protein provided by the present disclosure;

any PD-1/PVRIG-binding protein provided by the present disclosure;

any PD-1/TIGIT-binding protein provided by the present disclosure;

any PD-1-binding protein provided by the present disclosure and any PVRIG/TIGIT-binding protein provided by the present disclosure;

any PD-1-binding protein provided by the present disclosure and any PVRIG-binding protein provided by the present disclosure;

any PD-1-binding protein provided by the present disclosure and any TIGIT-binding protein provided by the present disclosure; or any PD-1-binding protein provided by the present disclosure, any PVRIG-binding protein provided by the present disclosure, and any TIGIT-binding protein provided by the present disclosure.

Optionally, when the composition is a pharmaceutical composition, it further comprises at least one pharmaceutically acceptable excipient, diluent, or carrier.

Method for Treating Disease and Pharmaceutical Use

The present disclosure provides a method for treating, alleviating, preventing, or diagnosing a disease or disorder using the aforementioned PD-1-binding protein, PD-1/PVRIG/TIGIT-binding protein, PD-1/PVRIG-binding protein, PD-1/TIGIT-binding protein, PVRIG/TIGIT-binding protein, PVRIG-binding protein, TIGIT-binding protein, polynucleotide, or composition (including the pharmaceutical composition).

In some embodiments, provided is a method for ameliorating, alleviating, treating, or preventing a disease, comprising administering to a subject an amount, effective in amelioration, alleviation, treatment, or prevention, of the aforementioned PD-1-binding protein, PD-1/PVRIG/TIGIT-binding protein, PD-1/PVRIG-binding protein, PD-1/TIGIT-binding protein, PVRIG-binding protein, TIGIT-binding protein, polynucleotide, or composition (including the pharmaceutical composition).

In some embodiments, provided is use of the PD-1-binding protein, PD-1/PVRIG/TIGIT-binding protein, PD-1/PVRIG-binding protein, PD-1/TIGIT-binding protein, or PVRIG/TIGIT-binding protein of the present disclosure in the preparation of a medicament for ameliorating, alleviating, treating, or preventing a disease.

In some embodiments, provided is use of a combination of the PD-1-binding protein and PVRIG-binding protein of the present disclosure in the preparation of a medicament for ameliorating, alleviating, treating, or preventing a disease.

In some embodiments, provided is use of a combination of the PD-1-binding protein and TIGIT-binding protein of the present disclosure in the preparation of a medicament for ameliorating, alleviating, treating, or preventing a disease.

In some embodiments, provided is use of a combination of the PD-1-binding protein, PVRIG-binding protein, and TIGIT-binding protein of the present disclosure in the preparation of a medicament for ameliorating, alleviating, treating, or preventing a disease.

In some embodiments, provided is use of a combination of the PD-1-binding protein and PVRIG/TIGIT-binding protein of the present disclosure in the preparation of a medicament for ameliorating, alleviating, treating, or preventing a disease.

In some embodiments, provided is the PD-1-binding protein of the present disclosure for use in ameliorating, alleviating, treating, or preventing a disease, in combination with the PVRIG-binding protein and/or TIGIT-binding protein, or in combination with the PVRIG/TIGIT-binding protein.

In some embodiments, provided is the method for ameliorating, alleviating, treating, or preventing a disease using the PD-1-binding protein of the present disclosure, further comprising administering the PVRIG-binding protein and/or TIGIT-binding protein, or further comprising administering the PVRIG/TIGIT-binding protein.

In some embodiments, provided is the method for ameliorating, alleviating, treating, or preventing a disease using the PVRIG-binding protein and/or TIGIT-binding protein of the present disclosure, further comprising administering the PD-1-binding protein of the present disclosure.

In some embodiments, provided is the method for ameliorating, alleviating, treating, or preventing a disease using the PVRIG/TIGIT-binding protein of the present disclosure, further comprising administering the PD-1-binding protein of the present disclosure.

In some embodiments, the aforementioned disease is a proliferative disease or any other disease or disorder characterized by uncontrolled cell growth (e.g., cancer; in the present disclosure, cancer and tumor are used interchangeably), e.g., a disease associated with overexpression of PD-L1 or abnormal expression of PVRIG and TIGIT (e.g., cancer).

In some embodiments, the aforementioned cancer is a solid tumor or hematological tumor.

In some embodiments, the aforementioned cancer is advanced or metastatic.

In some embodiments, the aforementioned cancer is selected from the group consisting of the following or a combination thereof: prostate cancer, liver cancer (HCC), colorectal cancer, ovarian cancer, endometrial cancer, breast cancer, triple negative breast cancer, pancreatic cancer, stomach/gastric cancer, cervical cancer, head and neck cancer, thyroid cancer, testicular cancer, urothelial cancer, lung cancer (small cell lung cancer or non-small cell lung cancer), melanoma, non-melanoma skin cancer (squamous and basal cell carcinoma), neuroglioma, renal cancer (RCC), lymphoma (NHL or HL), acute myeloid leukemia (AML), T-cell acute lymphoblastic leukemia (T-ALL), diffuse large B-cell lymphoma, testis germ cell tumor, mesothelioma, esophageal cancer, Merkel cell cancer, MSI-high cancer, KRAS-mutant tumor, adult T-cell leukemia/lymphoma, and myelodysplastic syndrome (MDS). For example, the aforementioned cancer is selected from the group consisting of lung cancer, prostate cancer, breast cancer, head and neck cancer, esophageal cancer, gastric cancer, colon cancer, colorectal cancer, bladder cancer, cervical cancer, uterine cancer, ovarian cancer, liver cancer, melanoma, renal cancer, squamous cell carcinoma, hematological cancer, and any other diseases or disorders characterized by uncontrolled cell growth.

In some embodiments, the aforementioned subject has a condition associated with PVRIG and/or TIGIT. In some embodiments, the condition of the subject includes a cancer that expresses or does not express PVRIG and further includes non-metastatic or non-infiltrative and infiltrative or metastatic cancer, wherein PVRIG expression of immune cells, stromal cells, or diseased cells inhibits an anti-tumor response and an anti-infiltration immune response. The methods of the present disclosure are suitable for treating vascularized cancers, for example.

In some embodiments, provided is a method for treating or preventing an infection or sepsis in a subject, comprising administering to the subject a therapeutically or prophylactically effective amount of the aforementioned PD-1-binding protein, PD-1/PVRIG/TIGIT-binding protein, PD-1/PVRIG-binding protein, PD-1/TIGIT-binding protein, PVRIG-binding protein, TIGIT-binding protein, polynucleotide, or composition (including the pharmaceutical composition). In some embodiments, the infection is a pathogen infection characterized by different degrees of dysfunction of a virus-specific T cell response, such as HIV, HCV, or HBV. In some embodiments, the sepsis includes severe sepsis, septic shock, systemic inflammatory response syndrome (SIRS), bacteremia, septicemia, toxemia, and septic syndrome.

In some embodiments, provided are a method for activating cytotoxic T lymphocytes (CTLs) in a subject, a method for activating NK cells in a subject, a method for activating γδT cells in a subject, a method for activating Th1 cells in a subject, a method for activating, reducing, or eliminating cell number and/or activity of at least one of regulatory T cells (Tregs), a method for increasing IFN-γ production and/or proinflammatory cytokine secretion in a subject, a method for inhibiting the interaction between PVRIG and PVRL2 in a subject, and a method for blocking or inhibiting the interaction between PD-1 and PD-L1/PD-L2 in a subject, all of which comprise administering to the subject an effective amount of the aforementioned PD-1-binding protein, PD-1/PVRIG/TIGIT-binding protein, PD-1/PVRIG-binding protein, PD-1/TIGIT-binding protein, PVRIG-binding protein, TIGIT-binding protein, polynucleotide, or composition (including the pharmaceutical composition).

Detection and Kit

The present disclosure provides use of the PD-1-binding protein, PD-1/PVRIG/TIGIT-binding protein, PD-1/PVRIG-binding protein, PD-1/TIGIT-binding protein, PVRIG/TIGIT-binding protein, PVRIG-binding protein, TIGIT-binding protein, polynucleotide, or composition for detection. The present disclosure further provides a method, system, or device for in vivo or in vitro detection of PD-1, PVRIG, or TIGIT, comprising treating a sample with the aforementioned binding protein, polynucleotide, or composition of the present disclosure.

In some embodiments, the method, system, or device for in vitro detection may comprise, for example, (1) contacting the sample with the PD-1-binding protein, PD-1/PVRIG/TIGIT-binding protein, PD-1/PVRIG-binding protein, PD-1/TIGIT-binding protein, PVRIG/TIGIT-binding protein, PVRIG-binding protein, TIGIT-binding protein, polynucleotide, or composition;

(2) detecting a complex formed between the aforementioned binding protein or polynucleotide and the sample; and/or (3) contacting a reference sample (e.g., a control sample) with the binding protein or nucleic acid; and (4) determining the extent of formation of the complex by comparison with the reference sample. A change (e.g., a statistically significant change) in the formation of the complex in the sample or subject as compared to a control sample or subject indicates the presence of PD-1, PVRIG, or TIGIT in the sample.

In some other embodiments, the method, system, or device for in vivo detection may comprise:

(1) administering to a subject the aforementioned binding protein or polynucleotide; and (2) detecting the formation of a complex between the aforementioned binding protein or polynucleotide and the subject.

The detection may include determining the location or time at which the complex is formed. The aforementioned binding protein or polynucleotide may be labeled with a detectable substance, and detection of a substance capable of binding to the protein or polynucleotide (e.g., PD-1, PVRIG, or TIGIT) is achieved by detection of the label. Suitable detectable substances include various enzymes, prosthetic groups, fluorescent substances, luminescent substances, and radioactive substances. The formation of the complex from the binding protein or polynucleotide and PD-1, PVRIG, or TIGIT can be detected by measuring or visualizing substances that bind or do not bind to PD-1, PVRIG, or TIGIT. Conventional detection assays may be used, such as enzyme-linked immunosorbent assay (ELISA), radioimmunoassay (RIA), or tissue immunohistochemistry. For detection purposes, the binding protein or polynucleotide of the present disclosure may be labeled with a fluorophore chromophore. In some embodiments, further provided are a diagnostic reagent comprising the polynucleotide or binding protein described above, and related diagnostic use.

In some embodiments, further provided is a kit, comprising the aforementioned binding protein or polynucleotide; the kit may further comprise instructions for diagnostic use. The kit may further comprise at least one additional reagent, such as a label or an additional diagnostic agent. For in vivo use, the binding protein may be formulated into a pharmaceutical composition.

BRIEF DESCRIPTION OF THE DRAWINGS

FIG. 1A shows the results for A6_IgG4 and A17_IgG4. FIG. 1B shows the results for A17h1_IgG4, A17m09_hIgG4, A17m0901_hIgG4, A17m0902_hIgG4, A17m0903 hIgG4, and A17m0905_hIgG4.

FIG. 3A is a graph showing the mouse tumor volume; FIG. 3B is a graph showing the mouse body weight; wherein pembrolizumab is used as a positive control and PBS as a negative control.

FIG. 6B is a corresponding graph showing the mouse body weight.

FIG. 7B is a corresponding graph showing the mouse body weight.

FIGS. 11A, 11B, and 1 IC show the capacities of anti-PD-1/PVRIG/TIGIT trispecific antibodies with optimized PVRIG sequences to bind to cells overexpressing PVRIG, TIGIT, and PD-1 antigens, respectively.

DETAILED DESCRIPTION

Definition of Terms

Figure 1A:
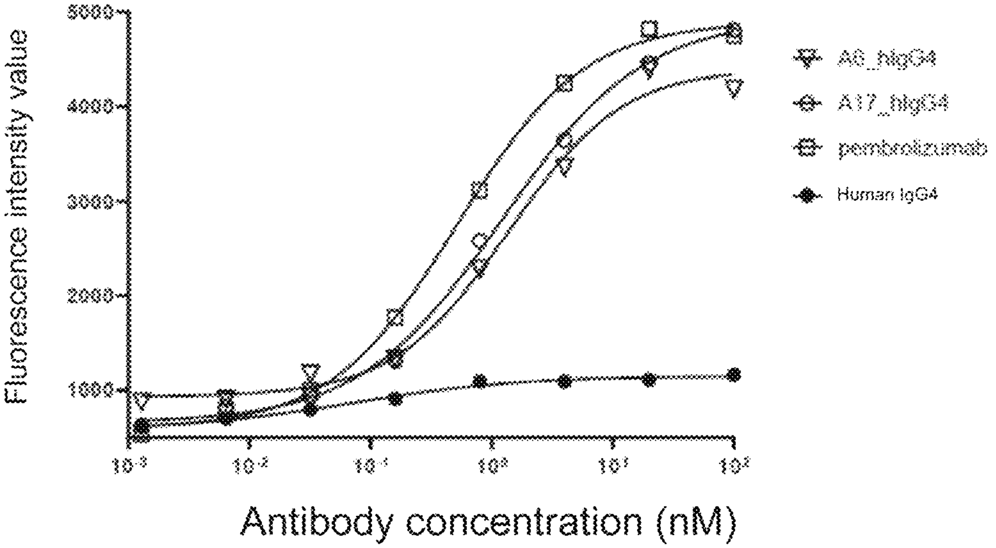
FIGS. 1A to 1B show the activity of anti-PD-1 nanobodies as measured by a PD-1/PD-L1 NFAT reporter gene system. Pembrolizumab is used as a positive control and hIgG4 as a negative control.

In order to facilitate the understanding of the present disclosure, some technical and scientific terms are specifically defined below. Unless otherwise specifically defined in the present disclosure, all other technical and scientific terms used in the present disclosure have the meanings generally understood by those of ordinary skill in the art to which the present disclosure pertains.

The three-letter and single-letter codes for amino acids used herein are as described in J. biol. chem., 243, p 3558 (1968).

"Programmed death-1", "programmed cell death-1", "protein PD-1", "PD-1", "PDCD1" and "hPD-1" are used interchangeably and include variants, isoforms, and species homologs of human PD-1, and analogs having at least one common epitope with PD-1. The complete PD-1 sequence can be found under GenBank accession No. U64863. "Programmed death ligand-1 (PD-L1)" is one of two cell surface glycoprotein ligands of PD-1 (the other being PD-L2) that downregulates T cell activation and cytokine secretion upon binding to PD-1. "PD-L1" as used herein includes human PD-L1 (hPD-L1), variants, isoforms, and interspecies homologs of hPD-L1, and analogs sharing at least one epitope with hPD-L1. The complete hPD-L1 sequence can be found under GenBank accession No. Q9NZQ7.

"PVRIG", "PVRIG protein", or "PVRIG polypeptide" may optionally include any such protein or a variant, a conjugate, or a fragment thereof, including but not limited to known or wild-type PVRIG described herein, as well as any naturally occurring splice variant, amino acid variant or isoform, in particular a soluble extracellular domain (ECD) fragment of PVRIG. ECD is defined herein as described in patent WO2016134333. The complete human PVRIG sequence can be found under GenBank accession No. AAH73861.1.

"TIGIT", "TIGIT protein", or "TIGIT polypeptide" may optionally include any such protein or a variant, a conjugate, or a fragment thereof, including (but not limited to) known or wild-type TIGIT described herein, as well as any naturally occurring splice variant, amino acid variant or isoform. The complete TIGIT sequence can be found under GenBank accession No. AAI01289.1.

"Binding to PD-1" refers to the ability to interact with PD-1 or an epitope thereof, wherein the PD-1 or the epitope thereof may be derived from humans. "Binding to PVRIG" refers to the ability to interact with PVRIG or an epitope thereof, wherein the PVRIG or the epitope thereof may be derived from humans. "Binding to TIGIT" refers to the ability to interact with TIGIT or an epitope thereof, wherein the TIGIT or the epitope thereof may be derived from humans. "Antigen-binding site" refers to a discontinuous three-dimensional spatial site on an antigen that is recognized by the antibody or the antigen-binding fragment of the present disclosure.

"PD-1-binding protein" encompasses any protein capable of specifically binding to PD-1 or any molecule capable of specifically binding to its epitopes. The PD-1-binding protein may include an antibody against PD-1 defined in the present disclosure, an antigen-binding fragment thereof, or a conjugate thereof. The PD-1-binding protein also encompasses immunoglobulin superfamily antibodies (IgSF) or CDR-grafted molecules. The "PD-1-binding protein" of the present disclosure may comprise at least one immunoglobulin single variable domain (such as a VHH) that binds to PD-1. In some embodiments, the "PD-1-binding protein" may comprise 2, 3, 4 or more immunoglobulin single variable domains (such as VHHs) that bind to PD-1. The PD-1-binding protein of the present disclosure may also comprise, in addition to the immunoglobulin single variable domain of PD-1, a linker and/or a moiety with effector function, such as a half-life extending moiety (e.g., an immunoglobulin single variable domain that binds to serum albumin), and/or a fusion partner (such as serum albumin) and/or a conjugated polymer (such as PEG) and/or an Fc region. In some embodiments, the "PD-1-binding protein" of the present disclosure also encompasses bispecific/multispecific antibodies comprising immunoglobulins that bind to different antigens (e.g., a first antibody that binds to a first antigen (e.g., PD-1) and a second antibody that binds to a second antigen (e.g., PVRIG), optionally a third specific antibody that binds to a third antigen (e.g., TIGIT), and further optionally a fourth antibody that binds to a fourth antigen). "PD-1-binding protein" encompasses "PD-1/PVRIG-binding protein", "PD-1/TIGIT-binding protein", and "PD-1/PVRIG/TIGIT-binding protein".

"PD-1-binding protein" or "anti-PD-1 antibody" of the present disclosure may comprise one or more effector molecules, for example, in a conjugated manner. The "effector molecules" include, for example, antineoplastic agents, drugs, toxins, biologically active proteins such as enzymes, other antibody or antibody fragments, synthetic or naturally occurring polymers, nucleic acids, and fragments thereof (such as DNA, RNA, and fragments thereof), radionuclides, particularly radioiodide, radioisotopes, chelated metals, nanoparticles and reporter groups such as fluorescent compounds or compounds which may be detected by NMR or ESR spectroscopy. When the effector molecule is a polymer, it may generally be a synthetic or naturally occurring polymer, for example, an optionally substituted straight or branched chain polyalkylene, polyalkenylene or polyoxyalkylene polymer or a branched or unbranched polysaccharide, such as a homo-polysaccharide or a hetero-polysaccharide. Specific optional substituents that may be present on the synthetic polymers described above include one or more hydroxy, methyl, or methoxy groups. Specific examples of synthetic polymers include optionally substituted linear or branched poly(ethylene glycol), poly(propylene glycol), poly(vinyl alcohol) or derivatives thereof, in particular optionally substituted poly(ethylene glycol), such as methoxy poly(ethylene glycol) or derivatives thereof. Specific naturally occurring polymers include lactose, amylose, dextran or glycogen or a derivative thereof. In one embodiment, the polymer is albumin or a fragment thereof, e.g., human serum albumin or a fragment thereof. Conjugation of the polymer to the PD-1-binding protein or anti-PD-1 antibody can be achieved by conventional methods.

"Cytokine" is a general term for proteins that are released by a cell population to act on other cells as intercellular mediators. Examples of such cytokines include lymphokines, monokines, chemokines, and traditional polypeptide hormones. Exemplary cytokines include: human IL-2, IFN-γ, IL-6, TNFα, IL-17 and IL-5.

"Antibody" encompasses a variety of antibody structures, including, but not limited to monoclonal antibodies, polyclonal antibodies; monospecific antibodies, multispecific antibodies (e.g., bispecific antibodies); and full-length antibodies, and antibody fragments (or antigen-binding fragments, or antigen-binding moieties) so long as they exhibit the desired antigen-binding activity. An antibody may refer to an immunoglobulin, which is of a four-peptide-chain structure formed by two heavy chains and two light chains linked by interchain disulfide bonds. The heavy chain constant regions of an immunoglobulin differ in their amino acid composition and arrangement, and thus in their antigenicity. Accordingly, immunoglobulins can be divided into five classes, or isotypes of immunoglobulins, namely IgM, IgD, IgG, IgA, and IgE, with their corresponding heavy chains being μ chain, δ chain, γ chain, α chain, and ε chain, respectively. Ig of the same class can be divided into different subclasses according to differences in the amino acid composition of the hinge regions and the number and positions of disulfide bonds of the heavy chains; for example, IgG can be divided into IgG1, IgG2, IgG3, and IgG4. Light chains are divided into κ or λ chains according to differences in the constant regions. Each of the five classes of Ig may have a κ chain or λ chain.

In the antibody heavy and light chains, the sequences of about 110 amino acids near the N-terminus vary considerably and thus are referred to as variable regions (V regions); the remaining amino acid sequences near the C-terminus are relatively stable and thus are referred to as constant regions (C regions). The variable regions comprise 3 hypervariable regions (HVRs) and 4 framework regions (FRs) with relatively conservative sequences. The 3 hypervariable regions determine the specificity of the antibody and thus are also known as complementarity determining regions (CDRs). Each of the light chain variable regions (VLs) and the heavy chain variable regions (VHs) consists of 3 CDRs and 4 FRs arranged from the amino-terminus to the carboxy-terminus in the following order: FR1, CDR1, FR2, CDR2, FR3, CDR3, and FR4. The 3 CDRs of the light chain refer to LCDR1, LCDR2, and LCDR3; and the 3 CDRs of the heavy chain refer to HCDR1, HCDR2, and HCDR3.

"Antigen-binding fragment" encompasses a single-chain antibody (i.e., full-length heavy and light chains); Fab, a modified Fab, Fab', a modified Fab', F(ab')2, Fv, Fab-Fv, Fab-dsFv, a single-domain antibody (e.g., VH or VL or VHH), scFv, a bivalent or trivalent or tetravalent antibody, Bis-scFv, a diabody, a tribody, a triabody, a tetrabody and an epitope-binding fragment of any of the above (see, e.g., Holliger and Hudson, 2005, Nature Biotech. 23(9): 1126-1136; Adair and Lawson, 2005, Drug Design Reviews-Online 2(3), 209-217).

Methods for producing and preparing such antigen-binding fragments are well known in the art (see, e.g., Verma et al., 1998, Journal of Immunological Methods, 216, 165-181). Fab-Fv was first disclosed in WO2009/040562, and its disulfide-stabilized form Fab-dsFv was first disclosed in WO2010/035012. The antigen-binding fragment of the present disclosure also includes Fab and Fab' fragments described in WO2005/003169, WO2005/003170, and WO2005/003171. Multivalent antibodies may comprise multiple specificities (e.g., bispecificites) or may be monospecific (see, e.g., WO92/22583 and WO05/113605), and an example of the latter is Tri-Fab (or TFM) described in WO 92/22583.

"Bispecific antibody" encompasses antibodies (including antibodies or antigen-binding fragments thereof, such as single-chain antibodies) capable of specifically binding to two different antigens, or two or at least two different epitopes of the same antigen. Bispecific antibodies of various structures have been disclosed in the prior art. The bispecific antibodies can be classified into IgG-like bispecific antibodies and antibody-fragment-type bispecific antibodies according to the integrity of IgG molecules. The bispecific antibodies can be classified into bivalent, trivalent, tetravalent, or higher-valent bispecific antibodies according to the number of the antigen-binding regions. The bispecific antibodies can be classified into symmetric bispecific antibodies and asymmetric bispecific antibodies according to whether their structures are horizontally symmetric or not. Among them, bispecific antibodies based on antibody fragments, such as Fab fragments lacking Fc fragments, formed by linking 2 or more Fab fragments in one molecule, have relatively low immunogenicity, small molecular weight, and relatively high tumor tissue permeability, and typical antibody structures of this type include such bispecific antibodies as F(ab)2, scFv-Fab, and (scFv)2-Fab. The IgG-like bispecific antibodies (e.g., antibodies having Fc fragments) have large relative molecular weight, and the Fc fragments facilitate the later purification of the antibodies and increase their solubility and stability, and the Fc fragments may further bind to the receptor FcRn and increase the serum half-life of the antibodies. Typical structural models of bispecific antibodies include bispecific antibodies such as KiH, CrossMAb, Triomab quadroma, FcAAdp, ART-Ig, BiMAb, Biclonics, BEAT, DuoBody, Azymetric, XmAb, 2:1 TCBs, 1Fab-IgG TDB, FynomAb, two-in-one/DAF, scFv-Fab-IgG, DART-Fc, LP-DART, CODV-Fab-TL, HLE-BiTE, $F(ab)_2$-CrossMAb, IgG-$(scFv)_2$, Bs4Ab, DVD-Ig, Tetravalent-DART-Fc, (scFv)4-Fc, CODV-Ig, mAb2, and $F(ab)_4$-CrossMAb (see Aran F. Labrijn et al., Nature Reviews Drug Discovery, volume 18, pages 585-608 (2019); Chen S1 et al., J Immunol Res., Feb. 11, 2019; 2019:4516041).

"Trispecific antibody" refers to an antibody capable of specifically binding to three or at least three different epitopes, which may be epitopes of different antigens or different epitopes of the same antigen.

For the determination or definition of "CDRs", the deterministic depiction of CDRs and identification of residues of antigen-binding sites can be accomplished by resolving the structure of the antibody and/or resolving the structure of the antibody-ligand complex. This can be accomplished by any of a variety of techniques known to those skilled in the art, such as X-ray crystallography. A variety of analysis methods can be used to identify CDRs, including but not limited to the Kabat numbering scheme, the Chothia numbering scheme, the AbM numbering scheme, the IMGT numbering scheme, the contact definition, and the conformational definition.

The Kabat numbering scheme is a standard for numbering residues in antibodies and is generally used to identify CDRs (see, e.g., Johnson & Wu, 2000, Nucleic Acids Res., 28:214-8). The Chothia numbering scheme is similar to the Kabat numbering scheme, except that it takes into account the position of certain structural loop regions. (see, e.g., Chothia et al., 1986, J. Mol. Biol., 196:901-17; Chothia et al., 1989, Nature, 342:877-83). The AbM numbering scheme adopts a computer program integration suite for modeling antibody structures manufactured by Oxford Molecular Group (see, e.g., Martin et al., 1989, Proc Natl Acad Sci (USA), 86:9268-9272; "AbM™, A Computer Program for Modeling Variable Regions of Antibodies", Oxford, UK; Oxford Molecular, Ltd.). The AbM numbering scheme adopts a combination of a knowledge database and the de-novo method to model the tertiary structure of antibodies from basic sequences (see those described in Samudrala et al., 1999, "Ab Initio Protein Structure Prediction Using a Combined Hierarchical Approach", PROTEINS, Structure, Function and Genetics Suppl., 3:194-198). The contact definition is based on the analysis of the available complex crystal structures (see, e.g., MacCallum et al., 1996, J. Mol. Biol., 5:732-45). In the conformational definition, the positions of the CDRs can be identified as residues that contribute enthalpy to the antigen binding (see, e.g., Makabe et al., 2008, Journal of Biological Chemistry, 283:1156-1166). Other CDR boundary definitions may not strictly follow one of the above methods, but still overlap with at least a portion of the Kabat CDRs. The boundaries of CDRs may be shortened or lengthened based on predictions or experimental results that a particular residue or group of residues does not significantly affect the antigen binding. As used herein, a CDR may refer to a CDR defined by any method known in the art, including combinations of methods. The correspondence between the various numbering schemes is well known to those skilled in the art, and examples are shown in Table 1 below.

TABLE 1

Relationships among CDR numbering schemes

| CDR | IMGT | Kabat | AbM | Chothia | Contact |
|---|---|---|---|---|---|
| HCDR1 | 27-38 | 31-35 | 26-35 | 26-32 | 30-35 |
| HCDR2 | 56-65 | 50-65 | 50-58 | 52-56 | 47-58 |
| HCDR3 | 105-117 | 95-102 | 95-102 | 95-102 | 93-101 |
| LCDR1 | 27-38 | 24-34 | 24-34 | 24-34 | 30-36 |
| LCDR2 | 56-65 | 50-56 | 50-56 | 50-56 | 46-55 |
| LCDR3 | 105-117 | 89-97 | 89-97 | 89-97 | 89-96 |

The CDR amino acid residues of the VL and VH regions of the antibody of the present disclosure accord with the known Kabat numbering scheme in terms of number and positions.

The antibody of the present disclosure may be polyclonal, monoclonal, xenogenic, allogeneic, syngeneic, or modified forms thereof, with the monoclonal antibody being particularly useful in various embodiments. Generally, the antibody of the present disclosure is a recombinant antibody.

The "recombinant" used herein generally refers to such products as a cell, a nucleic acid, a protein, or a vector, and indicates that the cell, the nucleic acid, the protein or the vector has been modified by the introduction of a heterologous nucleic acid or protein or the alteration of a native nucleic acid or protein. For example, recombinant cells express genes that are not found within the native (non-recombinant) cellular form or express native genes that are abnormally expressed, lowly expressed, or not expressed at all.

"Domain" of a polypeptide or protein refers to a folded protein structure that is capable of maintaining its tertiary structure independently of the rest of the protein. In general, a domain is responsible for a single functional property of a protein, and in many cases may be added, removed, or transferred to other proteins without loss of functions of the rest of the protein and/or the domain.

"Immunoglobulin domain" refers to a globular region of an antibody chain. Immunoglobulin domains are characterized by their maintenance of the folding feature of the antibody molecule.

"Immunoglobulin variable domain" refers to an immunoglobulin domain substantially consisting of four "framework regions", i.e., "framework region 1" or "FR1", "framework region 2" or "FR2", "framework region 3" or "FR3", and "framework region 4" or "FR4", and three "complementarity determining regions" or "CDRs", i.e., "complementarity determining region 1" or "CDR1", "complementarity determining region 2" or "CDR2", and "complementarity determining region 3" or "CDR3". Thus, the general structure or sequence of an immunoglobulin variable domain can be expressed as follows: FR1-CDR1-FR2-CDR2-FR3-CDR3-FR4. Immunoglobulin variable domains possess specificity for an antigen by virtue of having an antigen-binding site.

"Antibody framework (FR)" refers to a portion of a variable domain, which serves as a framework for the antigen-binding loops (CDRs) of the variable domain.

"Immunoglobulin single variable domain" is generally used to refer to an immunoglobulin variable domain (which may be a heavy or light chain domain, including a VH, VHH, or VL domain) that can form a functional antigen-binding site without interacting with other variable domains (e.g., without VH/VL interactions as are required between the VH and VL domains of conventional four-chain monoclonal antibodies). Examples of "immunoglobulin single variable domains" include nanobodies (including a VHH, humanized VHH, and/or camelized VH, e.g. a camelized human VH), IgNAR, domains, (single-domain) antibodies as VH domains or derived from VH domains (such as dAbs™) and (single-domain) antibodies as VL domains or derived from VL domains (such as dAbs™). Immunoglobulin single variable domains based on and/or derived from heavy chain variable domains (such as VH or VHH domains) are generally preferred. A specific example of an immunoglobulin single variable domain is a "VHH domain" (or simply "VHH") as defined below.

"VHH domain", also known as heavy chain single-domain antibody, VHH, VHH domain, VHH antibody fragment, VHH antibody, or nanobody, is a variable domain of an antigen-binding immunoglobulin known as a "heavy-chain antibody" (i.e., "an antibody devoid of light chains") (Hamers-Casterman C, Atarhouch T, Muyldermans S, Robinson G, Hamers C, Songa E B, Bendahman N, Hamers R., "Naturally occurring antibodies devoid of light chains"; Nature 363, 446-448 (1993)). The term "VHH domain" is used to distinguish said VHH from the VHs and VLs present in antibodies of the conventional four-peptide-chain structure. VHH domains specifically bind to epitopes without the need for additional antigen-binding domains (however, in antibodies of the conventional four-peptide-chain structure, epitopes are recognized by the VL domains together with the VH domains). The VHH domain is a small, stable and efficient antigen recognition unit formed by a single immunoglobulin domain. The terms "heavy-chain single-domain antibody", "VHH domain", "VHH", "Vim domain", "VHH antibody fragment", "VHH antibody", "Nanobody®" and "Nanobody® domain" ("Nanobody" is a trademark of Ablynx N.V., Ghent, Belgium) are used interchangeably. "VHH domains" include, but are not limited to, natural antibodies produced by camelids, antibodies produced by camelids and then humanized, or antibodies obtained by screening with phage display techniques. The total number of amino acid residues in a VHH domain will usually be in the range of 110 to 120, often between 112 and 115. However, it should be noted that smaller and longer sequences may also be suitable for the purposes described in the present disclosure. Methods for obtaining VHHs that bind to a particular antigen or epitope have been previously disclosed in the following documents: R. van der Linden et al., Journal of Immunological Methods, 240(2000) 185-195; Li et al., J Biol Chem., 287(2012) 13713-13721; Deffar et al., African Journal of Biotechnology Vol. 8(12), pp. 2645-2652, 17 Jun., 2009 and WO94/04678.

As is well known in the art for VH domains and VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Other numbering systems or numbering schemes for VHHs include Chothia, IMGT, and AbM.

"Humanized antibody", also known as a CDR-grafted antibody, refers to an antibody produced by grafting non-human CDR sequences into the framework of variable regions of a human antibody. Chimeric antibodies, due to their significant non-human protein content, can induce a strong immune response. This issue can be overcome by using humanized antibodies. To avoid the decrease in activity caused by the decrease in immunogenicity, the variable regions of a fully human antibody can be subjected to minimum reverse mutation to maintain activity. Examples of "humanization" include "humanization" of VHH domains derived from the family Camelidae by replacing one or more amino acid residues in the amino acid sequence of the original VHH sequence with one or more amino acid residues present at the corresponding positions in a VH domain of an antibody of the conventional four-peptide-chain structure (also referred to in the present disclosure as "sequence optimization"; in addition to humanization, "sequence optimization" may also encompass other modifications to the sequence by one or more mutations providing improved properties of the VHH, such as removal of potential post-translational modification sites). The humanized VHH domain may contain one or more fully human framework region sequences. In some specific embodiments, the human framework region sequence of IGHV3 may be contained. Another example of "humanization" includes an antibody produced by grafting mouse CDR sequences into a human antibody variable region framework, i.e., a different type of human germline antibody framework sequence. Therefore, the strong antibody variable antibody reaction induced by a large amount of heterologous protein components contained in the chimeric antibody can be overcome. Methods for humanization include, e.g., protein surface amino acid humanization (resurfacing) and universal framework grafting method for antibody humanization (CDR grafting to a universal framework), i.e., "grafting" CDRs onto other "frameworks" (including but not limited to human scaffolds or non-immunoglobulin scaffolds). Scaffolds and techniques suitable for such CDR grafting are known in the art. For example, germline DNA sequences of genes of the human heavy and light chain variable regions can be found in the "VBase" human species sequence database, as well as in Kabat, E. A. et al., 1991 Sequences of Proteins of Immunological Interest, 5th edition. The humanized antibody of the present disclosure also includes humanized antibodies formed by further affinity maturation of the CDRs by phage display. In addition, in order to avoid the decrease in activity caused by the decrease in immunogenicity, the framework region sequence in the human antibody variable region can be subjected to minimum reverse mutation or back mutation to maintain activity.

An "affinity-matured" antibody is an antibody that has one or more changes in one or more hypervariable regions (HVRs) that result in an improvement in the affinity of the antibody for the antigen as compared to the parent antibody. For example, an "affinity-matured" PD-1-binding protein or PD-1 antibody has one or more changes in one or more CDRs that result in an increase in the affinity for the antigen as compared to its parent antibody. Affinity-matured antibodies can be prepared, for example, by methods known in the art as described below: Marks et al., 1992, Biotechnology 10:779-783 or Barbas et al., 1994, Proc. Nat. Acad. Sci, USA 91:3809-3813; Shier et al., 1995, Gene 169:147-155; Yelton et al., 1995, Immunol. 155:1994-2004; Jackson et al., 1995, J. Immunol. 154(7):3310-9; Hawkins et al., 1992, J. MoI. Biol. 226(3):889896; KS Johnson and RE Hawkins, "Affinity maturation of antibodies using phage display", Oxford University Press 1996.

"Fully human antibody" includes antibodies having variable and constant regions derived from human germline immunoglobulin sequences. The fully human antibody of the present disclosure may include amino acid residues not encoded by human germline immunoglobulin sequences (e.g., mutations introduced by random or site-specific mutagenesis in vitro or by somatic mutations in vivo). "Fully human antibody" does not include "humanized antibodies".

Generally, "specific binding" or "selective binding" refers to the binding of a binding protein to an epitope on an antigen. The PD-1-binding protein, PD-1/PVRIG-binding protein, PD-1/TIGIT-binding protein, or PD-1/PVRIG/TIGIT-binding protein of the present disclosure will bind to the antigen to be bound (i.e., PD-1, PVRIG, and/or TIGIT) or an epitope thereof with a dissociation constant ($K_D$) of preferably $10^{-7}$ to $10^{-10}$ mol/L (M), more preferably $10^{-8}$ to $10^{-10}$ mol/L, and even more preferably $10^{-9}$ to $10^{-10}$ or less, and/or with an association constant (KA) of at least $10^{-7}$ M, preferably at least $10^{-8}$ M, more preferably at least $10^{-9}$ M, and more preferably at least $10^{-10}$ M, as measured in a Biacore, KinExA or Fortibio assay. Any $K_D$ value greater than $10^{-4}$ M is generally considered to indicate non-specific binding. Specific binding of a binding protein to an antigen or epitope can be measured in any suitable manner known, including, for example, surface plasmon resonance (SPR) assays, Scatchard assay, and/or competitive binding assay (e.g., radioimmunoassay (RIA), enzyme immunoassay (EIA), and sandwich competitive assay) described in the present disclosure.

"Epitope" refers to a site on an antigen to which an immunoglobulin or an antibody binds. An epitope may be formed from contiguous amino acids, or non-contiguous amino acids juxtaposed by tertiary folding of the protein. An epitope formed from contiguous amino acids is generally retained after exposure to a denaturing solvent, while an epitope formed by tertiary folding is generally lost after a denaturing solvent treatment. An epitope generally comprises, for example, at least 3-15 amino acids in a unique spatial conformation. Methods for determining the binding of an epitope to a given antibody are well known in the art and include an immunoblotting assay, an immunoprecipitation assay, and the like. Methods for determining the spatial conformation of an epitope include techniques in the art and techniques described in the present disclosure, such as X-ray crystallography and two-dimensional nuclear magnetic resonance.

"Binding affinity" or "affinity" is used herein as a measure of the strength of a non-covalent interaction between two molecules (e.g., an antibody or a portion thereof and an antigen). The binding affinity between two molecules can be quantified by determining the dissociation constant ($K_D$). $K_D$ can be determined by measuring the kinetics of complex formation and dissociation by using, for example, the surface plasmon resonance (SPR) method (Biacore). The rate constants corresponding to the association and dissociation of a monovalent complex are referred to as the association rate constant ka (or kon) and the dissociation rate constant kd (or koff), respectively. $K_D$ is related to ka and kd by the equation $K_D$=kd/ka. The value of the dissociation constant can be determined directly by well-known methods, and calculations can even be performed for complex mixtures by, for example, those methods described in Caceci et al (1984, Byte 9:340-362). For example, $K_D$ can be determined by using a dual filtration nitrocellulose filter binding assay such as that disclosed by Wong & Lohman (1993, Proc. Natl. Acad. Sci. USA 90:5428-5432). Other standard assays for evaluating the ability of an antibody to bind to a target antigen are known in the art and include, for example, ELISA, western blot, RIA, and flow cytometry, as well as other assays exemplified in the present disclosure. The binding kinetics and binding affinity of the antibody can also be evaluated by standard assays known in the art, such as surface plasmon resonance (SPR), for example, by using the Biacore™ system or KinExA. The binding affinities associated with different molecular interactions, e.g., the binding affinities of different antibodies for a given antigen, can be compared by comparing the $K_D$ values of antibody/antigen complexes. Similarly, the specificity of an interaction can be evaluated by determining and comparing the $K_D$ value for the interaction of interest (e.g., a specific interaction between an antibody and an antigen) with the $K_D$ value for an interaction not of interest (e.g., a control antibody known not to bind to PD-1).

"Conservative substitution" refers to a substitution with another amino acid residue having similar properties to the original amino acid residue. For example, lysine, arginine, and histidine have similar properties in that they have basic side chains, and aspartic acid and glutamic acid have similar properties in that they have acidic side chains. In addition, glycine, asparagine, glutamine, serine, threonine, tyrosine, cysteine, and tryptophan have similar properties in that they have uncharged polar side chains, and alanine, valine, leucine, threonine, isoleucine, proline, phenylalanine, and methionine have similar properties in that they have non-polar side chains. In addition, tyrosine, phenylalanine, tryptophan, and histidine have similar properties in that they have aromatic side chains. Thus, it will be apparent to those skilled in the art that even when an amino acid residue in a group exhibiting similar properties as described above is replaced, it will not exhibit a particular change in properties.

"Homology", "identity" or "sequence identity" refers to sequence similarity between two polynucleotide sequences or between two polypeptides. When positions in two compared sequences are occupied by identical nucleotides or amino acid monomers, e.g., if the position of each of two DNA molecules is occupied by an identical nucleotide, the molecules are homologous at that position. The homology percentage between two sequences is a function of the number of matching or homologous positions shared by the two sequences divided by the number of positions compared×100%. For example, if 6 out of 10 positions are matched or homologous when two sequences are optimally aligned, the two sequences are 60% homologous. Generally, when two sequences are aligned, a comparison is performed to obtain the maximum homology percentage.

"Nucleic acid" or "polynucleotide" are used interchangeably herein to refer to any DNA or RNA molecule, either single- or double-stranded, and, if single-stranded, the molecule of its complementary sequence, preferably a double-stranded DNA. A nucleic acid is "operably linked" when it is placed into a functional relationship with another nucleic acid sequence. For example, a promoter or enhancer is operably linked to a coding sequence if it affects the transcription of the coding sequence.

"Host cell" includes individual cells or cell cultures, which may be or have been the recipient of a vector for incorporation of a polynucleotide insert. The host cell includes progeny of a single host cell, and the progeny are not necessarily completely identical (in morphology or genomic DNA complement) to the parent cell due to natural, accidental or deliberate mutations. The host cell includes cells transfected and/or transformed in vivo with polynucleotides of the present disclosure. "Cell", "cell line", and "cell culture" are used interchangeably, and all such designations include their progeny. It should also be understood that their progeny may not be precisely identical in DNA content due to deliberate or unintentional mutations. The term includes mutant progeny that have the same function or biological activity as the cell selected in the original transformation.

"Inhibition" and "blocking" are used interchangeably and encompass both partial and complete inhibition/blocking. "Inhibition of growth" (e.g., involving cells) is intended to include any measurable reduction in cell growth.

"Arresting the growth of" or "growth inhibition" refers to inhibiting cell growth or proliferation.

"Proliferative disease" refers to a disorder associated with a certain degree of abnormal cell proliferation. In one embodiment, the proliferative disorder is cancer.

"Tumor" refers to all neoplastic cell growth and proliferation, whether malignant or benign, and all pre-cancerous and cancerous cells and tissues. "Cancer", "cancerous", "proliferative disorder", and "tumor" are not mutually exclusive when referred to in the present disclosure.

"Preventing cancer" or "prevention of cancer" refers to delaying, inhibiting, or preventing the onset of cancer in a subject in which the onset of oncogenesis or tumorigenesis has not been evidenced but a predisposition toward cancer has been identified, as determined by, for example, genetic screening or otherwise. The term also encompasses treating a subject having a premalignant disorder to stop the progression of, or cause regression of, the premalignant disorder towards malignancy.

"Giving", "administering" and "treating", when applied to animals, humans, experimental subjects, cells, tissues, organs, or biological fluid, refer to contact of an exogenous drug, a therapeutic agent, a diagnostic agent, or a composition with the animals, humans, subjects, cells, tissues, organs or biological fluid, e.g., therapeutic, pharmacokinetic, diagnostic, research, and experimental methods. The treatment of cells comprises contacting the reagent with the cells and contacting the reagent with fluid, where the fluid is in contact with the cells. "Giving", "administering", and "treating" also refer to treating, e.g., a cell, by a reagent, diagnosis, a binding composition, or by another cell in vitro and ex vivo. When applied to humans, veterinary or research subjects, they refer to therapeutic treatment, preventive or prophylactic measures, and research and diagnostic applications.

"Treating" or "treatment" refers to administering a therapeutic agent, such as a therapeutic agent comprising any binding protein of the present disclosure or a pharmaceutical composition thereof, either internally or externally, to a subject who has had, is suspected of having, or is predisposed to having one or more proliferative diseases or symptoms thereof on which the therapeutic agent is known to have a therapeutic effect. Typically, the therapeutic agent is administered in an amount effective to alleviate one or more symptoms of the disease in the subject or population being treated, whether by inducing regression of such symptoms or inhibiting the development of such symptoms into any clinically measurable degree. The amount of therapeutic agent effective to alleviate any particular symptom of the disease (also referred to as the "therapeutically effective amount") may vary depending on factors such as the disease state, age and weight of the subject, and the ability of the drug to produce a desired therapeutic effect in the subject. Whether a symptom of a disease has been alleviated can be evaluated by any clinical testing methods commonly used by doctors or other health care professionals to evaluate the severity or progression of the symptom. Although embodiments of the present disclosure (e.g., treatment methods or products) may be ineffective in alleviating symptoms of a disease of interest in a certain subject, they shall alleviate the symptoms of the disease of interest in a statistically significant number of subjects as determined by any statistical test method known in the art, such as the Student's t-test, Chi-square test, U-test by Mann and Whitney, Kruskal-Wallis test (H-test), Jonckheere-Terpstra test and Wilcoxon test.

"Effective amount" comprises an amount sufficient to ameliorate or prevent a symptom or sign of a medical disorder. An effective amount also refers to an amount sufficient to allow or facilitate diagnosis. The effective amount for a subject may vary depending on factors such as the disorder to be treated, the general health of the subject, the method and dose of administration, and the severity of side effects. An effective amount may be the maximum dose or administration regimen to avoid significant side effects or toxic effects. The subject of the present disclosure may be an animal or a human subject.

"Optional" or "optionally" means that the event or circumstance subsequently described may, but does not necessarily, occur and that the description includes instances where the event or circumstance occurs or does not occur. "And/or" should be taken as specific disclosure of each of the two specified features or components with or without the other. Thus, the term "and/or" as used in a phrase such as "A and/or B" in the present disclosure includes "A and B", "A or B", "A" (alone), and "B" (alone). Unless the context clearly requires otherwise, throughout the description and the claims, the words "comprise", "have", "include", and the like are to be construed in an inclusive sense as opposed to an exclusive or exhaustive sense; that is to say, in the sense of "including, but not limited to".

The "subject" or "patient" in the present disclosure refers to a mammal, particularly a primate, and particularly a human.

EXAMPLES

The present disclosure is further described below with reference to examples, but these examples are not intended to limit the scope of the present disclosure. Experimental procedures without specific conditions indicated in the examples or test examples are generally conducted according to conventional conditions, or according to conditions recommended by the manufacturer of the starting materials or commercial products. See Sambrook et al., Molecular Cloning: A Laboratory Manual, Cold Spring Harbor Laboratory Press; Current Protocols in Molecular Biology, Ausubel et al., Greene Publishing Association, Wiley Interscience, NY Reagents without specific origins indicated are commercially available conventional reagents.

Example 1. Screening, Preparation, and Functional Verification of Anti-PD-1 Nanobodies In this example, His-tagged human PD-1 was used as an immunizing antigen, and biotinylated human PD-1 and cynomolgus monkey PD-1 as screening antigens; the antigens were all purchased from AcroBiosystems.

Example 1-1. Screening and Preparation of Anti-PD-1 Nanobodies

1. Sequences and Preparation of Immunizing and Screening Antigens

TABLE 2

PD-1 antigens for immunizing alpacas and screening

| Antigen | Cat. No. | Starting and ending amino acids | Accession No. |
|---|---|---|---|
| Human PD-1 protein (His Tag) | PD1-H5221 | Leu25-Gln167 | # NP_005009.2 |
| Biotinylated human PD-1 protein (Avitag -His Tag) | PD1-H82E4 | | # Q15116-1 |
| Biotinylated monkey PD-1 protein (Avitag -His Tag) | PD1-C82E6 | | # B0LAJ3 |

The sequence of human PD-1 protein (NP_005009.2) is shown below, with the sequence of the extracellular region underlined—it starts with the amino acid Leu25 and ends with the amino acid Gln167.

>The amino acid sequence of human PD-1 (SEQ ID NO: 1)
MQIPQAPWPVVWAVLQLGWRPGWFLDSPDRPWNPPTFSPALLVVTEGDNA
TFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAE
VPTAHPSPSPRPAGQFQTLVVGVVGGLLGSLVLLVWVLAVICSRAARGTI
GARRTGQPLKEDPSAVPVFSVDYGELDFQWREKTPEPPVPCVPEQTEYAT
IVFPSGMGTSSPARRGSADGPRSAQPLRPEDGHCSWPL.

2. Alpaca Immunization, Nanobody Yeast Display Library Construction, and Antibody Screening 1) Alpaca Immunization Two healthy alpacas were immunized. At day 0, the first immunization was performed: 0.25 mg of human PD-1 antigen was well mixed with 1 mL of complete Freund's adjuvant (CFA), and the mixture was injected subcutaneously. At days 21, 42, and 63, 0.125 mg of human PD-1 antigen was well mixed with 1 mL of incomplete Freund's adjuvant (IFA), and the mixture was injected subcutaneously. 10 mL, 50 mL, and 50 mL of blood were collected at day 28, day 49, and day 70, respectively. The serum titer was measured, and alpaca peripheral lymphocytes up to the library construction standard were used to construct a nanobody yeast display library.

2) Yeast Library Construction

After the third and fourth immunizations of the 2 alpacas, 50 mL peripheral blood samples were taken. PBMCs were separated from the peripheral blood samples, and RNA was extracted from the PBMCs and reverse-transcribed to obtain total cDNA. The cDNA was used as a template for the first round of nested PCR. After two rounds of nested PCR amplification, the fragment products of the second round of nested PCR were ligated to a yeast library vector (the yeast library vector pYDN3), and the ligation products were introduced into yeast competent cells by electroporation. Colony PCR was used to verify the insertion rate and library diversity. The results of analysis based on the number of library transformants, the library insertion rate, and the library diversity and sequencing show that one alpaca's library capacity was $9.28\times10^7$ and the other alpaca's was $1.54\times10^8$.

3) Nanobody (VHH) Screening

The yeast display system was screened for antibodies using flow cytometry (FACS) sorting, library screening, and identification. Two rounds of sorting were performed. In the first round, enrichment was performed using biotinylated human PD-1 protein (Avitag-His Tag) magnetic beads. In the second round, sorting was performed using a biotinylated monkey PD-1 protein (His, Avitag) flow cytometry sorter (flow cytometry antibody: mouse anti-HA tag Dylight 488; streptavidin Dylight 650). After the two rounds of sorting, monoclonal identification, sequencing, and sequence analysis were performed, and 18 unique VHH sequences that cross-bind to human and monkey PD-1 antigens were obtained. The sequences A6 and A17 among them are shown below.

>The variable region of A6 (SEQ ID NO: 2)
EVQLVESGGGLVQAGGSLRLSCAVSGRTFSSAAMGWFRQAPGKEREFVAA
ISWSFGSTYYADSVKGRFTISRDNAKNTVYLQMNSLKPEDTAVYYCAADP
SIETMGGGWDYWGQGTQVTVSS >The variable region of A17 (SEQ ID NO: 3)
EVQVVESGGGLVQPGGSLRLSCVASGLTFSDYSMSWYRQAPGKERELVAI
ISGSGVIAHYVDSVKGRFTISRDNAKSTVYLQMVSLKPEDRGVYYCRAVS
DWDDYWGQGTQVTVSS.

TABLE 3

The CDRs of anti-PD-1 nanobodies (Kabat numbering scheme)

| No. | | CDR sequences |
|---|---|---|
| A6 | CDR1 | SAAMG (SEQ ID NO: 4) |
| | CDR2 | ISWSFGSTYYADSVKG (SEQ ID NO: 5) |
| | CDR3 | DPSIETMGGGWDY (SEQ ID NO: 6) |
| A17 | CDR1 | DYSMS (SEQ ID NO: 7) |
| | CDR2 | IISGSGVIAHYVDSVKG (SEQ ID NO: 8) |
| | CDR3 | VSDWDDY (SEQ ID NO: 9) |

The above sequences were each linked to a human IgG4 Fc (comprising a hinge region and S228P, according to the Eu numbering scheme) fragment to construct VHH-Fc antibodies. Plasmids were constructed and transiently transfected into HEK293 cells. The antibodies were expressed and purified using a protein A column. The column was washed with PBS, and elution was performed with a 0.1 M glycine buffer, pH 2.5. The antibodies were transferred to a pH 7.4 PBS buffer by dialysis. The sequences of the human IgG4 Fc (comprising a hinge region) and the VHH-Fc antibodies based on A6 and A17 are as follows:

>hIgG4 (SEQ ID NO: 10)
ESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK;

>A6_hIgG4 (SEQ ID NO: 11)
EVQLVESGGGLVQAGGSLRLSCAVSGRTFSSAAMGWFRQAPGKEREFVAA
ISWSFGSTYYADSVKGRFTISRDNAKNTVYLQMNSLKPEDTAVYYCAADP
SIETMGGGWDYWGQGTQVTVSSESKYGPPCPPCPAPEFLGGPSVFLFPPK
PKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLG
K;

-continued

```
>A17_hIgG4
                                          (SEQ ID NO: 12)
EVQVVESGGGLVQPGGSLRLSCVASGLTFSDYSMSWYRQAPGKERELVAI
ISGSGVIAHYVDSVKGRFTISRDNAKSTVYLQMVSLKPEDRGVYYCRAVS
DWDDYWGQGTQVTVSSESKYGPPCPPCPAPEFLGGPSVFLFPPKPKDTLM
ISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK.
```

Example 1-2. Verification of Affinity of Anti-PD-1 Nanobodies for Antigen PD-1

1. ELISA

The protein human PD-1 (his tag) was dissolved in PBS to form a 1 μg/mL solution, and the solution was added to a 96-well plate at 100 μL/well. The plate was coated with the antigen overnight at 4° C. The plate was washed with PBST (PBS+0.05% tween20) solution three times. PBST/1% BSA solution was added, and the plate was incubated at 37° C. for 1 h for blocking. After three washes with PBST solution, different concentrations of the candidate PD-1 VHH-Fc antibodies (diluted with PBST/1% BSA solution) were added, and the plate was incubated at 37° C. for 1.5 h. The plate was washed with PBST solution three times. 100 μL of HRP-conjugated anti-human IgG4 Fc secondary antibody (Thermo) solution was added, and the plate was incubated at 37° C. for 1 h. After three washes with PBST solution, TMB solution was added at 100 μL/well. After 5 min of reaction at room temperature, 50 μL of stop solution was added. Then 450 nM values were measured using a microplate reader, and $EC_{50}$ was calculated.

According to the results shown in Table 4, both A6 hIgG4 and A17_hIgG4 have relatively strong binding affinity for PD-1 antigen.

TABLE 4

The $EC_{50}$ values of anti-PD-1 nanobodies measured by ELISA

| Antibody No. | $EC_{50}$ (nM) |
|---|---|
| A6_hIgG4 | 0.08605 |
| A17_hIgG4 | 0.06099 |

2. FACS

To measure the ability of the anti-PD-1 nanobodies to bind to PD-1 expressed on the cell membrane, different concentrations of the candidate anti-PD-1 VHH-Fc antibodies were added to $10^5$/well Jurkat cells overexpressing human PD-1 (Cat: J1250, Promega). The plate was incubated at room temperature for 20 min and then washed with PBS twice. 100 μL of anti-human IgG Fc fluorescent secondary antibody (Biolegend) was added. The plate was incubated at room temperature for 20 min and then washed with PBS twice, and the cells were resuspended in 250 μL of PBS. Fluorescence signals were detected by FACS, and $EC_{50}$ was calculated.

Pembrolizumab (purchased from Biointron) was used as a control. The results are shown in Table 5. The $EC_{50}$ value of A17_hIgG4 is 0.3568 nM, which is significantly better than those of the other antibodies obtained from the same screening (results not shown).

TABLE 5

The $EC_{50}$ values of anti-PD-1 nanobodies binding to cell surface PD-1 measured by FACS

| Antibody No. | $EC_{50}$ (nM) |
|---|---|
| A6_hIgG4 | 1.09 |
| A17_hIgG4 | 0.3568 |
| Pembrolizumab | 0.2169 |

Example 1-3. Modification of Anti-PD-1 Nanobody Sequences

1. Humanization and Back Mutation of Anti-PD-1 Nanobodies

Antibody humanization was performed by CDR grafting. Through the website of IMGT or NCBI, the parent anti-PD-1 antibodies were aligned to fully human germline genes in the IMGT or NCBI/igblast database, and the human germline gene IGHV 3-23 (IGHV3-23*01; IGHV3-23*04) that was highly homologous with the PD-1 nanobodies was selected as a humanization template. CDRs were grafted, 4 key residues (Y37, E44, R45, and L47) in FR2 of the nanobodies were kept, and the key core residues close to the CDRs and the Vernier zone residues that interact with the CDRs were back-mutated; humanized antibodies A17h1, A17h2, A17h3, and A6h1 were obtained.

```
>The variable region of A17h1
                                          (SEQ ID NO: 13)
EVQLQESGGGLVQPGGSLRLSCTASGLTFSDYSMSWYRQAPGKGRELVAI
ISGSGVIAHYVDSVKGRFTISRDNSKNTVYLQMRSLTPEDRAVYYCRAVS
DWDDYWGQGTQVTVSS;

>The variable region of A17h2
                                          (SEQ ID NO: 14)
EVQLVESGGGLVQPGGSLRLSCAASGLTFSDYSMSWVRQAPGKGLEWVAI
ISGSGVIAHYVDSVKGRFTISRDNSKNTVYLQMNSLRAEDTAVYYCRAVS
DWDDYWGQGTQVTVSS;

>The variable region of A17h3
                                          (SEQ ID NO: 15)
EVQLVESGGGLVQPGGSLRLSCAASGLTFSDYSMSWVRQAPGKGLEWVAI
ISGSGVIAHYVDSVKGRFTISRDNSKNTVYLQMNSLRAEDTAVYYCRAVS
DWDEYWGQGTQVTVSS;

> The variable region of A6h1
                                          (SEQ ID NO: 16)
EVQLLESGGGLVQAGGSLRLSCATSGRTFSSAAMGWFRQAPGKGLEWVAA
ISWSFGSTYYADSVKGRFTISRDNSKNTVYLQMNSLRPEDTAVYYCAADP
SIETMGGGWDYWGQGTQVTVSS.
```

2. TCE (T Cell Epitope)-Removing, Antibody Deamidation-Reducing, and Antibody Isomerization-Reducing Modifications To reduce the potential immunogenic risk of the antibodies, TCE-removing modifications were performed. To improve the druggability of the antibodies, antibody deamidation and antibody isomerization site modifications were performed. The following sequences were obtained:

>The variable region of A17m01

(SEQ ID NO: 17)

EVQLQESGGGLVQPGGSLRLSCTASGLTFSDYSMSWYRQAPGKGRELVAI

ISGSGVIAHYVDSVKGRFTISRDNAKNTVYLQMRSLTPEDRAVYYCRAVS

DWDDYWGQGTQVTVSS

>The variable region of A17m02

(SEQ ID NO: 18)

EVQLQESGGGLVQPGGSLRLSCTASGLTFSDYSMSWYRQAPGKGRELVAI

ISGSGVITHYVDSVKGRFTISRDNSKNTVYLQMRSLTPEDRAVYYCRAVS

DWDDYWGQGTQVTVSS

>The variable region of A17m03

(SEQ ID NO: 19)

EVQLQESGGGLVQPGGSLRLSCTASGLTFSDYSMSWYRQAPGKGRELVAI

ISGSGGIAHYVDSVKGRFTISRDNSKNTVYLQMRSLTPEDRAVYYCRAVS

DWDDYWGQGTQVTVSS

>The variable region of A17m04

(SEQ ID NO: 20)

EVQLQESGGGLVQPGGSLRLSCTASGLTFSDYSMSWYRQAPGKGRELVAI

ISGSGVSAHYVDSVKGRFTISRDNSKNTVYLQMRSLTPEDRAVYYCRAVS

DWDDYWGQGTQVTVSS

>The variable region of A17m05

(SEQ ID NO: 21)

EVQLQESGGGLVQPGGSLRLSCTASGLTFSDYSMSWYRQAPGKGRELVAI

ISGSGVIAHYVDSVKGRFTISRDNSKNTVYLQMRSLTPEDRAVYYCRAVS

DWEDYWGQGTQVTVSS

>The variable region of A17m06

(SEQ ID NO: 22)

EVQLQESGGGLVQPGGSLRLSCTASGLTFSDYSMSWYRQAPGKGRELVAI

ISGSGVIAHYVDSVKGRFTISRDNSKNTVYLQMRSLTPEDRAVYYCRAVS

DWDEYWGQGTQVTVSS

>The variable region of A17m07

(SEQ ID NO: 23)

EVQLQESGGGLVQPGGSLRLSCTASGLTFSDYSMSWYRQAPGKGRELVAI

ISGSGVIAHYVDSVKGRFTISRDNAKNTVYLQMRSLTPEDRAVYYCRAVS

DWEDYWGQGTQVTVSS

>The variable region of A17m08

(SEQ ID NO: 24)

EVQLQESGGGLVQPGGSLRLSCTASGLTFSDYSMSWYRQAPGKGRELVAI

ISGSGVIAHYVDSVKGRFTISRDNAKNTVYLQMRSLTPEDRAVYYCRAVS

DWDEYWGQGTQVTVSS

>The variable region of A17m09

(SEQ ID NO: 25)

EVQLQESGGGLVQPGGSLRLSCTASGLTFSDYSMSWYRQAPGKGRELVAI

ISGSGVITHYVDSVKGRFTISRDNAKNTVYLQMRSLTPEDRAVYYCRAVS

DWEDYWGQGTQVTVSS

>The variable region of A17m10

(SEQ ID NO: 26)

EVQLQESGGGLVQPGGSLRLSCTASGLTFSDYSMSWYRQAPGKGRELVAI

ISGSGVITHYVDSVKGRFTISRDNAKNTVYLQMRSLTPEDRAVYYCRAVS

DWDEYWGQGTQVTVSS

-continued

> The variable region of A17m11

(SEQ ID NO: 27)

EVQLQESGGGLVQPGGSLRLSCTASGLTFSDYSMSWYRQAPGKGRELVAI

ISGSGGIAHYVDSVKGRFTISRDNAKNTVYLQMRSLTPEDRAVYYCRAVS

DWEDYWGQGTQVTVSS

>The variable region of A17m12

(SEQ ID NO: 28)

EVQLQESGGGLVQPGGSLRLSCTASGLTFSDYSMSWYRQAPGKGRELVAI

ISGSGGIAHYVDSVKGRFTISRDNAKNTVYLQMRSLTPEDRAVYYCRAVS

DWDEYWGQGTQVTVSS

>The variable region of A17m13

(SEQ ID NO: 29)

EVQLQESGGGLVQPGGSLRLSCTASGLTFSDYSMSWYRQAPGKGRELVAI

ISGSGVSAHYVDSVKGRFTISRDNAKNTVYLQMRSLTPEDRAVYYCRAVS

DWEDYWGQGTQVTVSS

>The variable region of A17m14

(SEQ ID NO: 30)

EVQLQESGGGLVQPGGSLRLSCTASGLTFSDYSMSWYRQAPGKGRELVAI

ISGSGVSAHYVDSVKGRFTISRDNAKNTVYLQMRSLTPEDRAVYYCRAVS

DWDEYWGQGTQVTVSS

> The variable region of A17m15

(SEQ ID NO: 31)

EVQLQESGGGLVQPGGSLRLSCTASGLTFSDYSMSWYRQAPGKGRELVAI

ISGSGGITHYVDSVKGRFTISRDNAKNTVYLQMRSLTPEDRAVYYCRAVS

DWEDYWGQGTQVTVSS.

A17m09 was selected, and the antibody sequence was further subjected to a germlining modification to improve the degree of humanization; the following sequences were obtained:

>The variable region of A17m0901

(SEQ ID NO: 32)

EVQLVESGGGLVQPGGSLRLSCAASGFTFSDYSMSWYRQAPGKGRELVAI

ISGSGVITHYVDSVKGRFTISRDNAKNTLYLQMRSLRAEDTAVYYCRAVS

DWEDYWGQGTQVTVSS

>The variable region of A17m0902

(SEQ ID NO: 33)

EVQLVESGGGLVQPGGSLRLSCAASGLTFSDYSMSWYRQAPGKGRELVAI

ISGSGVITHYVDSVKGRFTISRDNAKNTLYLQMRSLRAEDTAVYYCRAVS

DWEDYWGQGTQVTVSS

>The variable region of A17m0903

(SEQ ID NO: 34)

EVQLVESGGGLVQPGGSLRLSCAASGLTFSDYSMSWYRQAPGKGRELVAI

ISGSGVITHYVDSVKGRFTISRDNAKNTVYLQMRSLRAEDTAVYYCRAVS

DWEDYWGQGTQVTVSS

>The variable region of A17m0905

(SEQ ID NO: 35)

EVQLVESGGGLVQPGGSLRLSCAASGLTFSDYSMSWYRQAPGKGRELVAI

ISGSGVITHYVDSVKGRFTISRDNAKNTVYLQMRSLRAEDRAVYYCRAVS

DWEDYWGQGTQVTVSS.

That is, A17 of the present disclosure has the following general sequence:

```
                                        (SEQ ID NO: 7)
            CDR1: DYSMS
```

CDR2: IISGSG$X_1X_2X_3$HYVDSVKG, wherein $X_1$ is selected from the group consisting of V and G; $X_2$ is selected from the group consisting of I and S; and $X_3$ is selected from the group consisting of T and A (SEQ ID NO: 36)

CDR3: VSDW$X_4X_5$Y, wherein $X_4$ is selected from the group consisting of D and E, and $X_5$ is selected from the group consisting of D and E (SEQ ID NO: 37).

Specifically, the CDR2 may be:

```
                                        (SEQ ID NO: 8)
IISGSGVIAHYVDSVKG

                                       (SEQ ID NO: 38)
IISGSGVITHYVDSVKG

                                       (SEQ ID NO: 39)
IISGSGGIAHYVDSVKG

                                       (SEQ ID NO: 40)
IISGSGVSAHYVDSVKG

                                      (SEQ ID NO: 101)
IISGSGGITHYVDSVKG

Specifically, the CDR3 may be:
                                        (SEQ ID NO: 9)
VSDWDDY

                                       (SEQ ID NO: 41)
VSDWEDY

                                       (SEQ ID NO: 42)
VSDWDEY.
```

Example 1-4. PD-1/PD-L1 Reporter Gene System Test of Blocking of PD-L1 Binding to PD-1 by Anti-PD-1 Nanobodies The biological activity function of the anti-PD-1 antibodies at the cellular level can be measured using the PD-1/PD-L1 NFAT gene reporter system (Cat: J1250, Promega). The system consists of two genetically engineered cell lines: a PD-1-overexpressing effector cell Jurkat (containing NFAT reporter gene luciferase) and a PD-L1-overexpressing antigen-presenting cell CHO-K1 cell. When the two cells are co-cultured, the interaction of PD-1/PD-L1 inhibits TCR-mediated NFAT activation and thereby inhibits the expression of NFAT reporter gene luciferase. When the PD-1/PD-L1 interaction is disrupted, TCR activation induces luciferase expression through the NFAT pathway. By adding Bio-Glo reagent and using a luminometer to quantitatively measure fluorescence, the extent of effector cell activation and the biological activity of an antibody can be measured.

CHO-K1 cells overexpressing PD-L1 were diluted to $4\times10^5$/mL and added to a 96-well plate at 100 μL/well, and the plate was incubated overnight. After the medium was pipetted off, 40 μL of $1.25\times10^6$/mL PD-1 Jurkat cells was added rapidly, along with 40 μL of anti-PD-1 nanobody solutions (diluted with 1640+2% FBS solution) with different concentrations. The plate was incubated at 37° C. for 6 h and cooled to room temperature. Bright-glo reagent (Cat: E2620, promega) was added at 40 μL/well. The plate was shaken in the dark at 350 rpm for 5 min and left to stand in the dark at room temperature for 5 min. Then fluorescence values were measured using a microplate reader, and $IC_{50}$ was calculated.

Pembrolizumab and hIgG4 isotype were used as controls. As shown in FIG. 1A and Table 6, the biologically functional activity $IC_{50}$ value of A17_hIgG4 is 1.199 nM, which is significantly better than those of the other antibodies obtained from the same screening in the present disclosure (for example, 7.62 for A3_hIgG4, and 3.208 for A13_hIgG4; the sequences of A3_hIgG4 and A13 hIgG4 are not shown).

TABLE 6

The activity $IC_{50}$ values of the anti-PD-1 nanobodies, as measured using the PD-1/PD-L1 NFAT reporter gene system

| Antibody No. | $IC_{50}$ (nM) |
|---|---|
| A6_hIgG4 | 1.354 |
| A17_hIgG4 | 1.199 |
| Pembrolizumab | 0.5126 |
| hIgG4 | — |

Figure 1B:
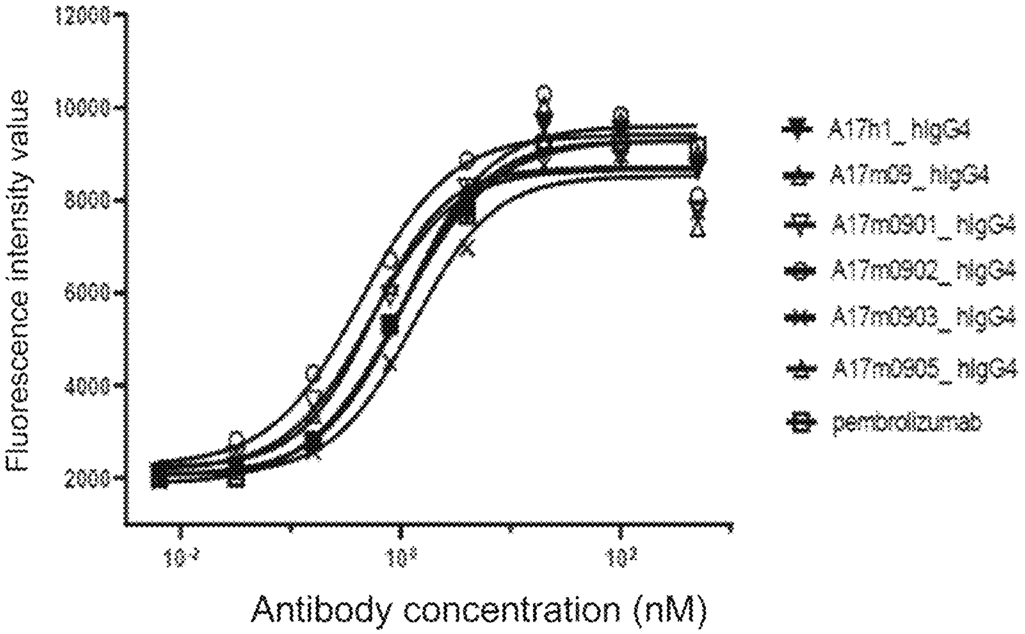

Using the above method, the humanized anti-PD-1 nanobodies were functionally verified. Referring to FIG. 1B and Table 7, the $IC_{50}$ activity of A17h1_hIgG4 is similar to that of the positive antibody pembrolizumab. Among the candidate molecules with modified sequences, the antibodies A17m0901_hIgG4 and A17m0902_hIgG4 have biological activity $IC_{50}$ values of 0.5307 nM and 0.4352 nM, respectively, which are better than that of pembrolizumab.

TABLE 7

The activity $IC_{50}$ of the modified anti-PD-1 nanobodies, as measured using the PD-1/PD-L1 NFAT reporter gene system

| Antibody No. | $IC_{50}$ (nM) |
|---|---|
| A17h1_hIgG4 | 1.039 |
| A17m09_hIgG4 | 1.083 |
| A17m0901_hIgG4 | 0.5307 |
| A17m0902_hIgG4 | 0.4352 |
| A17m0903_hIgG4 | 1.284 |
| A17m0905_hIgG4 | 0.5588 |
| Pembrolizumab | 0.9756 |

Example 1-5. Verification of Binding Affinity of Modified Anti-PD-1 Nanobodies for Antigen PD-1

The affinities of the anti-PD-1 nanobodies for PD-1 antigen were measured with a Biacore 8 k (GE Healthcare) instrument using surface plasmon resonance (SPR). In the experiment, a CM5 sensor chip was used, and HBS-EP+ buffer (10 mM HEPES, 150 mM NaCl, 3 mM EDTA, 0.05% surfactant P20) was used as a mobile phase. A 30 μg/mL solution of anti-human IgG (Fc) antibody was prepared in 10 mM sodium acetate buffer (pH 5.0), and the Immobilization program was selected to automatically perform anti-human IgG (Fc) antibody channel amino coupling immobilization. The test antibodies were separately diluted in HBS-EP+ buffer solution as ligands and captured using the anti-human IgG (Fc) antibody on the chip channels. The human or cynomolgus monkey PD-1 antigen protein (Sino Biological, 10377-H08H; 90311-C08H) was used as an analyte, serially diluted 2-fold with HBS-EP+buffer solution, and made to flow through the experimental and reference channels at a flow rate of 30 μL/min. Binding was allowed for 1 min and dissociation for 15 min. The regeneration buffer 10 mM Glycine pH 1.5 (GE Healthcare, BR-1003-54) was made to flow at a flow rate of 10 μL/min for 30 s. The binding rate Ka, the dissociation rate Kd, and the dissociation constant (i.e., affinity $K_D$) were calculated. The results are shown in Tables 8 and 9.

TABLE 8

SPR affinity data for the anti-PD-1 nanobodies binding to human PD-1 antigen

| Antibody No. | ka (1/Ms) | Kd (1/s) | $K_D$ (M) |
|---|---|---|---|
| A17h1_hIgG4 | 4.30E+05 | 8.68E−04 | 2.02E−09 |
| A17m09_hIgG4 | 4.58E+05 | 1.63E−03 | 3.56E−09 |
| A17m0901_hIgG4 | 2.97E+05 | 1.92E−03 | 6.44E−09 |
| A17m0902_hIgG4 | 2.91E+05 | 1.77E−03 | 6.09E−09 |
| Pembrolizumab | 1.25E+06 | 3.89E−03 | 3.11E−09 |

TABLE 9

SPR affinity data for the anti-PD-1 nanobodies binding to cynomolgus monkey PD-1 antigen

| Antibody No. | ka (1/Ms) | Kd (1/s) | $K_D$ (M) |
|---|---|---|---|
| A17h1_hIgG4 | 4.44E+05 | 8.07E−04 | 1.82E−09 |
| A17m09_hIgG4 | 4.81E+05 | 8.43E−04 | 1.75E−09 |
| A17m0901_hIgG4 | 3.40E+05 | 1.13E−03 | 3.32E−09 |
| A17m0902_hIgG4 | 3.28E+05 | 1.08E−03 | 3.28E−09 |
| Pembrolizumab | 1.31E+06 | 1.15E−03 | 8.82E−10 |

The results of binding to human PD-1 antigen show that the humanized antibody A17h1_hIgG4 and the subsequently modified, optimized antibodies A17m09_hIgG4, A17m0901_hIgG4, and A17m0902_hIgG4 have similar $K_D$ values to pembrolizumab. A17h1_hIgG4, A17m09_hIgG4, A17m0901_hIgG4, and A17m0902_hIgG4 all showed smaller dissociation rates than pembrolizumab. The antibodies A17h1_hIgG4, A17m09_hIgG4, A17m0901_hIgG4, and A17m0902_hIgG4 cross-bound to monkey PD-1, and the affinities of the antibodies for human and monkey PD-1 are similar.

Example 1-6. DC:T Mix Lymphocyte Reaction (MLR) Test of In Vitro Efficacy of Modified Anti-PD-1 Nanobodies Co-culture of mature dendritic cells (DCs) with allogeneic T cells can activate T cells and promote cytokine secretion by T cells. This process is inhibited by PD-1/PD-L1 signals, and an anti-PD-1 antibody can be used to remove the inhibition and promote T cell activation. Thus, a DC:T mix lymphocyte reaction experiment can be used to test the in vitro efficacy of the anti-PD-1 antibody.

Mononuclear cells were sorted from fresh peripheral blood (PBMCs) of a healthy person using a sorting kit (cat: 19359, stemcell). After seven days of culture using a DC induction kit (cat: 10985, stemcell), the mononuclear cells were induced to differentiate into mature DCs. Then allogeneic T cells were sorted from fresh PBMCs of another healthy person using a sorting kit (cat: 17951, stemcell). 5000 mature DCs were co-cultured with 50,000 allogeneic T cells, and a candidate antibody was added at a corresponding concentration. After six days of co-culture, the cell supernatant was collected and assayed for IFN-γ concentration using a Cisbio-HTRF IFN-γ assay kit (Cat: 62HIFNG-PEH, Perkinelmer), and $EC_{50}$ was calculated.

Figure 2:
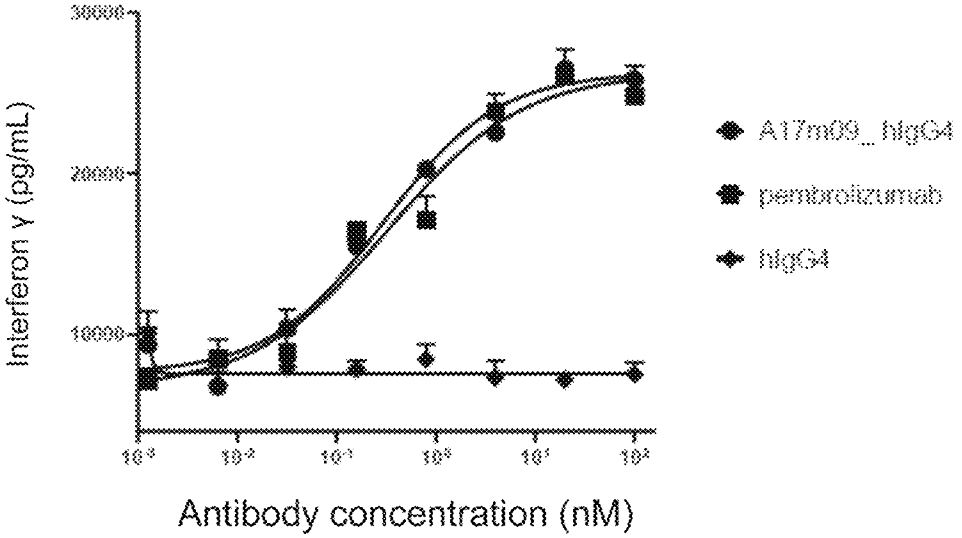
FIG. 2 shows the measurement, through the release of cytokines in a DC:T cell mix lymphocyte reaction, of the extent to which A17m09_hIgG4 activates T cells, wherein pembrolizumab is used as a positive control and hIgG4 as a negative control.

As shown in FIG. 2, A17m09_hIgG4 exhibited substantially the same in vitro efficacy as pembrolizumab in the MLR experiment. The $EC_{50}$ of A17m09_hIgG4 is 0.2931 nM, and the $EC_{50}$ of pembrolizumab is 0.3271 nM.

Example 1-7. Inhibition of Tumor Growth in Colon Cancer Mouse Model by Anti-PD-1 Nanobodies In this example, the in vivo anti-tumor efficacy of the anti-PD-1 antibodies was verified using an MC38 tumor model of humanized PD-1 C57BL/6 mice.

The MC38 mouse colon cancer cell line was cultured with DMEM medium (10% FBS), and $5\times10^5$ MC38 cells were subcutaneously inoculated into humanized PD-1 C57BL/6 female mice (GemPharmatech). When the mean tumor volume of the mice reached about 80 $mm^3$, the mice were randomized into groups of 8 and administered intraperitoneal injections of antibodies or controls. Tumor volume and body weight were measured twice a week, and data were recorded. The experimental groups and administration regimen are shown in Table 10. Given that the molecular weight of A17m09_hIgG4 is about 75 kDa, which is only half of the normal IgG molecular weight, its dose was set to be half of that of pembrolizumab to achieve an equimolar dose.

Figure 3A:
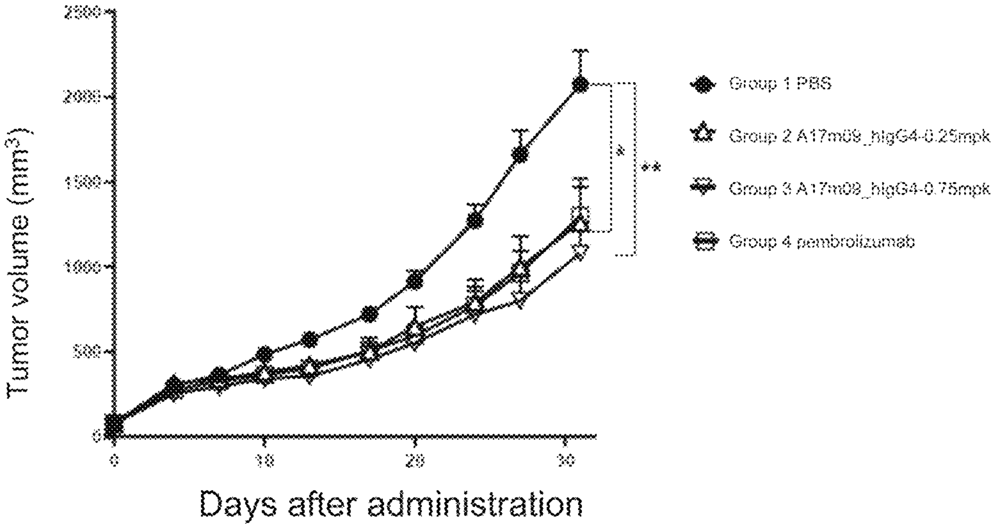
FIGS. 3A to 3B show the in vivo efficacy of A17m09_hIgG4 in inhibiting the growth of mouse MC38 colon cancer tumors.
Figure 3B:
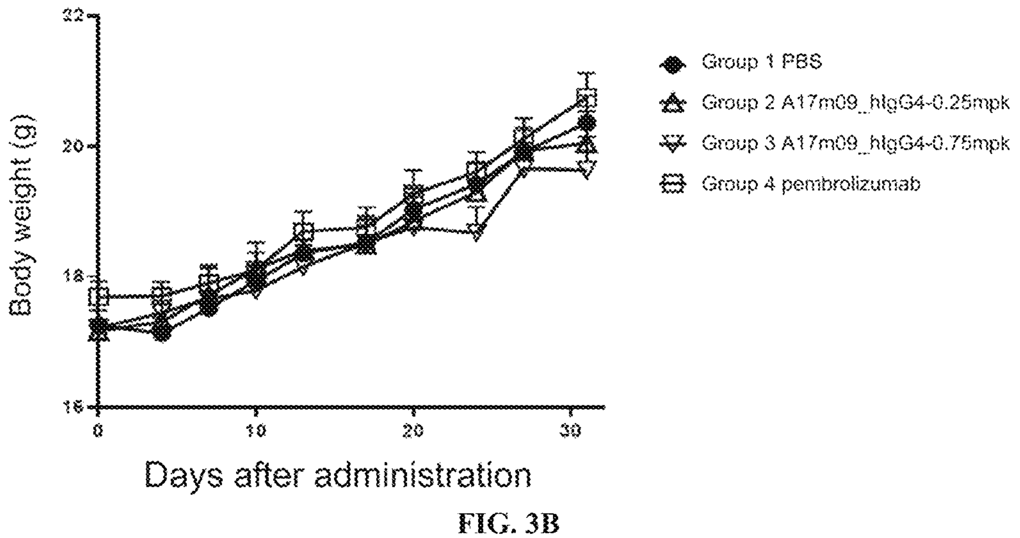

As shown in FIGS. 3A and 3B, A17m09_hIgG4 exhibited the same in vivo anti-tumor efficacy as pembrolizumab at the same equimolar dose. Tumor volumes and tumor inhibition rates are shown in Table 11.

TABLE 10

The experimental groups of mice and the administration regimen

| Group | Drug or control | Dose (mg/kg) | Route of administration | Frequency of administration |
|---|---|---|---|---|
| Group 1 | PBS | — | i.p. | BIW*7 |
| Group 2 | A17m09_hIgG4 | 0.25 | | |
| Group 3 | A17m09_hIgG4 | 0.75 | | |
| Group 4 | Pembrolizumab | 0.5 | | |

TABLE 11

Tumor volumes and tumor inhibition rates in mice

| | | Tumor volume/$mm^3$ (mean ± SEM) | | Tumor inhibition rate | |
|---|---|---|---|---|---|
| Group | Drug or control | Day 0 | Day 31 | Day 31 | P value |
| Group 1 | PBS | 79 ± 4 | 2074 ± 198 | / | / |
| Group 2 | A17m09_hIgG4 (0.25 mg/kg) | 79 ± 4 | 1261 ± 260 | 39% | 0.0263 |
| Group 3 | A17m09_hIgG4 (0.75 mg/kg) | 78 ± 3 | 1078 ± 186 | 48% | 0.0026 |
| Group 4 | Pembrolizumab (0.5 mg/kg) | 78 ± 3 | 1300 ± 174 | 37% | 0.0109 |

Note: i.p.: intraperitoneal injection; BIW*7: 2 times weekly, 7 injections in total; *P<0.05, P<0.01, and *P<0.001 are thought to indicate significant differences compared to the control group)

Example 2. Anti-PVRIG/TIGIT Bispecific Antibodies

In this example, the his-tagged human PVRIG (h-PVRIG-his) recombinant protein, mouse IgG2a Fc-tagged human PVRIG (h-PVRIG-mIgG2a Fc) recombinant protein, and human IgG1 Fc-tagged mouse PVRIG (m-PVRIG-hIgG1 Fc) were purchased from Acrobiosystems. The his-tagged PVRL2 was purchased from AcroBiosystem (PV2-H52E2).

Example 2-1. Screening and Preparation of Anti-PVRIG Nanobodies

1. Sequences and Preparation of Immunizing and Screening Antigens

TABLE 12

The amino acid sequences of recombinant proteins

| Name | Start and end of amino acid sequence | Genbank accession No. |
|---|---|---|
| h-PVRIG-his | Thr41-Asp171 | Q6DKI7-1 |
| h-PVRIG-mIgG2a Fc | Thr41-Asp171 | Q6DKI7-1 |
| m-PVRIG-hIgG1 Fc | Ser35-Asp165 | A0A1B0GS01-1 |

The sequence of the his-tagged cynomolgus monkey PVRIG (cyno-PVRIG-his) recombinant protein is as follows:

```
                                    (SEQ ID NO: 43)
TPEVWVQVQMEATELSSFTVHCGFLGPGSISLVTVSWGGPDGAGGTKLAV
LHPELGTRQWAPARQARWETQSSISLALEDSGASSPFANTTFCCKFASFP
EGSWESCGSLPPSSDPGLSAPPTPVPILRADHHHHHH.
```

2. Alpaca Immunization, Nanobody Phage Display Library Construction, and Antibody Screening Referring to the method of Example 1-1, alpacas were immunized with a his-tagged human PVRIG recombinant protein (h-PVRIG-his). PBMCs were separated from camel peripheral blood at day 56, and RNA was extracted and reverse-transcribed into cDNA to construct a phage library of anti-human PVRIG nanobodies. After 3 rounds of screening, 400 clones were sequenced. The variable region sequences of 2 of them are shown below, and the CDRs are shown in Table 13.

```
>The variable region of 30
                                    (SEQ ID NO: 44)
HVQLVESGGGSVQAGGSLRLSCEASGYSYSGDCMGWFRRAPGKERDEGVA
TIDNAGRIKYADSVKGRFTISHGNGKYILYLQMNSLKPEDTDMYYCAAGW
TFGGNCSPADWGQGTQVTVSS
                                    (SEQ ID NO: 45)
>The variable region of 151
HVQLVESGGGSVQAGGSLRLSCVASASGFTYRPYCMAWFRQAPGKEREAV
AGIDIFGGTTYADSVKGRFTASRDNAGFSLFLQMNDLKPEDTAMYYCAAG
DSPDGRCPPLGQGLNYWGQGTQVTVSS.
```

TABLE 13

The CDRs of anti-PVRIG nanobodies (Kabat numbering scheme)

| No. | | CDR sequences |
|---|---|---|
| 30 | CDR1 | GDCMG (SEQ ID NO: 46) |
| | CDR2 | TIDNAGRIKYADSVKG (SEQ ID NO: 47) |
| | CDR3 | GWTFGGNCSPAD (SEQ ID NO: 48) |
| 151 | CDR1 | YRPYCMA (SEQ ID NO: 49) |
| | CDR2 | GIDIFGGTTYADSVKG (SEQ ID NO: 50) |
| | CDR3 | GDSPDGRCPPLGQGLNY (SEQ ID NO: 51) |

The above antibody variable regions were linked to a human IgG4 heavy chain Fc region comprising a hinge region and mutations S228P, F234A, L235A, and K447A (Eu naming system) to construct full-length antibodies.

```
> hIgG4 Fc (S228P/F234A/L235A/K447A)
                                    (SEQ ID NO: 52)
ESKYGPPCPPCPAPEAAGGPSVFLFPPKPKDTLMISRTPEVTCVV
VDVSQEDPEVQFNWYVDGVEVHNAKTKPREEQFNSTYRVVSVLTV
LHQDWLNGKEYKCKVSNKGLPSSIEKTISKAKGQPREPQVYTLPP
SQEEMTKNQVSLTCLVKGFYPSDIAVEWESNGQPENNYKTTPPVL
DSDGSFFLYSRLTVDKSRWQEGNVFSCSVMHEALHNHYTQKSLSL
SLGA.
> The full length of 30
                                    (SEQ ID NO: 53)
HVQLVESGGGSVQAGGSLRLSCEASGYSYSGDCMGWFRRAPGKER
DEGVATIDNAGRIKYADSVKGRFTISHGNGKYILYLQMNSLKPED
TDMYYCAAGWTFGGNCSPADWGQGTQVTVSSESKYGPPCPPCPAP
EAAGGPSVFLFPPKPKDTLMISRTPEVTCVVVDVSQEDPEVQFNW
YVDGVEVHNAKTKPREEQFNSTYRVVSVLTVLHQDWLNGKEYKCK
VSNKGLPSSIEKTISKAKGQPREPQVYTLPPSQEEMTKNQVSLTC
LVKGFYPSDIAVEWESNGQPENNYKTTPPVLDSDGSFFLYSRLTV
DKSRWQEGNVFSCSVMHEALHNHYTQKSLSLSLGA;
> The full length of 151
                                    (SEQ ID NO: 54)
HVQLVESGGGSVQAGGSLRLSCVASASGFTYRPYCMAWFRQAPGK
EREAVAGIDIFGGTTYADSVKGRFTASRDNAGFSLFLQMNDLKPE
DTAMYYCAAGDSPDGRCPPLGQGLNYWGQGTQVTVSSESKYGPPC
PPCPAPEAAGGPSVFLFPPKPKDTLMISRTPEVTCVVVDVSQEDP
EVQFNWYVDGVEVHNAKTKPREEQFNSTYRVVSVLTVLHQDWLNG
KEYKCKVSNKGLPSSIEKTISKAKGQPREPQVYTLPPSQEEMTKN
QVSLTCLVKGFYPSDIAVEWESNGQPENNYKTTPPVLDSDGSFFL
YSRLTVDKSRWQEGNVFSCSVMHEALHNHYTQKSLSLSLGA.
```

The anti-PVRIG antibody CPA.7.021 shown in WO2016134333 was obtained by screening a phage library of antibodies. It is of the IgG1 subtype and can bind well to human PVRIG, but it does not bind to cynomolgus monkey PVRIG. The heavy and light chain variable regions of CPA.7.021 were linked to the human IgG4 heavy chain constant region (with mutations S228P, F234A, L235A, and K447A) and the human Kappa light chain constant region, respectively, to construct a positive antibody Tab5.

```
> The full-length heavy chain of Tab5
                                    (SEQ ID NO: 55)
EVQLVESGGGVVKPGGSLRLSCAASGFTFGTSSMNWVRQAPGKGL

EWVAVISFDGTEIHYADSVKGRFTISRDNSKSTVFLQMNSLRPDD

TALYYCAKGSGNIYFYSGMDVWGQGTTVTVSSASTKGPSVFPLAP

CSRSTSESTAALGCLVKDYFPEPVTVSWNSGALTSGVHTFPAVLQ

SSGLYSLSSVVTVPSSSLGTKTYTCNVDHKPSNTKVDKRVESKYG

PPCPPCPAPEAAGGPSVFLFPPKPKDTLMISRTPEVTCVVVDVSQ

EDPEVQFNWYVDGVEVHNAKTKPREEQFNSTYRVVSVLTVLHQDW

LNGKEYKCKVSNKGLPSSIEKTISKAKGQPREPQVYTLPPSQEEM

TKNQVSLTCLVKGFYPSDIAVEWESNGQPENNYKTTPPVLDSDGS

FFLYSRLTVDKSRWQEGNVFSCSVMHEALHNHYTQKSLSLSLGA

> The full-length light chain of Tab5
                                    (SEQ ID NO: 56)
DIQMTQSPSTLSASVGDRVTITCRAGQSISGWLAWFQQKPGKAPN

LLIYETSTLESGVPSRFSGSGSGTEYTLTISSLQPDDFATYYCQQ

YYSYPLTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC.
```

Nucleic acid sequences for expressing the above amino acid sequences were cloned into the pcDNA3.1 expression vector, and the antibodies were expressed and purified by conventional methods. It was verified that the antibodies of interest were obtained.

Example 2-2. Verification of Affinity of Anti-PVRIG Nanobodies for Antigen PVRIG

1. ELISA

A his-tagged PVRIG recombinant protein was directly used for coating. After an antibody was added, a secondary antibody (an HRP-conjugated anti-primary antibody Fc antibody) and the HRP substrate TMB were added to test the binding activity of the antibody to the antigen.

A 96-well plate was coated with 1 μg/mL human, cynomolgus monkey, or mouse PVRIG protein at 100 μL/well and incubated overnight at 4° C. The plate was washed three times with wash buffer. A blocking solution (PBS+0.05% Tween20+1% BSA) was added at 300 μL/well, and the plate was incubated at room temperature for 1 h. The plate was washed three times with wash buffer. Dilutions of the test anti-PVRIG antibodies were added at 100 μL/well. The plate was incubated at 37° C. for 1 h. The plate was washed three times with wash buffer. An HRP-labeled anti-human IgG secondary antibody (Sigma, A8667) was added at 100 μL/well. The plate was incubated at 37° C. for 1 h. The plate was washed three times with wash buffer. TMB was added at 100 μL/well, and the plate was incubated in the dark for 15 min. 0.16 M sulfuric acid was added at 50 mL/well. OD450 values were measured using a Thermo MpLtiSkanFc microplate reader, and the $EC_{50}$ values of the anti-PVRIG antibodies binding to the PVRIG recombinant proteins were calculated. All the antibodies in Table 14 showed relatively strong capacities to bind to the human or cynomolgus monkey PVRIG recombinant protein, but they did not bind to the mouse PVRIG recombinant protein.

TABLE 14

The results of the experiment on the binding of anti-PVRIG antibodies to PVRIG recombinant proteins of different species

| Antibody No. | Human PVRIG-his ELISA $EC_{50}$ (nM) | Monkey PVRIG-his ELISA $EC_{50}$ (nM) |
|---|---|---|
| 30 | 0.26 | 0.16 |
| 151 | 2.15 | 2.43 |
| Tab5 | 2.86 | No binding |
| hIgG4 | No binding | No binding |

2. FACS Assay

A stably transfected HEK293 cell strain expressing the human or cynomolgus monkey PVRIG gene was prepared. The cell strain was inoculated into a 96-well plate at $2\times10^5$ cells/well. The plate was centrifuged at 300 g for 5 min, and the supernatant was removed. 100 μL of test antibody was added, and the plate was incubated at 4° C. for 1 h. The plate was centrifuged, and the supernatant was removed. The plate was washed 3 times with 200 μL of wash buffer (PBS+2% FBS), and 100 μL of an Alexa Fluor 488-labeled anti-human IgG secondary antibody (Invitrogen, A-11013) diluted at 1:500 was added. The plate was incubated at 4° C. for 1 h. The plate was centrifuged, and the supernatant was removed. The plate was washed 3 times with 200 μL of wash buffer (PBS+2% FBS). The cells were resuspended in 100 μL of PBS and tested on a flow cytometer (BD FACS Calibur or BD FACS Canto_II). All the antibodies showed relatively strong capacities to bind to human or cynomolgus monkey PVRIG expressed on the cell surfaces, and their binding capabilities were significantly stronger than that of the positive antibody Tab5, which did not even bind to cynomolgus monkey PVRIG at all.

TABLE 15

The results of the experiment on the binding of anti-PVRIG antibodies to PVRIG of different species on cells

| Antibody No. | Human PVRIG FACS $EC_{50}$ (nM) | Monkey PVRIG FACS $EC_{50}$ (nM) |
|---|---|---|
| 30 | N.A. | 0.02 |
| 151 | 0.01 | 2.23 |
| Tab5 | 2.13 | No binding |
| hIgG4 | No binding | No binding |

(Note:
N.A., or not available, means that an accurate $EC_{50}$ value cannot be obtained by fitting as the binding was so strong that the antibody was not dissociated even at low concentrations)

3. Fortebio Assay

A Protein A biosensor (Fortebio, #18-5010) was immersed in 200 μL of KB buffer (PBS, pH 7.4, 0.02% tween-20, 0.10% BSA) for 60 s as a wetting treatment. Then an anti-PVRIG antibody was diluted to 10 μg/mL with KB buffer, and the sensor was immersed in 200 μL of the solution until the reading was 1.2 nm. The sensor was immersed in KB buffer for 100 s to remove excess antibody. His-tagged human PVRIG was serially diluted 2-fold to 64 nM-4 nM with KB buffer. The sensor was placed in the solution for 300 seconds of binding and then in KB buffer for 600 seconds of dissociation. Fitting was performed using a dynamic 1:1 binding mode. The affinities of anti-PVRIG antibodies for human PVRIG are shown in Table 16.

The results show that all the antibodies tested have high affinities for human PVRIG.

TABLE 16

| The affinities of anti-PVRIG antibodies for human PVRIG | | | |
|---|---|---|---|
| Antibody No. | Kon (1/Ms) | Koff (1/s) | KD (M) |
| 30 | 2.84E+05 | 2.05E−04 | 7.23E−10 |
| 151 | 2.61E+05 | 5.22E−05 | 2.00E−10 |
| Tab5 | 7.37E+05 | 1.61E−05 | 2.19E−10 |

Example 2-3. Functional and Activity Verification of Anti-PVRIG Nanobodies

1. Blocking of PVRIG Binding to PVRL2 by Anti-PVRIG Nanobodies

A 96-well plate was coated with 1 μg/mL human PVRIG recombinant protein (h-PVRIG-mIgG2a Fc) at 100 μL/well and incubated overnight at 4° C. The plate was washed three times with wash buffer. A blocking solution was added at 300 μL/well, and the plate was incubated at room temperature for 1 h. The plate was washed three times with wash buffer. 50 μL of diluted test anti-PVRIG antibody and 50 μL of his-tagged ligand PVRL2 were added to each well, and the plate was incubated at 37° C. for 1 h. The plate was washed three times with wash buffer. An HRP-labeled anti-his-tagged secondary antibody (Genscrpit) diluted at 1:2000 was added at 100 μL/well. The plate was incubated at 37° C. for 1 h. The plate was washed three times with wash buffer. TMB was added at 100 μL/well, and the plate was incubated in the dark for 15 min. 0.16 M sulfuric acid was added at 50 μL/well. OD values at 450 nm were measured using a Thermo MpLtiSkanFc microplate reader, and the $IC_{50}$ values of the anti-PVRIG antibodies blocking the binding of PVRIG to PVRL2 were calculated. The results in Table 17 show that all the antibodies tested can greatly inhibit the binding of human PVRIG to human PVRL2.

TABLE 17

| The blocking of human PVRIG/PVRL2 binding by antibodies | |
|---|---|
| Antibody No. | ELISA $IC_{50}$ (nM) |
| 30 | 1.11 |
| 151 | 0.37 |
| Tab5 | 1.16 |
| hIgG4 | No blocking |

2. Activity of Anti-PVRIG Nanobodies in Reporter Gene Cells

Firstly, a plvx-OS8 (G418 resistance) plasmid was constructed and transfected into 293F cells, and G418 screening was performed. The expression of OS8 by clone cells was tested using a flow cytometer, and meanwhile the activation of Jurkat cells by OS8 was tested. Clones with moderate activation were selected, yielding a 293F-OS8 cell strain. A plvx-PVRL2 plasmid was constructed and used to infect 293F-OS8 cells, and clones with the highest level of PVRL2 expression were obtained by screening using a flow cytometer, thereby yielding a 293F-OS8-PVRL2 cell strain.

Secondly, a plvx-NFAT-Luc (Hygromycin resistance) was constructed and packaged into a lentivirus. The lentivirus was used to infect Jurkat E6.1 cells. Hygromycin was added, and clones with resistance were obtained by screening. The clones were stimulated with OKT3, and clones with moderate Luciferase signals were obtained by screening, yielding a Jurkat-NFAT-Luc cell line. A plvx-PVRIG (Puromycin resistance) vector was constructed and packaged into a lentivirus, and the lentivirus was used to infect Jurkat-NFAT-Luc cells. Clones with the highest level of PVRIG expression were obtained by screening using a flow cytometer, thereby yielding a Jurkat-NFAT-Luc-PVRIG cell strain.

1E4 Jurkat-NFAT-Luc-PVRIG cells were incubated with a test antibody at 37° C. for 20 min. 1E5 293F-OS8-PVRL2 cells were added, and the mixture was incubated at 37° C. for 5 h. The mixture was centrifuged, and the supernatant was removed. Luciferase buffer (Promega, E6130) was added to lyse the cells, and the fluorescence value was measured. $EC_{50}$ values were calculated and used to evaluate the in vitro cell activity of the anti-PVRIG antibodies. The experimental results are shown in Table 18.

The results show that all the antibodies tested have relatively strong abilities to activate luciferase in Jurkat cells, and their activity was at least 10 or more times that of the positive antibody, indicating that these antibodies can bind to PVRIG and block the binding of PVRL2 to PVRIG.

TABLE 18

| The results of the experiment on the activity of anti-PVRIG antibodies in reporter gene cells | |
|---|---|
| Antibody No. | PVRIG reporter gene cell activity $EC_{50}$ (nM) |
| 30 | 0.06 |
| 151 | 0.04 |
| Tab5 | 0.74 |
| hIgG4 | No binding |

3. NK Cell Killing Experiment for Anti-PVRIG Nanobodies

PVRIG is expressed on NK cells, while PVRL2 is expressed in many tumor cells, including K562 cells. Anti-PVRIG antibodies can eliminate the inhibition of NK cell activity by tumor cells by blocking the binding of PVRL2 to PVRIG.

Human malignant non-Hodgkin lymphoma NK92 cells were added to a 96-well plate at 50 μL ($1\times10^5$ cells in total)/well. 50 μL of 20 nM or 100 nM test antibody was added, and the plate was incubated at 37° C. for 30 min. The plate was washed twice with wash buffer, and the cells were resuspended to a density of $2\times10^5$/mL. Human chronic myelogenous leukemia K562 cells were added at 50 μL ($1\times10^4$ cells in total)/well, making a ratio of the number of NK92 cells to the number of K562 cells of 10:1. The plate was incubated at 37° C. for 4 h. The killing activity was measured using the CytoTox-Glo cytotoxicity system (Promega, G9292). First, 50 μL of AAF-Glo reagent was added. The mixture was incubated at room temperature for 15 min, and the fluorescence of K562 cells killed by NK92 cells was measured. Then 50 μL of lysis buffer was added. The mixture was incubated at room temperature for 15 min to lyse the cells, and the fluorescence of all the cells was measured. Three control groups were prepared, including a sample containing only the culture medium (control group 1), a sample containing only NK92 cells (control group 2), and a sample containing only K562 cells (control group 3), and they were subjected to the same procedure.

The killing activity was calculated according to the following formula:

$$\text{killing activity (\%)}=\{[(R\text{-}BG)-(T\text{-}BG)-(E\text{-}BG)]/[(TL\text{-}BGL)-(T\text{-}BG)]\}\times100;$$

where R represents the fluorescence value after addition of AAF-Glo; BG represents the fluorescence value of control group 1 after addition of AAF-Glo; E represents the fluorescence value of control group 2 after addition of AAF-Glo;

and T represents the fluorescence value of control group 3 after addition of AAF-Glo; TL represents the fluorescence value of control group 3 after addition of lysis buffer, and BGL represents the fluorescence value of control group 1 after addition of lysis buffer.

According to the experimental results shown in Table 19, all the anti-PVRIG antibodies tested can significantly activate NK92 cells and kill K562 cells.

TABLE 19

The NK cell killing experiment for anti-PVRIG antibodies

| Antibody No. | Killing activity (%) (mean ± standard deviation) 20 nM antibody | 100 nM antibody |
|---|---|---|
| 30 | 36 ± 5 | 39 ± 5 |
| 151 | 35 ± 3 | 33 ± 2 |
| Tab5 | 32 ± 2 | 32 ± 3 |
| hIgG4 | 22 ± 1 | 22 ± 2 |

4. Mixed Lymphocyte Reaction (MLR) Experiment for Anti-PVRIG Nanobodies PGP

PVRIG is expressed on T cells, while PVRL2 is expressed on DCs. By blocking the binding of PVRL2 to PVRIG, anti-PVRIG antibodies can eliminate the inhibition of T cells by DCs and activate T cells.

PBMCs were isolated from peripheral blood collected from a first individual and cultured in RPMI 1640 medium containing 10% FBS. GM-CSF (Peprotech, 300-03-100UG) and IL-4 (Peprotech, 200-04-100UG) were both added at a final concentration of 50 ng/mL, and a cytokine-containing fresh medium was added every 2-3 days. After 6 days of culture, 1 μg/mL LPS (Sigma, L2880-25MG) was added, and the mixture was incubated for 24 h. DCs obtained by differentiation and maturation were collected. PBMCs were isolated from peripheral blood collected from a second individual, and $CD3^+$ T cells were isolated from the PBMCs using the EasySep human $CD3^+$ T cell isolation kit (Stemcell, 17952). The density of the $CD3^+$ T cells and DCs was adjusted, and $1\times10^5$ $CD3^+$ T cells and $2\times10^4$ DCs were added to each well. The test antibodies were added, and the plate was incubated at 37° C. for 120 h. The supernatants were taken and assayed for IFNγ content using an ELISA kit (R&D, DY202).

Figure 4:
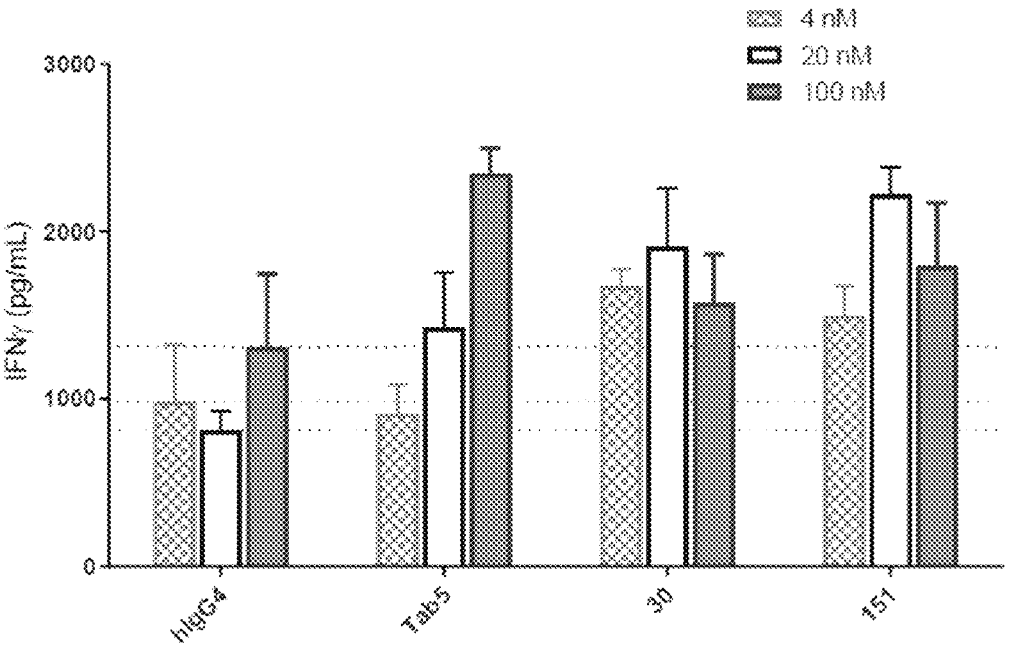
FIG. 4 shows the results of a mixed lymphocyte reaction (MLR) experiment for anti-PVRIG nanobodies 30 and 151, wherein Tab5 is used as a positive control and hIgG4 as a negative control.

As shown in Table 20 and FIG. 4, all of the anti-PVRIG antibodies tested can significantly activate the secretion of IFNγ by T cells, compared to the control antibody IgG4. Moreover, at low doses (such as 4 nM and 20 nM), the antibodies 30 and 151 of the present disclosure outperformed the positive control Tab5.

TABLE 20

The mixed lymphocyte reaction IFNγ secretion levels for anti-PVRIG antibodies

| Antibody No. | IFNγ (pg/mL) (mean ± standard deviation) 4 nM antibody | 20 nM antibody | 100 nM antibody |
|---|---|---|---|
| 30 | 1675 ± 101 | 1911 ± 347 | 1576 ± 288 |
| 151 | 1498 ± 175 | 2224 ± 162 | 1798 ± 373 |
| Tab5 | 912 ± 173 | 1425 ± 330 | 2349 ± 148 |
| hIgG4 | 984 ± 335 | 814 ± 112 | 1309 ± 437 |

Example 2-4. Modification of Sequences of Anti-PVRIG Nanobodies

By homologous modeling of the three-dimensional structures of selected anti-PVRIG antibody molecules and comparison of the sequences of the anti-PVRIG antibodies with the GermLine database of antibodies, a highly homologous human germline template IGHV3-7*01 was obtained. The CDRs were grafted into the corresponding human template. After the graft, the three-dimensional structures of the nanobodies were simulated again and analyzed. By back mutation of the embedded residues, the residues directly interacting with the CDRs, and the residues greatly influencing the conformation of the variable regions and optimization of the chemically unstable amino acid residues in the CDRs, a range of humanized nanobodies were generated. The human germline templates and humanized antibody heavy chain variable region sequences for the nanobodies are shown below.

> The variable region of 30H1 (SEQ ID NO: 57)
EVQLVESGGGLVQPGGSLRLSCAASGFTFSGDCMGWFRQAPGKGL
EGVATIDNAGRIKYADSVKGRFTISRDNAKNSLYLQMNSLRAEDT
AVYYCAAGWTFGGQCSPADWGQGTQVTVSS > The variable region of 30H2 (SEQ ID NO: 58)
EVQLVESGGGLVQPGGSLRLSCAASGFTFSGDCMGWFRQAPGKGL
DEGVATIDNAGRIKYADSVKGRFTISRDNAKNSLYLQMNSLRAED
TAVYYCAAGWTFGGQCSPADWGQGTQVTVSS > The variable region of 30H3 (SEQ ID NO: 59)
EVQLVESGGGLVQPGGSLRLSCAASGYSYSGDCMGWFRQAPGKGL
DEGVATIDNAGRIKYADSVKGRFTISRDNAKNSLYLQMNSLRAED
TAVYYCAAGWTFGGQCSPADWGQGTQVTVSS > The variable region of 30H4 (SEQ ID NO: 60)
EVQLVESGGGLVQPGGSLRLSCAASGFTFSGDCMGWFRQAPGKGL
DEGVATIDNAGRIKYADSVKGRFTISHGNAKYILYLQMNSLRAED
TAVYYCAAGWTFGGQCSPADWGQGTQVTVSS > The variable region of 30H5 (SEQ ID NO: 61)
EVQLVESGGGLVQPGGSLRLSCAASGYSYSGDCMGWFRQAPGKGL
DEGVATIDNAGRIKYADSVKGRFTISHGNAKYILYLQMNSLRAED
TAVYYCAAGWTFGGQCSPADWGQGTQVTVSS.

After humanization, antibodies 30H1 through 30H5 comprise CDR1s represented by (SEQ ID NO: 46) GDCMG, CDR2s represented by (SEQ ID NO: 47) TIDNAGRIKYADSVKG, and CDR3s represented by (SEQ ID NO: 99) GWTFGGQCSPAD.

> The variable region of 151H2 (SEQ ID NO: 62)
EVQLVESGGGLVQPGGSLRLSCAASGFTYRPYCMAWFRQAPGKGL
EAVAGIDIFGGTTYADSVKGRFTISRDNAKNSLYLQMNSLRAEDT
AVYYCAAGDSPDGRCPPLGQGLNYWGQGTMVTVSS -continued

```
> The variable region of 151H4
                                        (SEQ ID NO: 63)
EVQLVESGGGLVQPGGSLRLSCVASASGFTYRPYCMAWFRQAPGK

GLEAVAGIDIFGGTTYADSVKGRFTISRDNAKNSLYLQMNSLRAE

DTAVYYCAAGDSPDGRCPPLGQGLNYWGQGTMVTVSS

> The variable region of 151H7
                                        (SEQ ID NO: 64)
HVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSS

> The variable region of 151H8
                                        (SEQ ID NO: 65)
EVQLVESGGGLVQPGGSLRLSCVASASGFTYRPYCMAWFRQAPGK

GLEAVAGIDIFGGTTYADSVKGRFTISRDNAGFSLYLQMNSLRAE

DTAVYYCAAGDSPDGRCPPLGQGLNYWGQGTMVTVSS

> The variable region of 151H9
                                        (SEQ ID NO: 66)
HVQLVESGGGLVQPGGSLRLSCVASASGFTYRPYCMAWFRQAPGK

GLEAVAGIDIFGGTTYADSVKGRFTASRDNAGFSLYLQMNSLRAE

DTAVYYCAAGDSPDGRCPPLGQGLNYWGQGTMVTVSS.
```

The heavy chain variable regions of the humanized antibodies described above were linked to the heavy chain Fc region of human IgG4 to construct full-length anti-PVRIG antibodies. The heavy chain Fc region comprises a hinge region and mutations S228P/F234A/L235A/K447A or mutations S228P/K447A. The antibodies were expressed and purified by conventional methods. It was verified that the antibodies of interest were obtained.

Example 2-5. Activity and Functional Verification of Humanized Anti-PVRIG Antibodies

1. Binding of Humanized Anti-PVRIG Antibodies to Cells Expressing PVRIG

The binding of the anti-PVRIG antibodies to human or cynomolgus monkey PVRIG was measured by FACS using the method of Example 2-2. The experimental results are shown in Table 21.

TABLE 21

The results of the FACS experiment on the binding of anti-PVRIG nanobodies to PVRIG of different species

| Antibody No. | Human PVRIG FACS $EC_{50}$ (nM) | Monkey PVRIG FACS $EC_{50}$ (nM) |
|---|---|---|
| 30H1 | 0.024 | 0.374 |
| 30H2 | 0.003 | 0.005 |
| 30H3 | 0.004 | 0.003 |
| 151H4 | 0.240 | 0.035 |
| 151H7 | 0.002 | 0.467 |
| 151H8 | 0.006 | N.T. |
| 151H9 | 0.004 | 3.942 |
| Tab5 | 0.160 | No binding |
| hIgG4 | No binding | No binding |

(Note:
N.T., not tested)

2. Assay for Affinities of Humanized Anti-PVRIG Antibodies for PVRIG

The affinities of the humanized anti-PVRIG antibodies for human PVRIG protein were measured using the Fortebio assay method of Example 2-2. As shown in Table 22, all the antibodies have high affinities for human PVRIG protein.

TABLE 22

The affinities of humanized anti-PVRIG antibodies for human PVRIG

| Antibody No. | Kon (1/Ms) | Koff (1/s) | $K_D$ (M) |
|---|---|---|---|
| 20H5 | 1.93E+05 | 1.35E−05 | 6.98E−11 |
| 30H2 | 1.69E+05 | 3.25E−04 | 1.92E−09 |
| 30H3 | 1.48E+05 | 3.58E−04 | 2.41E−09 |
| 151H7 | 1.57E+05 | 1.88E−04 | 1.20E−09 |

3. Activity of Humanized Anti-PVRIG Antibodies in Reporter Gene Cells

The activity of the humanized anti-PVRIG antibodies in reporter gene cells was measured using the method of Example 2-3. The experimental results are shown in Table 23. All the antibodies listed in the Table have the ability to activate Jurkat cells.

TABLE 23

The activity of humanized anti-PVRIG antibodies in reporter gene cells

| Antibody No. | PVRIG reporter gene cell activity $EC_{50}$ (nM) |
|---|---|
| 30H2 | 0.176 |
| 30H3 | 0.078 |
| 151H7 | 0.038 |
| 151H8 | 0.058 |
| Tab5 | 1.380 |
| hIgG4 | No activation |

4. Capacities of Humanized Anti-PVRIG Antibodies to Activate NK Cell Killing The capacities of the humanized anti-PVRIG antibodies to activate NK cells were measured using the method of Example 2-3. The experimental results are shown in Tables 24 and 25. The results show that all the antibodies tested exhibited significant capacities to activate NK cells and promote the killing of the target cell K562 by NK cells.

TABLE 24

The NK cell killing experiment for humanized anti-PVRIG antibodies

| | Killing activity (%) (mean ± standard deviation) | | |
|---|---|---|---|
| Antibody No. | 4 nM antibody | 20 nM antibody | 100 nM antibody |
| 30 | 10.4 ± 0.9 | 11.9 ± 0.9 | 13.3 ± 0.7 |
| 30H2 | 7.7 ± 0.3 | 14.5 ± 0.8 | 17.7 ± 0.7 |
| Tab5 | 5.9 ± 0.1 | 7.9 ± 0.6 | 10.0 ± 1.2 |
| PBS | | 0.8 ± 0.6 | |

TABLE 25

The NK cell killing experiment for humanized anti-PVRIG antibodies

| | Killing activity (%) (mean ± standard deviation) | | |
|---|---|---|---|
| Antibody No. | 4 nM antibody | 20 nM antibody | 100 nM antibody |
| 151 | 20.9 ± 1.5 | 22.9 ± 1.5 | 24.2 ± 2.3 |
| 151H7 | 16.9 ± 0.8 | 21.0 ± 0.4 | 18.4 ± 0.9 |
| hIgG4 | 11.2 ± 0.4 | 11.7 ± 2.1 | 9.2 ± 0.6 |
| PBS | | 6.6 ± 1.1 | |

Example 2-6. Preparation of Anti-PVRIG/TIGIT Bispecific Antibodies

To investigate the effect of differently constructed anti-PVRIG/TIGIT bispecific antibodies on antibody function, the anti-PVRIG nanobody 151 was linked to the N-terminus or C-terminus of the heavy or light chain of the anti-TIGIT antibody 1708 by a linker of GGGGSGGGGS (SEQ ID NO: 100). Four anti-PVRIG/TIGIT bispecific antibodies were formed and named 1708-151-1, 1708-151-2, 1708-151-3 and 1708-151-4, which corresponded to the cases where 151 was linked to the heavy chain N-terminal, heavy chain C-terminal, light chain N-terminal and light chain C-terminal of 1708, respectively. The anti-TIGIT antibody 1708 is of the human IgG4 subtype and has the mutation S228P (Eu naming system). The sequences of the anti-TIGIT antibody 1708 and its bispecific antibodies formed with 151 are shown in Table 26 below. The sequences of the anti-TIGIT antibody are shown in Tables 27 and 28. The TIGIT antibody has been disclosed in WO2019062832A, which is incorporated herein by reference in its entirety.

TABLE 26

The sequences of the first and second polypeptide chains of anti-PVRIG/TIGIT bispecific antibodies

| Antibody No. | Amino acid sequences of full-length heavy/light chains | |
|---|---|---|
| 1708 (anti-TIGIT antibody) | First polypeptide chain | EVQLVQSGAEVKKPGASVKVSCKASGYTFTNYWMHWVRQAPGQGLEWMGRIDPDSTGSKYNEKFKTRVTMTRDTSTSTVYMELSSLRSEDTAVYYCAREGAYGYYFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 67) |
| | Second polypeptide chain | DIQMTQSPSSLSASVGDRVTITCRASENIYSYLAWYQQKPGKSPKLLIYNARTLAEGVPSRFSGSGSGTDFTLTISSLQPEDFATYYCQYHSGSPLPFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 68) |
| 1708-151-1 (antibody 151 linked to N-terminus of heavy chain of 1708) | First polypeptide chain | HVQLVESGGGSVQAGGSLRLSCVASASGFTYRPYCMAWFRQAPGKEREAVAGIDIFGGTTYADSVKGRFTASRDNAGFSLFLQMNDLKPEDTAMYYCAAGDSPDGRCPPLGQGLNYWGQGTQVTVSSGGGGSGGGGSEVQLVQSGAEVKKPGASVKVSCKASGYTFTNYWMHWVRQAPGQGLEWMGRIDPDSTGSKYNEKFKTRVTMTRDTSTSTVYMELSSLRSEDTAVYYCAREGAYGYYFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 69) |
| | Second polypeptide chain | Same as the light chain of 1708 (SEQ ID NO: 68) |
| 1708-151-2 (151 linked to C terminus of heavy chain of 1708) | First polypeptide chain | EVQLVQSGAEVKKPGASVKVSCKASGYTFTNYWMHWVRQAPGQGLEWMGRIDPDSTGSKYNEKFKTRVTMTRDTSTSTVYMELSSLRSEDTAVYYCAREGAYGYYFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSGGGGSHVQLVESGGGSVQAGGSLRLSCVASASGFTYRPYCMAWFRQAPGKEREAVAGIDIFGGTTYADSVKGRFTASRDNAGFSLFLQMNDLKPEDTAMYYCAAGDSPDGRCPPLGQGLNYWGQGTQVTVSS (SEQ ID NO: 70) |
| | Second polypeptide chain | Same as the light chain of 1708 (SEQ ID NO: 68) |
| 1708-151-3 (151 linked to N-terminus of light chain of 1708) | First polypeptide chain | Same as the heavy chain of 1708 (SEQ ID NO: 67) |
| | Second polypeptide | HVQLVESGGGSVQAGGSLRLSCVASASGFTYRPYCMAWFRQAPGKEREAVAGIDIFGGTTYADSVKGRFTASRDNAGFSLFLQMN |

TABLE 26-continued

The sequences of the first and second polypeptide chains of anti-PVRIG/TIGIT bispecific antibodies

| Antibody No. | Amino acid sequences of full-length heavy/light chains | |
|---|---|---|
| | chain | DLKPEDTAMYYCAAGDSPDGRCPPLGQGLNYWGQGTQVTVS SGGGGSGGGGSDIQMTQSPSSLSASVGDRVTITCRASENIYSYL AWYQQKPGKSPKLLIYNARTLAEGVPSRFSGSGSGTDFTLTISS LQPEDFATYYCQYHSGSPLPFGGGTKVEIKRTVAAPSVFIFPPSD EQLKSGTASVVCLLNNFYPREAKVQWKVDNALQSGNSQESVT EQDSKDSTYSLSSTLTLSKADYEKHKVYACEVTHQGLSSPVTK SFNRGEC (SEQ ID NO: 71) |
| 1708-151-4 (151 linked to C-terminus of light chain of 1708) | First polypeptide chain | Same as the heavy chain of 1708 (SEQ ID NO: 67) |
| | Second polypeptide chain | DIQMTQSPSSLSASVGDRVTITCRASENIYSYLAWYQQKPGKSP KLLIYNARTLAEGVPSRFSGSGSGTDFTLTISSLQPEDFATYYCQ YHSGSPLPFGGGTKVEIKRTVAAPSVFIFPPSDEQLKSGTASVVC LLNNFYPREAKVQWKVDNALQSGNSQESVTEQDSKDSTYSLS STLTLSKADYEKHKVYACEVTHQGLSSPVTKSFNRGECGGGGS GGGGSHVQLVESGGGSVQAGGSLRLSCVASASGFTYRPYCMA WFRQAPGKEREAVAGIDIFGGTTYADSVKGRFTASRDNAGFSLF LQMNDLKPEDTAMYYCAAGDSPDGRCPPLGQGLNYWGQGTQ VTVSS (SEQ ID NO: 72) |

TABLE 27

The sequences of the heavy and light chain CDRs of the anti-TIGIT antibody (Kabat numbering scheme)

| Antibody | Heavy chain | | Light chain | |
|---|---|---|---|---|
| 1708 | HCDR1 | NYWMH (SEQ ID NO: 73) | LCDR1 | RASENI YSYLA (SEQ ID NO: 76) |
| | HCDR2 | RIDPDSTGS KYNEKFKT (SEQ ID NO: 74) | LCDR2 | NARTL AE (SEQ ID NO: 77) |
| | HCDR3 | EGAYGY YFDY (SEQ ID NO: 75) | LCDR3 | QYHSG SPLP (SEQ ID NO: 78) |

TABLE 28

The sequences of the heavy chain VHs and light chain VLs of the anti-TIGIT antibody

| Antibody | Sequences of heavy chain VHs and light chain VLs |
|---|---|
| 1708-VH1 | EVQLVQSGAEVKKPGASVKVSCKASGYTFT NYWMHWVRQAPGQGLEWMGRIDPDSTGSKY NEKFKTRVTMTRDTSTSTVYMELSSLRSED TAVYYCAREGAYGYYFDYWGQGTLVTVSS (SEQ ID NO: 79) |
| 1708-VH2 | EVQLVQSGAEVKKPGASVKVSCKASGYTFT NYWMHWVRQAPGQGLEWMGRIDPDSTGSKY NEKFKTRVTMTVDTSTSTVYMELSSLRSED TAVYYCAREGAYGYYFDYWGQGTLVTVSS (SEQ ID NO: 80) |
| 1708-VH3 | EVQLVQSGAEVKKPGASVKVSCKASGYTFT NYWMHWVRQAPGQGLEWIGRIDPDSTGSKY NEKFKTRVTMTVDTSTSTAYMELSSLRSED TAVYYCAREGAYGYYFDYWGQGTLVTVSS (SEQ ID NO: 81) |

TABLE 28-continued

The sequences of the heavy chain VHs and light chain VLs of the anti-TIGIT antibody

| Antibody | Sequences of heavy chain VHs and light chain VLs |
|---|---|
| 1708-VL1 | DIQMTQSPSSLSASVGDRVTITCRASENIY SYLAWYQQKPGKAPKLLIYNARTLAEGVPS RFSGSGSGTDFTLTISSLQPEDFATYYCQY HSGSPLPFGGGTKVEIK (SEQ ID NO: 82) |
| 1708-VL2 | DIQMTQSPSSLSASVGDRVTITCRASENIY SYLAWYQQKPGKSPKLLIYNARTLAEGVPS RFSGSGSGTDFTLTISSLQPEDFATYYCQY HSGSPLPFGGGTKVEIK (SEQ ID NO: 83) |

Different humanized anti-PVRIG antibody variable regions (30H2, 151H7, and 151H8) were linked to the N-terminus of the heavy chain of the anti-TIGIT antibody 1708; that is, bispecific antibodies were constructed using a bispecific antibody structure similar to 1708-151-1. Linker sequences are double-underlined in the sequences below.

> The first polypeptide chain of 1708-30H2 (SEQ ID NO: 84)

EVQLVESGGGLVQPGGSLRLSCAASGFTFSGDCMGWFRQAPGKGL

DEGVATIDNAGRIKYADSVKGRFTISRDNAKNSLYLQMNSLRAED

TAVYYCAAGWTFGGQCSPADWGQGTQVTVSSGGGGSGGGGSEVQL

VQSGAEVKKPGASVKVSCKASGYTFTNYWMHWVRQAPGQGLEWMG

RIDPDSTGSKYNEKFKTRVTMTRDTSTSTVYMELSSLRSEDTAVY

YCAREGAYGYYFDYWGQGTLVTVSSASTKGPSVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVQF

NWYVDGVEVHNAKTKPREEQFNSTYRVVSVLTVLHQDWLNGKEYK

-continued

CKVSNKGLPSSIEKTISKAKGQPREPQVYTLPPSQEEMTKNQVSL

TCLVKGFYPSDIAVEWESNGQPENNYKTTPPVLDSDGSFFLYSRL

TVDKSRWQEGNVFSCSVMHEALHNHYTQKSLSLSLGK

> The first polypeptide chain of 1708-151H7 (SEQ ID NO: 85)

HVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSSGGGGSGGG

GSEVQLVQSGAEVKKPGASVKVSCKASGYTFTNYWMHWVRQAPGQ

GLEWMGRIDPDSTGSKYNEKFKTRVTMTRDTSTSTVYMELSSLRS

EDTAVYYCAREGAYGYYFDYWGQGTLVTVSSASTKGPSVFPLAPC

SRSTSESTAALGCLVKDYFPEPVTVSWNSGALTSGVHTFPAVLQS

SGLYSLSSVVTVPSSSLGTKTYTCNVDHKPSNTKVDKRVESKYGP

PCPPCPAPEFLGGPSVFLFPPKPKDTLMISRTPEVTCVVVDVSQE

DPEVQFNWYVDGVEVHNAKTKPREEQFNSTYRVVSVLTVLHQDWL

NGKEYKCKVSNKGLPSSIEKTISKAKGQPREPQVYTLPPSQEEMT

KNQVSLTCLVKGFYPSDIAVEWESNGQPENNYKTTPPVLDSDGSF

FLYSRLTVDKSRWQEGNVFSCSVMHEALHNHYTQKSLSLSLGK

> The first polypeptide chain of 1708-151H8 (SEQ ID NO: 86)

EVQLVESGGGLVQPGGSLRLSCVASASGFTYRPYCMAWFRQAPGK

GLEAVAGIDIFGGTTYADSVKGRFTISRDNAGFSLYLQMNSLRAE

DTAVYYCAAGDSPDGRCPPLGQGLNYWGQGTMVTVSSGGGGSGGG

GSEVQLVQSGAEVKKPGASVKVSCKASGYTFTNYWMHWVRQAPGQ

GLEWMGRIDPDSTGSKYNEKFKTRVTMTRDTSTSTVYMELSSLRS

EDTAVYYCAREGAYGYYFDYWGQGTLVTVSSASTKGPSVFPLAPC

SRSTSESTAALGCLVKDYFPEPVTVSWNSGALTSGVHTFPAVLQS

SGLYSLSSVVTVPSSSLGTKTYTCNVDHKPSNTKVDKRVESKYGP

PCPPCPAPEFLGGPSVFLFPPKPKDTLMISRTPEVTCVVVDVSQE

DPEVQFNWYVDGVEVHNAKTKPREEQFNSTYRVVSVLTVLHQDWL

NGKEYKCKVSNKGLPSSIEKTISKAKGQPREPQVYTLPPSQEEMT

-continued

KNQVSLTCLVKGFYPSDIAVEWESNGQPENNYKTTPPVLDSDGSF

FLYSRLTVDKSRWQEGNVFSCSVMHEALHNHYTQKSLSLSLGK.

The second polypeptide chains of 1708-30H2, 1708-151H7, and 1708-151H8 are all identical to the light chain of 1708 (SEQ ID NO: 68).

Transient transfection and antibody expression and purification were performed by conventional methods. It was verified that the full-length anti-PVRIG/TIGIT bispecific antibodies of the present disclosure were obtained, and they all showed good expression levels and purity.

Example 2-7. Activity and Functional Verification of Anti-PVRIG/TIGIT Bispecific Antibodies 1. Binding of Bispecific Antibodies to Human PVRIG and Blocking of Ligand PVRL2

Experiments were conducted using the methods of Examples 2-2 and 2-3. The results show that there was no statistically significant difference in the binding of the bispecific antibodies of different configurations-1708-151-1, 1708-151-2, 1708-151-3, and 1708-151-4—to human PVRIG recombinant protein and cells overexpressing human PVRIG, and in their blocking of PVRL2 binding to PVRIG.

2. Binding of Bispecific Antibodies to Human TIGIT and Blocking of Ligand PVR

Experiments were conducted using the methods of Examples 2-2 and 2-3 (the corresponding receptor and ligand were changed to human TIGIT and human PVR), and the results are shown in Table 29. The results show that there was no statistically significant difference in the binding of the bispecific antibodies of different configurations-1708-151-1, 1708-151-2, 1708-151-3, and 1708-151-4—and the anti-TIGIT antibody to human TIGIT recombinant protein and cells overexpressing human TIGIT, and in their blocking of TIGIT binding to its ligand PVR.

It can be seen that whether the anti-PVRIG antibody was linked to the N-terminus or C-terminus of the heavy or light chain of the anti-TIGIT antibody, the binding to PVRIG and TIGIT and the blocking of the ligand were both maintained, and good expression levels and purity were showed.

3. Binding of Humanized Anti-PVRIG/TIGIT Bispecific Antibodies to PVRIG and TIGIT and Blocking of Corresponding Ligands The binding of the humanized anti-PVRIG/TIGIT bispecific antibodies to human and cynomolgus monkey PVRIG and their blocking of the ligand for human PVRIG were measured using the methods of Examples 2-2 and 2-3. The results are shown in Table 29. The results show that all the humanized bispecific antibodies can bind to human PVRIG and block the binding of PVRIG to PVRL2.

TABLE 29

The binding of humanized bispecific antibodies to PVRIG and their blocking of the ligand

| Antibody No. | $EC_{50}$ (nM) of binding to human PVRIG recombinant protein | $EC_{50}$ (nM) of binding to cells overexpressing human PVRIG | $IC_{50}$ (nM) of blocking binding of human PVRIG to human PVRL2 |
|---|---|---|---|
| 1708-30H2 | 0.320 | 0.056 | 0.552 |
| 1708-151H7 | 0.679 | 0.043 | 0.598 |
| 1708-151H8 | 0.390 | 0.094 | 0.654 |
| 1708 | No binding | No binding | Not tested |
| Tab5 | 1.407 | 0.789 | 0.964 |
| hIgG4 | No binding | No binding | No blocking |

Using methods similar to those of Examples 2-2 and 2-3, the binding of the humanized anti-PVRIG/TIGIT bispecific antibodies to human and cynomolgus monkey TIGIT and their blocking of human TIGIT binding to the ligand were measured. In the methods, TIGIT was used in place of PVRIG protein, and PVR was used in place of PVRL2. The results are shown in Table 30. The results show that all the bispecific antibodies can bind to human TIGIT and block the binding of TIGIT to PVR.

TABLE 30

The binding of humanized bispecific antibodies to TIGIT and their blocking of the ligand

| Antibody No. | $EC_{50}$ (nM) of binding to human TIGIT recombinant protein | $EC_{50}$ (nM) of binding to cells overexpressing human TIGIT | $IC_{50}$ (nM) of blocking binding of human TIGIT to human PVR |
|---|---|---|---|
| 1708-30H2 | 0.153 | 0.010 | 1.014 |
| 1708-151H7 | 0.160 | 0.012 | 0.773 |
| 1708-151H8 | 0.184 | 0.006 | 1.087 |
| 1708 | 0.133 | 0.0027 | 0.779 |
| Tab5 | No binding | No binding | Not tested |
| hIgG4 | No binding | No binding | No blocking |

The affinities of the bispecific antibodies for human PVRIG and human TIGIT were measured using Biacore. A humanized bispecific antibody was captured on a Protein A biosensor chip (GE lifesciences, 29127557) of a Biacore instrument (Biacore X100, GE), and then a series of concentrations of human PVRIG antigen (AcroBiosystem, PVG-H52H4) or human TIGIT antigen (AcroBiosystem, TIT-H52H3) were made to flow over the surface of the chip to obtain a binding and dissociation curve. The results are shown in Table 31.

TABLE 31

The affinities of humanized bispecific antibodies for human PVRIG and human TIGIT

| Antibody No. | Antigen | kon (1/Ms) | koff (1/s) | $K_D$ (M) |
|---|---|---|---|---|
| 1708-30H2 | Human PVRIG | 1.29E+07 | 9.12E−03 | 7.06E−10 |
| 1708-151H7 | | 6.06E+06 | 7.57E−04 | 1.25E−10 |
| 1708-30H2 | Human TIGIT | 3.08E+06 | 1.58E−04 | 5.12E−11 |
| 1708-151H7 | | 1.40E+06 | 1.16E−04 | 8.28E−11 |

Figure 5:
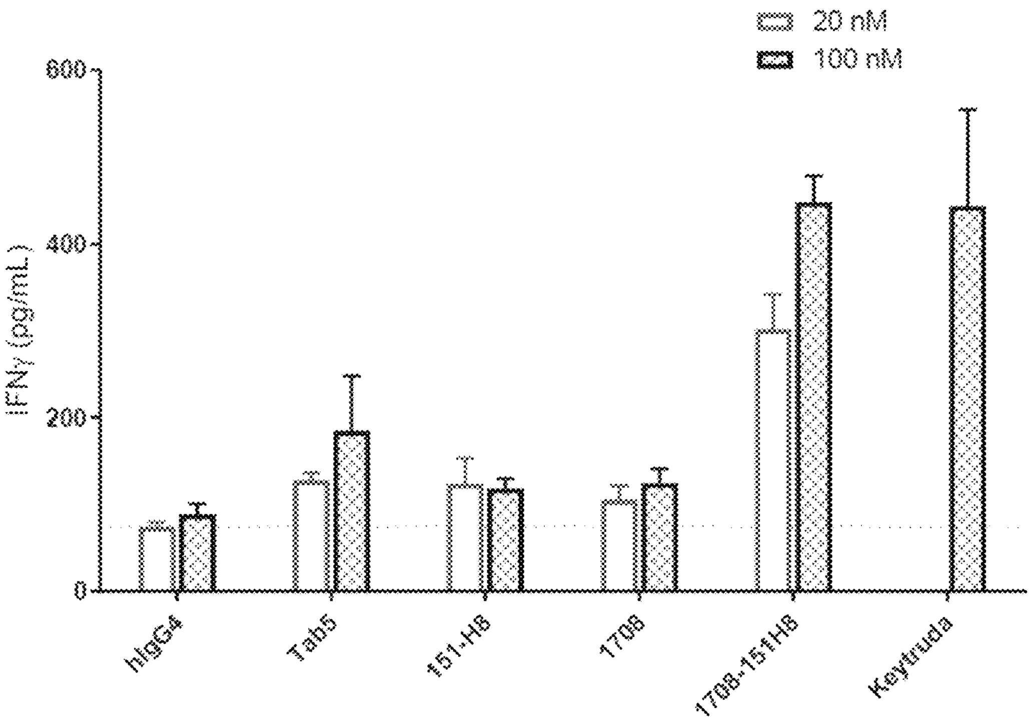
FIG. 5 shows the results of an MLR experiment for the anti-PVRIG/TIGIT bispecific antibody 1708-151H8, wherein 151H8, 1708, hIgG4, Tab5, and pembrolizumab are used as controls.

4. Mixed Lymphocyte Reaction (MLR) Experiment for Anti-PVRIG/TIGIT Bispecific Antibody The capacity of the humanized anti-PVRIG/TIGIT bispecific antibody to activate T cells was tested using the method in part 4 of Example 2-3. The experimental results are shown in FIG. 5 and Table 32. The results show that the humanized anti-PVRIG/TIGIT bispecific antibody 1708-151H8 has a significant capacity to activate T cells and promote the secretion of IFNγ by T cells. Importantly, the activity of the bispecific antibody is stronger than that of the anti-PVRIG antibody 151H8 alone or the anti-TIGIT antibody 1708 alone.

TABLE 32

The mixed lymphocyte reaction IFNγ secretion levels for the humanized bispecific antibody

| Antibody No. | IFNγ (pg/mL) (mean ± standard deviation) 20 nM antibody | 100 nM antibody |
|---|---|---|
| hIgG4 | 74 ± 5 | 89 ± 12 |
| 151H8 | 124 ± 29 | 118 ± 11 |
| 1708 | 106 ± 16 | 125 ± 16 |
| 1708-151H8 | 303 ± 40 | 448 ± 40 |
| Tab5 | 128 ± 8.9 | 185 ± 63 |
| Pembrolizumab | Not tested | 444 ± 111 |

Example 2-8. Evaluation of Anti-Tumor Effects of Anti-PVRIG/TIGIT Bispecific Antibodies in Mouse Subcutaneous Xenograft Tumor Model of Human Melanoma A375 Mixed with Human PBMCs To further investigate the role of bispecific antibody subtypes in animal efficacy, animal efficacy tests were performed. The heavy chain variable region of 1708-IgG1 was identical to that of 1708 except that the heavy chain constant region subtype was changed to IgG1; the full-length light chain of 1708-IgG1 and the second polypeptide chain of 1708-151-IgG1 were identical to the light chain of 1708.

NCG mice, female, aged 4-8 weeks, weighing about 18-22 g, purchased from Jiangsu GemPharmatech Co., Ltd. All the NCG mice were kept in an SPF animal house with an IVC constant-temperature and constant-pressure system.

A375 cells were cultured in DMEM medium containing 10% fetal bovine serum (FBS). A375 cells in the exponential growth phase were collected and resuspended in HBSS to a concentration appropriate for subcutaneous tumor inoculation into NCG mice. The A375 cells used for co-culture were treated with Mitomycin C for 2 h and washed three times with PBS. Peripheral blood was collected from a normal human, and human PBMCs were isolated by density gradient centrifugation and counted. The PBMCs were then resuspended in RPMI1640 medium (containing IL2 and 10% FBS) to a concentration of $3\times10^6$ cells/mL and co-cultured with the Mitomycin C-treated A375 cells. After 6 days of co-culture, PBMCs were harvested, and meanwhile freshly digested A375 cells were harvested. Each mouse was inoculated with $5\times10^5$ PBMCs and $4\times10^6$ A375 cells; the inoculation volume was 0.2 mL/mouse (containing 50% Matrigel); the cells were inoculated subcutaneously into the right side of each female NCG mouse. The mice were randomized into groups according to body weight and dosed. The method of administration, the doses, and the route of administration are detailed in Table 33. The day when the grouping and administration were performed was day 0. Given that the molecular weights of the anti-PVRIG antibody and anti-TIGIT antibody are different, these doses ensured that the anti-PVRIG antibody and anti-TIGIT antibody had the same initial molar concentration.

TABLE 33

The administration regimen

| Group | Administration group | N | Dose (mg/kg) | Administration regimen (Route of administration) |
|---|---|---|---|---|
| 1 | hIgG1 | 7 | 30 | Q2 D |
| 2 | 151-IgG4 | 7 | 16.1 | (i.p) |
| 3 | 1708-IgG1 | 7 | 30 | |
| 4 | 151-IgG4 + 1708-IgG1 | 7 | 16.1 + 30 | |
| 5 | 1708-151-IgG4 | 7 | 35.8 | |

(Note:
N: the number of animals used; i.p.: intraperitoneal injection; Q2 D: once every two days; administration volume: adjusted depending on the body weight of tumor-bearing mice (0.1 mL/10 g))

Figure 6A:
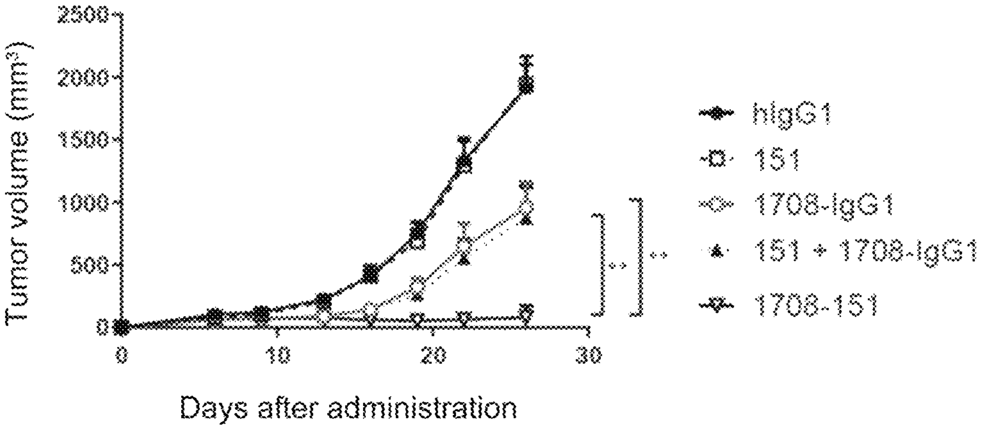
FIGS. 6A to 6B show the anti-tumor effects of the anti-PVRIG/TIGIT bispecific antibody 1708-151 and a combination of 1708 and 151 on a mouse subcutaneous xenograft tumor model of human melanoma A375 mixed with human PBMCs.
Figure 6B:
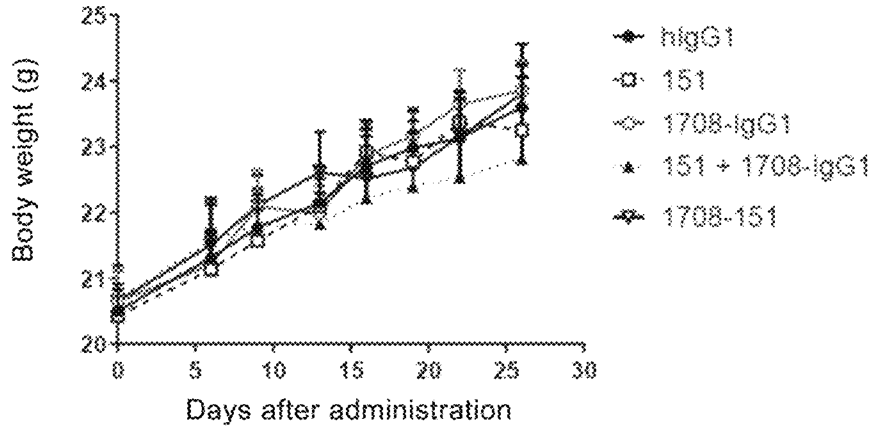

After the start of administration, the tumor volume and body weight of the mice were measured 2 times a week. The experimental results are shown in Table 34 and FIGS. 6A and 6B.

TABLE 34

The anti-tumor effect of the anti-PVRIG/TIGIT bispecific antibody in the human A375 tumor mouse model

| Group | Tumor volume at day 0 ($mm^3$) | Tumor volume at day 26 ($mm^3$) (mean ± standard deviation) | TGI (%) | T/C (%) | p value |
|---|---|---|---|---|---|
| 1 | 0 | 1913.62 ± 188.23 | — | — | — |
| 2 | 0 | 1942.70 ± 223.36 | −1.52 | 101.52 | 0.916 |
| 3 | 0 | 958.83 ± 204.39 | 49.89 | 50.11 | <0.001*** |
| 4 | 0 | 876.21 ± 243.70 | 54.21 | 45.79 | <0.001*** |
| 5 | 0 | 79.99 ± 36.57 | 95.82 | 4.18 | <0.001*** |

(Note:
*P < 0.05, P < 0.01, and *P < 0.001 are thought to indicate significant differences compared to the control group (hIgG1))

At the end of the experiment (day 26 post-administration), the anti-PVRIG antibody 151-IgG4 single-drug group showed no significant difference from the control group. The anti-TIGIT antibody 1708-IgG1 single-drug group and the anti-PVRIG antibody 151-IgG4 and anti-TIGIT antibody 1708-IgG1 combination group showed reductions in tumor volume. The 1708-151-IgG4 bispecific antibody group could even achieve complete inhibition of tumor growth, showing significant differences from the other groups (see FIG. 6A).

The mice were randomized into groups according to body weight and dosed. The method of administration, the doses, and the route of administration are detailed in Table 35. The day when the grouping and administration were performed was day 0.

TABLE 35

The administration regimen

| Group | Administration group | N | Dose (mg/kg) | Administration regimen (Route of administration) |
|---|---|---|---|---|
| 1 | hIgG4 | 7 | 35.8 | Q2 D |
| 2 | 1708-30H2-IgG4 | 7 | 12 | (i.p) |
| 3 | 1708-151H7-IgG4 | 7 | 12 | |

(Note:
N: the number of animals used; i.p.: intraperitoneal injection; Q2 D: once every two days; administration volume: adjusted depending on the body weight of tumor-bearing mice (0.1 mL/10 g))

After the start of administration, the body weight and tumor volume of the mice were measured 2 times a week. The experimental results are shown in Table 36 and FIGS. 7A-7B.

TABLE 36

The anti-tumor effects of the anti-PVRIG/TIGIT bispecific antibodies in the human A375 tumor mouse model

| Group | Tumor volume at day 0 ($mm^3$) | Tumor volume at day 28 ($mm^3$) (mean ± standard deviation) | TGI (%) | T/C (%) | p value |
|---|---|---|---|---|---|
| 1 | 0 | 2239.26 ± 322.87 | — | — | — |
| 2 | 0 | 1435.36 ± 117.61 | 35.90 | 64.10 | <0.05* |
| 3 | 0 | 1468.96 ± 67.07 | 34.40 | 65.60 | <0.05* |

(Note:
*P < 0.05, P < 0.01, and *P < 0.001 are thought to indicate significant differences compared to the control group (hIgG1))

Figure 7A:
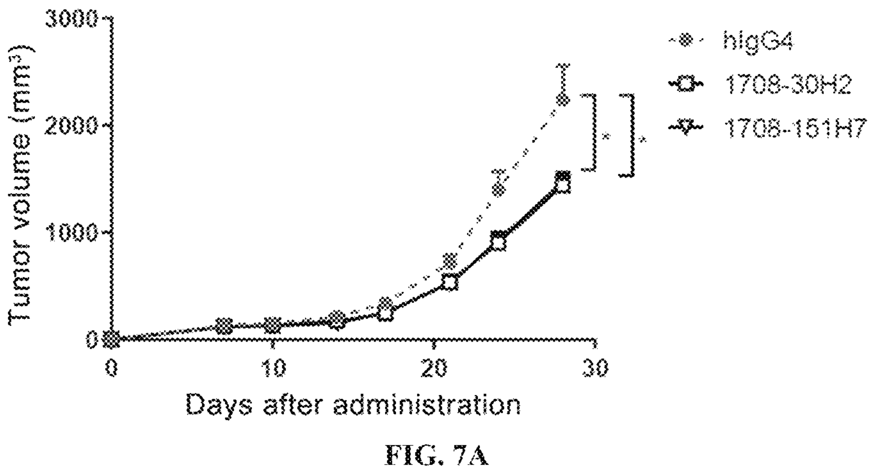
FIGS. 7A to 7B show the anti-tumor effects of the anti-PVRIG/TIGIT bispecific antibodies 1708-151H7 and 1708-30H2 on a mouse subcutaneous xenograft tumor model of human melanoma A375 mixed with human PBMCs.
Figure 7B:
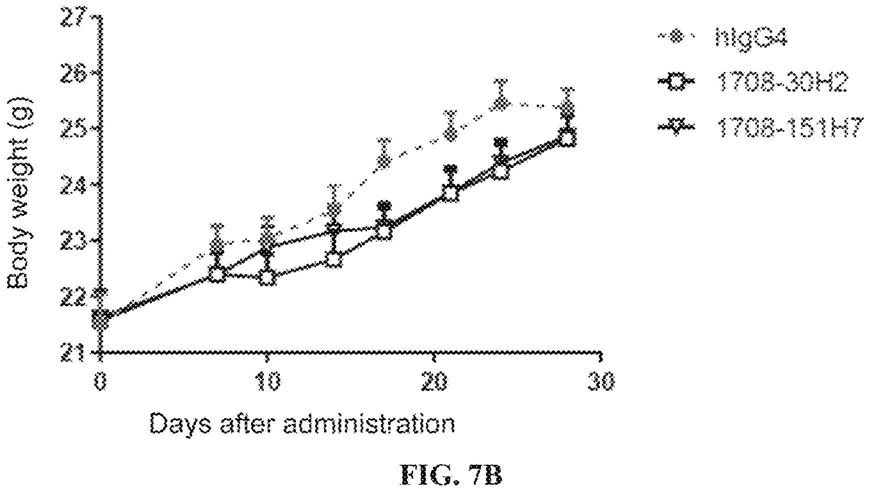

At the end of the experiment (day 28 post administration), both the 1708-30H2 and 1708-151H7 bispecific antibody groups could achieve effective inhibition of tumor growth at low doses, showing significant differences from the control group (see FIGS. 7A and 7B).

Example 3. Anti-PD-1/PVRIG/TIGIT Trispecific Antibodies

Figure 8:
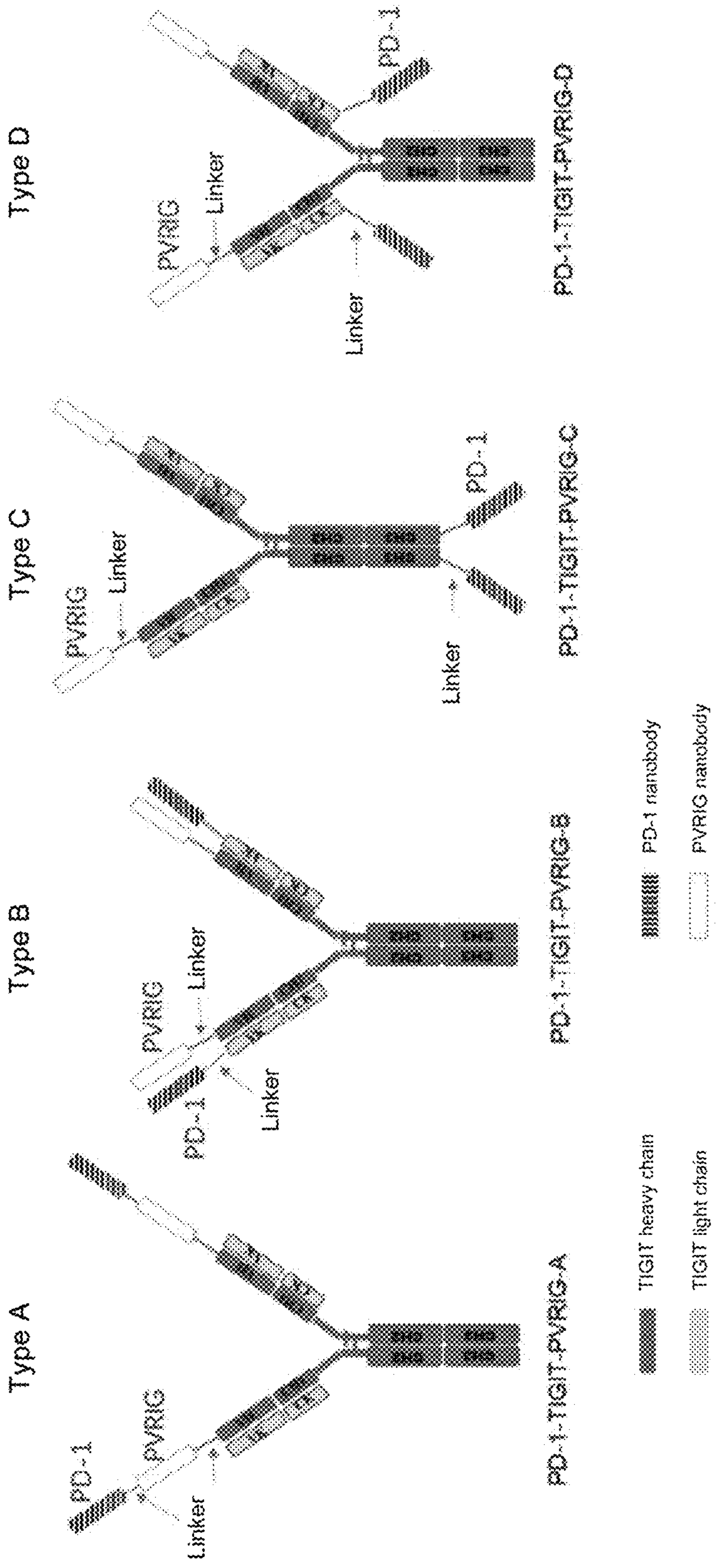
FIG. 8 is a schematic diagram of 4 antibody configurations of anti-PD-1/PVRIG/TIGIT trispecific antibodies.

Example 3-1. Design and Preparation of Anti-PD-1/PVRIG/TIGIT Trispecific Antibodies There are four types of trispecific antibodies: types A, B, C, and D, which are schematically shown in FIG. 8.

Type A: Anti-PD-1 nanobodies are linked to anti-PVRIG nanobodies by linkers (e.g., GGGGSGGGGS), and then the anti-PVRIG nanobodies are linked to the N-termini of the heavy chains of an anti-TIGIT antibody by linkers (A of FIG. 8).

Type B: Anti-PVRIG antibodies are linked to the N-termini of the heavy chains of a TIGIT IgG molecule by linkers, and anti-PD-1 antibodies are linked to the N-termini of the light chains of the anti-TIGIT antibody by linkers (B of FIG. 8).

Type C: Anti-PVRIG antibodies are linked to the N-termini of the heavy chains of a TIGIT IgG molecule by linkers. Anti-PD-1 antibodies are linked to the C-termini of the heavy chains of the anti-TIGIT antibody by linkers (GGGGSGGGGS) (C of FIG. 8). Type D: Anti-PVRIG antibodies are linked to the N-termini of the heavy chains of a TIGIT IgG molecule by linkers. Anti-PD-1 antibodies are linked to the C-termini of the light chains of the anti-TIGIT antibody by linkers (D of FIG. 8).

The names of the trispecific antibodies in the present disclosure are shown in Table 37. For example, A17m0902-1708-30H2-A represents that the clones of the anti-PD-1, TIGIT, and PVRIG antibodies used are A17m0902, 1708, and 30H2, respectively, and the trispecific antibody is of type A.

-continued

*SSIEKTISKAKGQPREPQVYTLPPSQEEMTKNQVSLTCLVKGFYP*

*SDIAVEWESNGQPENNYKTTPPVLDSDGSFFLYSRLTVDKSRWQE*

*GNVFSCSVMHEALHNHYTQKSLSLSLGK.*

The second polypeptide chain of A17m0902-1708-30H2-A is set forth in SEQ ID NO: 68.

The first polypeptide chain of A17m0902-1708-30H2-B is set forth in SEQ ID NO: 84.

> The second polypeptide chain of A17m0902-1708-30H2-B
(SEQ ID NO: 88)

EVQLVESGGGLVQPGGSLRLSCAASGLTFSDYSMSWYRQAPGKGR

ELVAIISGSGVITHYVDSVKGRFTISRDNAKNTLYLQMRSLRAED

TAVYYCRAVSDWEDYWGQGTQVTVSSGGGGSGGGGSDIQMTQSPS

TABLE 37

| The names of anti-PD-1/PVRIG/TIGIT trispecific antibodies | | |
|---|---|---|
| | Antibody No. | |
| Antibody type name | Anti-PVRIG antibody being 30H2 | Anti-PVRIG antibody being 151H7 |
| PD-1/PVRIG/TIGIT-A | A17m0902-1708-30H2-A | A17m0902-151H7-A |
| PD-1/PVRIG/TIGIT-B | A17m0902-1708-30H2-B | A17m0902-151H7-B |
| PD-1/PVRIG/TIGIT-C | A17m0902-1708-30H2-C | A17m0902-151H7-C |
| PD-1/PVRIG/TIGIT-D | A17m0902-1708-30H2-D | A17m0902-151H7-D |
| PD-1/PVRIG/TIGIT-A | A17h1-1708-30H2-A | A17h1-1708-151H7-A |
| PD-1/PVRIG/TIGIT-B | A17h1-1708-30H2-B | A17h1-1708-151H7-B |
| PD-1/PVRIG/TIGIT-C | A17h1-1708-30H2-C | A17h1-1708-151H7-C |
| PD-1/PVRIG/TIGIT-D | A17h1-1708-30H2-D | A17h1-1708-151H7-D |

The A17h1-related molecules in Table 37 were all obtained on the basis of their corresponding A17m0902-related molecules by replacing the A17m0902 (SEQ ID NO: 33) sequence with the A17h1 (SEQ ID NO: 13) sequence.

The sequences are as follows (linkers underlined, Fc or light chain Cκ italicized):

> The first polypeptide chain of A17m0902-1708-30H2-A
(SEQ ID NO: 87)

EVQLVESGGGLVQPGGSLRLSCAASGLTFSDYSMSWYRQAPGKGR

ELVAIISGSGVITHYVDSVKGRFTISRDNAKNTLYLQMRSLRAED

TAVYYCRAVSDWEDYWGQGTQVTVSSGGGGSGGGGSEVQLVESGG

GLVQPGGSLRLSCAASGFTFSGDCMGWFRQAPGKGLDEGVATIDN

AGRIKYADSVKGRFTISRDNAKNSLYLQMNSLRAEDTAVYYCAAG

WTFGGQCSPADWGQGTQVTVSSGGGGSGGGGSEVQLVQSGAEVKK

PGASVKVSCKASGYTFTNYWMHWVRQAPGQGLEWMGRIDPDSTGS

KYNEKFKTRVTMTRDTSTSTVYMELSSLRSEDTAVYYCAREGAYG

YYFDYWGQGTLVTVSS*ASTKGPSVFPLAPCSRSTSESTAALGCLV*

*KDYFPEPVTVSWNSGALTSGVHTFPAVLQSSGLYSLSSVVTVPSS*

*SLGTKTYTCNVDHKPSNTKVDKRVESKYGPPCPPCPAPEFLGGPS*

*VFLFPPKPKDTLMISRTPEVTCVVVDVSQEDPEVQFNWYVDGVEV*

*HNAKTKPREEQFNSTYRVVSVLTVLHQDWLNGKEYKCKVSNKGLP*

-continued

SLSASVGDRVTITCRASENIYSYLAWYQQKPGKSPKLLIYNARTL

AEGVPSRFSGSGSGTDFTLTISSLQPEDFATYYCQYHSGSPLPFG

GGTKVEIK*RTVAAPSVFIFPPSDEQLKSGTASVVCLLNNFYPREA*

*KVQWKVDNALQSGNSQESVTEQDSKDSTYSLSSTLTLSKADYEKH*

*KVYACEVTHQGLSSPVTKSFNRGEC.*

> The first polypeptide chain of A17m0902-1708-30H2-C
(SEQ ID NO: 89)

EVQLVESGGGLVQPGGSLRLSCAASGFTFSGDCMGWFRQAPGKGL

DEGVATIDNAGRIKYADSVKGRFTISRDNAKNSLYLQMNSLRAED

TAVYYCAAGWTFGGQCSPADWGQGTQVTVSSGGGGSGGGGSEVQL

VQSGAEVKKPGASVKVSCKASGYTFTNYWMHWVRQAPGQGLEWMG

RIDPDSTGSKYNEKFKTRVTMTRDTSTSTVYMELSSLRSEDTAVY

YCAREGAYGYYFDYWGQGTLVTVSS*ASTKGPSVFPLAPCSRSTSE*

*STAALGCLVKDYFPEPVTVSWNSGALTSGVHTFPAVLQSSGLYSL*

*SSVVTVPSSSLGTKTYTCNVDHKPSNTKVDKRVESKYGPPCPPCP*

*APEFLGGPSVFLFPPKPKDTLMISRTPEVTCVVVDVSQEDPEVQF*

*NWYVDGVEVHNAKTKPREEQFNSTYRVVSVLTVLHQDWLNGKEYK*

*CKVSNKGLPSSIEKTISKAKGQPREPQVYTLPPSQEEMTKNQVSL*

*TCLVKGFYPSDIAVEWESNGQPENNYKTTPPVLDSDGSFFLYSRL*

-continued

*TVDKSRWQEGNVFSCSVMHEALHNHYTQKSLSLSLGK*GGGGSGGGGSEVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSS.

The second polypeptide chain of A17m0902-1708-30H2-C is set forth in SEQ ID NO: 68.

The first polypeptide chain of A17m0902-1708-30H2-D is set forth in SEQ ID NO: 84.

> The second polypeptide chain of A17m0902-1708-30H2-D
(SEQ ID NO: 90)
DIQMTQSPSSLSASVGDRVTITCRASENIYSYLAWYQQKPGKSPKLLIYNARTLAEGVPSRFSGSGSGTDFTLTISSLQPEDFATYYCQYHSGSPLPFGGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*GGGGSGGGGSEVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSS > The first polypeptide chain of A17m0902-1708-151H7-A
(SEQ ID NO: 91)
EVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSSGGGGSGGGGSHVQLVESGGGLVQPGGSLRLSCVASASGFTYRPYCMAWFRQAPGKEREAVAGIDIFGGTTYADSVKGRFTASRDNAGFSLYLQMNSLRAEDTAVYYCAAGDSPDGRCPPLGQGLNYWGQGTMVTVSSGGGGSGGGGSEVQLVQSGAEVKKPGASVKVSCKASGYTFTNYWMHWVRQAPGQGLEWMGRIDPDSTGSKYNEKFKTRVTMTRDTSTSTVYMELSSLRSEDTAVYYCAREGAYGYYFDYWGQGTLVTVSS*ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK.*

The second polypeptide chain of A17m0902-1708-151H7-A is set forth in SEQ ID NO: 68.

The first polypeptide chain of A17m0902-1708-151H7-B is set forth in SEQ ID NO: 85.

> The second polypeptide chain of A17m0902-1708-151H7-B
(SEQ ID NO: 92)
EVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSSGGGGSGGGGSDIQMTQSPSSLSASVGDRVTITCRASENIYSYLAWYQQKPGKSPKLLIYNARTLAEGVPSRFSGSGSGTDFTLTISSLQPEDFATYYCQYHSGSPLPFGGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC.*

> The first polypeptide chain of A17m0902-1708-151H7-C
(SEQ ID NO: 93)
HVQLVESGGGLVQPGGSLRLSCVASASGFTYRPYCMAWFRQAPGKEREAVAGIDIFGGTTYADSVKGRFTASRDNAGFSLYLQMNSLRAEDTAVYYCAAGDSPDGRCPPLGQGLNYWGQGTMVTVSSGGGGSGGGGSEVQLVQSGAEVKKPGASVKVSCKASGYTFTNYWMHWVRQAPGQGLEWMGRIDPDSTGSKYNEKFKTRVTMTRDTSTSTVYMELSSLRSEDTAVYYCAREGAYGYYFDYWGQGTLVTVSS*ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK*GGGGSGGGGSEVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSS.

The second polypeptide chain of A17m0902-1708-151H7-C is set forth in SEQ ID NO: 68.

The first polypeptide chain of A17m0902-1708-151H7-D is set forth in SEQ ID NO: 85.

> The second polypeptide chain of A17m0902-1708-151H7-D
(SEQ ID NO: 94)
DIQMTQSPSSLSASVGDRVTITCRASENIYSYLAWYQQKPGKSPKLLIYNARTLAEGVPSRFSGSGSGTDFTLTISSLQPEDFATYYCQYHSGSPLPFGGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*GGGGSGGGGSEVQLVESGGGLVQPGGSLRLSCAASGLTFSDYSMSWYRQAPGKGRELVAIISGSGVITHYVDSVKGRFTISRDNAKNTLYLQMRSLRAEDTAVYYCRAVSDWEDYWGQGTQVTVSS.

After cell transfection, expression, and purification by conventional methods, the antibodies of interest can be obtained.

Example 3-2. Binding Affinities of Anti-PD-1/PVRIG/TIGIT Trispecific Antibodies for Antigens ELISA assays were performed. TIGIT or PVRIG protein (his tag, Acrobiosystems, PVG-H52H4) was dissolved in PBS to 1 μg/mL, and the solution was added to a 96-well plate at 100 μL/well. The plate was coated with the antigen overnight at 4° C. The plate was washed with PBST solution three times. PBST/1% BSA solution was added, and the plate was incubated at 37° C. for 1 h for blocking. After three washes with PBST solution, different concentrations of the trispecific antibodies (diluted with PBST/1% BSA solution) were added, and the plate was incubated at 37° C. for 1.5 h. The plate was washed with PBST solution three times. 100 μL of HRP-conjugated anti-human IgG4 Fc secondary antibody (Thermo) solution was added, and the plate was incubated at 37° C. for 1 h. After three washes with PBST solution, TMB solution was added at 100 μL/well. After 5 min of reaction at room temperature, 50 μL of stop solution was added. OD450 values were measured using a microplate reader, and $EC_{50}$ was calculated.

1. Binding to TIGIT

Figure 9A:
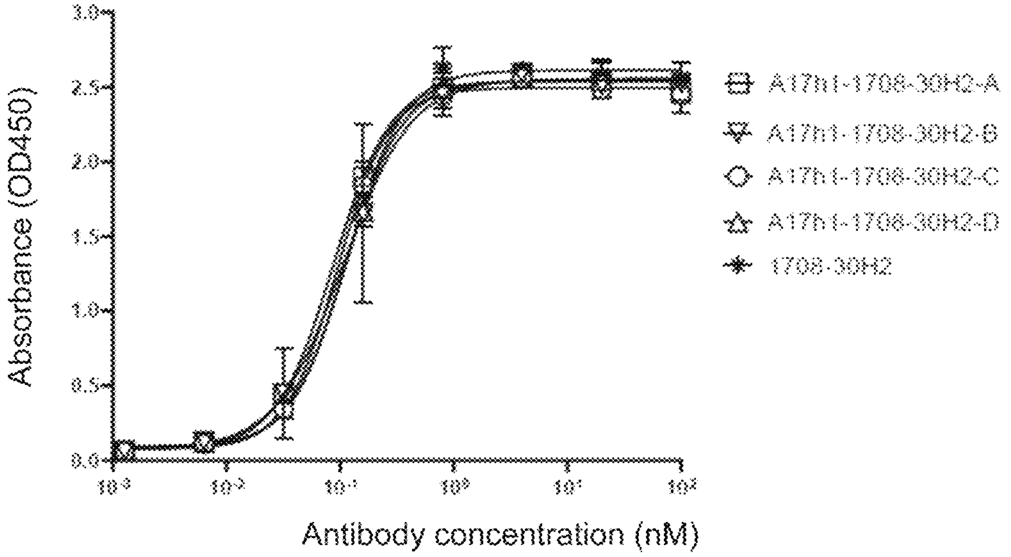
FIGS. 9A to 9B show the results of measuring the binding of A17h1-1708-30H2 and A17h1-1708-151H7 antibodies of 4 configurations to TIGIT antigen, respectively.
Figure 9B:
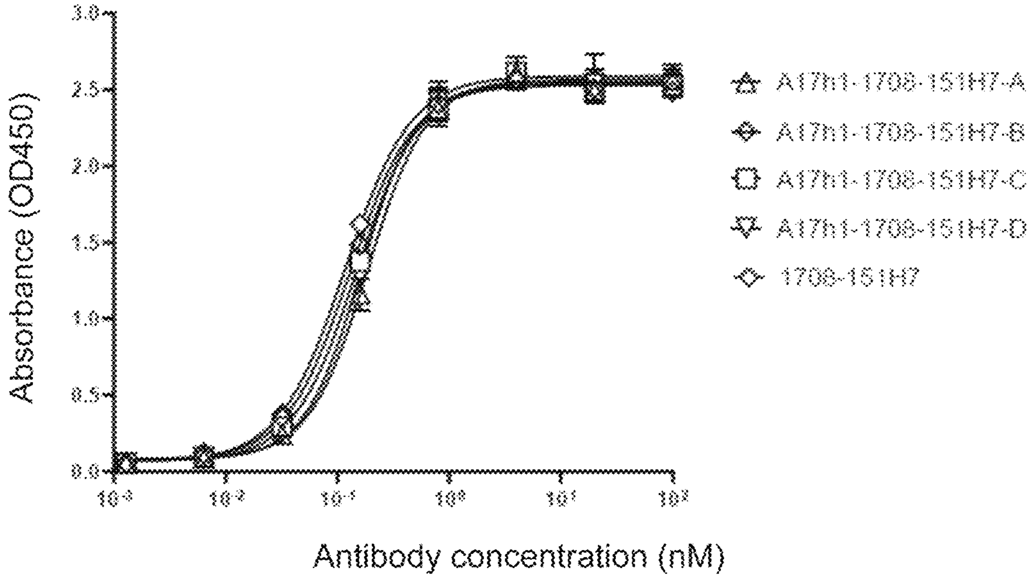

The A17h1-1708-30H2 and A17h1-1708-151H7 trispecific antibodies of the four configurations can all form strong binding to TIGIT, and their binding capacities are similar to each other and to those of the bispecific antibodies 1708-30H2 and 1708-151H7 to TIGIT. The results are shown in FIGS. 9A and 9B and Table 38. Thus, all the trispecific antibody configurations do not affect their binding to TIGIT.

TABLE 38

The $EC_{50}$ values of trispecific antibodies binding to TIGIT antigen

| Antibody No. | $EC_{50}$ (nM) of binding to human TIGIT |
|---|---|
| A17h1-1708-30H2-A | 0.08749 |
| A17h1-1708-30H2-B | 0.1071 |
| A17h1-1708-30H2-C | 0.09511 |
| A17h1-1708-30H2-D | 0.1125 |
| 1708-30H2 | 0.1156 |
| 1708-151H7 | 0.1175 |
| A17h1-1708-151H7-A | 0.1859 |
| A17h1-1708-151H7-B | 0.1293 |
| A17h1-1708-151H7-C | 0.148 |
| A17h1-1708-151H7-D | 0.1624 |

2. Binding to PVRIG

Figure 10A:
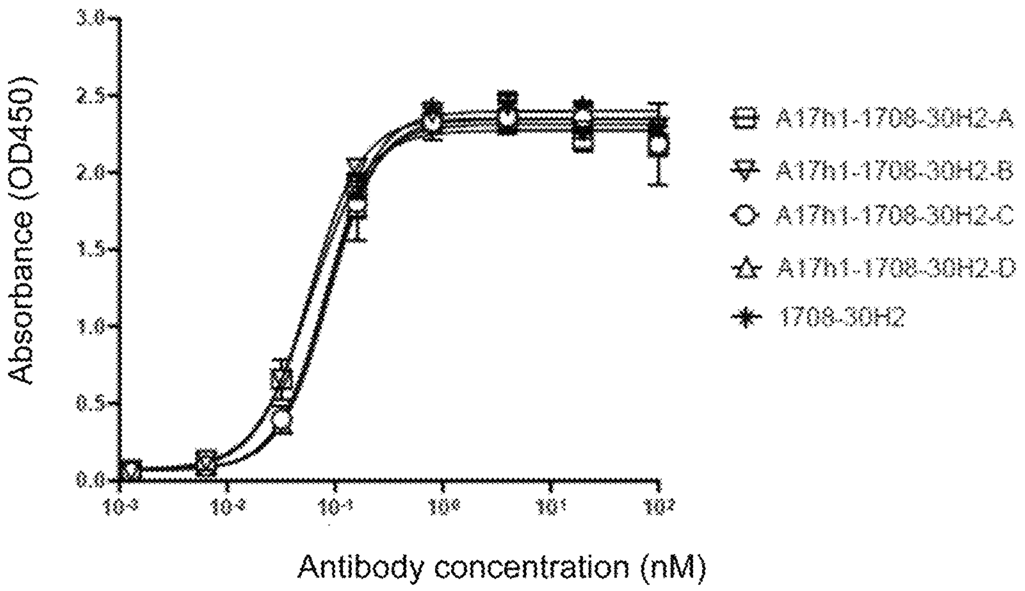
FIGS. 10A to 10B show the results of measuring the binding of A17h1-1708-30H2 and A17h1-1708-151H7 antibodies of 4 configurations to PVRIG antigen, respectively.
Figure 10B:
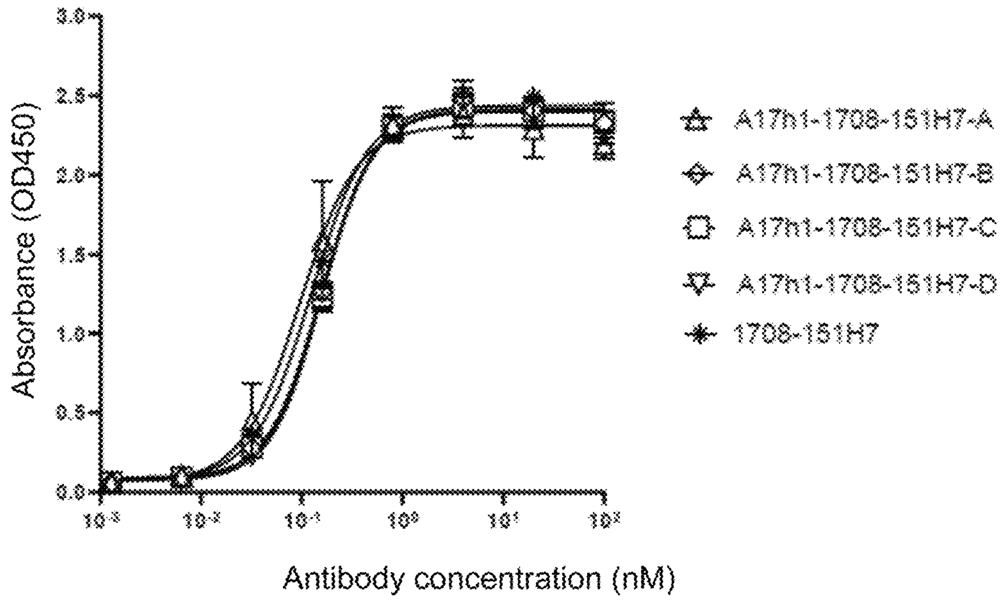

The A17h1-1708-30H2 and A17h1-1708-151H7 trispecific antibodies of the four configurations can all form strong binding to PVRIG, and their binding capacities are similar to each other and to those of the bispecific antibodies 1708-30H2 and 1708-151H7 to PVRIG. See Table 39 and FIGS. 10A and 10B. Thus, all the trispecific antibody configurations do not affect their binding to PVRIG.

TABLE 39

The $EC_{50}$ values of trispecific antibodies binding to PVRIG antigen

| Antibody No. | $EC_{50}$ (nM) of binding to human PVRIG |
|---|---|
| A17h1-1708-30H2-A | 0.05891 |
| A17h1-1708-30H2-B | 0.05834 |
| A17h1-1708-30H2-C | 0.08216 |
| A17h1-1708-30H2-D | 0.08852 |
| 1708-30H2 | 0.08462 |
| 1708-151H7 | 0.1249 |
| A17h1-1708-151H7-A | 0.09519 |
| A17h1-1708-151H7-B | 0.1543 |
| A17h1-1708-151H7-C | 0.1596 |
| A17h1-1708-151H7-D | 0.1578 |

Example 3-3: Optimization of PVRIG Sequences of Anti-PD-1/PVRIG/TIGIT Trispecific Antibodies In the design of the PD-1/PVRIG/TIGIT trispecific antibody A17m0902-1708-151H7-C, the first-position amino acid of the original PVRIG antibody sequence (151H7) is a histidine (the single-letter abbreviation for which is H). The histidine at the N-terminus of the trispecific antibody molecular sequence may undergo a pyridoxal phosphate modification and, following phosphorylation, a pyridoxal modification in the actual antibody production process, and therefore the first-position histidine of the original PVRIG sequence needs to be mutated. Since glutamic acid (the single-letter abbreviation for which is E) and glutamine (the single-letter abbreviation for which is Q) are the most frequently occurring amino acids at the first positions of the nanobody sequences, H was mutated into E or Q. The mutated sequence of the PVRIG antibody 151H7 is as follows:

```
> 151H7 H1E
                                              (SEQ ID NO: 95)
EVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSS.

> 151H7 H1Q
                                              (SEQ ID NO: 96)
QVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSS.
```

The trispecific antibody molecule obtained by changing the first-position amino acid of the sequence of the PVRIG antibody (151H7) from H to E is named A17m0902-1708-151H7-01-C; the trispecific antibody molecule obtained by changing the first-position amino acid of the PVRIG (151H7) sequence from H to Q is named A17m0902-1708-151H7-02-C.

The molecules A17m0902-1708-151H7-01-C and A17m0902-1708-151H7-02-C are of type C—the anti-PVRIG antibodies are linked to the N-termini of the heavy chains of the anti-TIGIT antibody by linkers 1, and the anti-PD-1 antibodies are linked to the C-termini of the heavy chains of the anti-TIGIT antibody by linkers 2 (C of FIG. 8). The polypeptide chain sequences of A17m0902-1708-151H7-01-C and A17m0902-1708-151H7-02-C are as follows:

> The first polypeptide chain
of A17m0902-1708-151H7-01-C
(SEQ ID NO: 97)

EVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSSGGGGSGGG

GSEVQLVQSGAEVKKPGASVKVSCKASGYTFTNYWMHWVRQAPGQ

GLEWMGRIDPDSTGSKYNEKFKTRVTMTRDTSTSTVYMELSSLRS

EDTAVYYCAREGAYGYYFDYWGQGTLVTVSS*ASTKGPSVFPLAPC*

*SRSTSESTAALGCLVKDYFPEPVTVSWNSGALTSGVHTFPAVLQS*

*SGLYSLSSVVTVPSSSLGTKTYTCNVDHKPSNTKVDKRVESKYGP*

*PCPPCPAPEFLGGPSVFLFPPKPKDTLMISRTPEVTCVVVDVSQE*

*DPEVQFNWYVDGVEVHNAKTKPREEQFNSTYRVVSVLTVLHQDWL*

*NGKEYKCKVSNKGLPSSIEKTISKAKGQPREPQVYTLPPSQEEMT*

*KNQVSLTCLVKGFYPSDIAVEWESNGQPENNYKTTPPVLDSDGSF*

*FLYSRLTVDKSRWQEGNVFSCSVMHEALHNHYTQKSLSLSLGK*GG

GGSGGGGSEVQLVESGGGLVQPGGSLRLSCAASGLTFSDYSMSWY

RQAPGKGRELVAIISGSGVITHYVDSVKGRFTISRDNAKNTLYLQ

MRSLRAEDTAVYYCRAVSDWEDYWGQGTQVTVSS.

The second polypeptide chain of A17m0902-1708-151H7-01-C is set forth in SEQ ID NO: 68.

> The first polypeptide chain
of A17m0902-1708-151H7-02-C
(SEQ ID NO: 98)

QVQLVESGGGLVQPGGSLRLSCVASASGFTYRPYCMAWFRQAPGK

EREAVAGIDIFGGTTYADSVKGRFTASRDNAGFSLYLQMNSLRAE

DTAVYYCAAGDSPDGRCPPLGQGLNYWGQGTMVTVSSGGGGSGGG

GSEVQLVQSGAEVKKPGASVKVSCKASGYTFTNYWMHWVRQAPGQ

GLEWMGRIDPDSTGSKYNEKFKTRVTMTRDTSTSTVYMELSSLRS

EDTAVYYCAREGAYGYYFDYWGQGTLVTVSS*ASTKGPSVFPLAPC*

*SRSTSESTAALGCLVKDYFPEPVTVSWNSGALTSGVHTFPAVLQS*

*SGLYSLSSVVTVPSSSLGTKTYTCNVDHKPSNTKVDKRVESKYGP*

*PCPPCPAPEFLGGPSVFLFPPKPKDTLMISRTPEVTCVVVDVSQE*

*DPEVQFNWYVDGVEVHNAKTKPREEQFNSTYRVVSVLTVLHQDWL*

*NGKEYKCKVSNKGLPSSIEKTISKAKGQPREPQVYTLPPSQEEMT*

*KNQVSLTCLVKGFYPSDIAVEWESNGQPENNYKTTPPVLDSDGSF*

*FLYSRLTVDKSRWQEGNVFSCSVMHEALHNHYTQKSLSLSLGK*GG

GGSGGGGSEVQLVESGGGLVQPGGSLRLSCAASGLTFSDYSMSWY

RQAPGKGRELVAIISGSGVITHYVDSVKGRFTISRDNAKNTLYLQ

MRSLRAEDTAVYYCRAVSDWEDYWGQGTQVTVSS.

The second polypeptide chain of A17m0902-1708-151H7-02-C is set forth in SEQ ID NO: 68.

Example 3-4. Binding Affinities of Anti-PD-1/PVRIG/TIGIT Trispecific Antibodies with Optimized PVRIG Sequences for Antigens A stably transfected HEK293F cell strain expressing the human PVRIG gene, a stably transfected CHO-K1 cell strain expressing the human TIGIT gene, and Jurkat cells expressing human PD-1 were used. The cell strain was inoculated into a 96-well plate at $2\times10^5$ cells/well. The plate was centrifuged at 300 g for 5 min, and the supernatant was removed. 100 μL of test antibody was added, and the plate was incubated at 4° C. for 1 h. The plate was centrifuged, and the supernatant was removed. The plate was washed 3 times with 200 μL of wash buffer (PBS+2% FBS), and 100 μL of an Alexa Fluor 488-labeled anti-human IgG secondary antibody (Invitrogen, A-11013) diluted at 1:500 was added. The plate was incubated at 4° C. for 1 h. The plate was centrifuged, and the supernatant was removed. The plate was washed 3 times with 200 μL of wash buffer (PBS+2% FBS). The cells were resuspended in 100 μL of PBS and tested on a flow cytometer (BD FACS Calibur or BD FACS Canto_II).

1. Binding to PVRIG

Figure 11A:
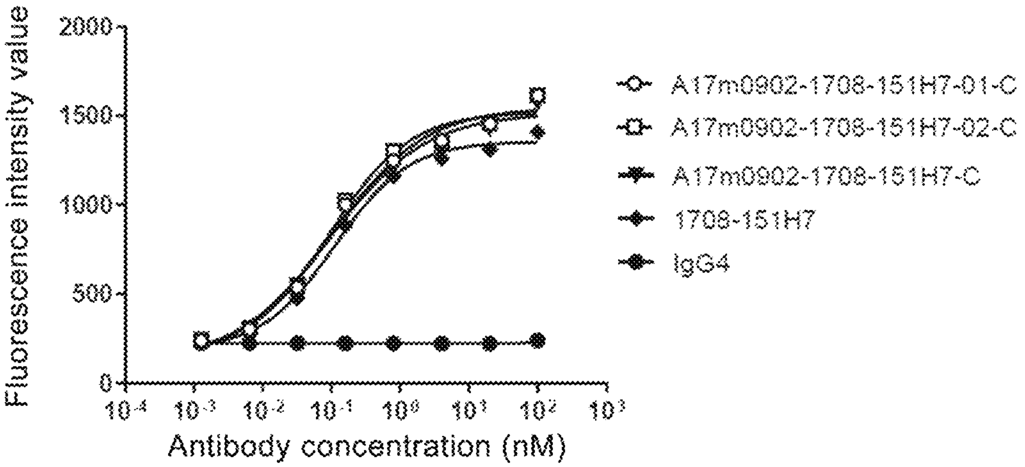

The two trispecific antibody molecules A17m0902-1708-151H7-01-C and A17m0902-1708-151H7-02-C obtained by mutation of the first-position amino acid of the PVRIG antibody showed relatively similar activity to the original trispecific antibody molecule A17m0902-1708-151H7-C and the original bispecific antibody molecule 1708-151H7 in binding to human PVRIG expressed on cell surfaces; their EC50 values are similar, indicating that the mutation of the first-position amino acid of the PVRIG antibody did not affect the binding of the trispecific antibodies to PVRIG. The results are shown in Tables 40 and FIG. 11A.

TABLE 40

The $E_{MAX}$ and $EC_{50}$ of antibodies binding to cells expressing human PVRIG

| Antibody | $E_{MAX}$ | $EC_{50}$ (nM) |
|---|---|---|
| A17m0902-1708-151H7-01-C | 1547 | 0.1048 |
| A17m0902-1708-151H7-02-C | 1521 | 0.09636 |
| A17m0902-1708-151H7-C | 1516 | 0.0944 |
| 1708-151H7 | 1357 | 0.1124 |

2. Binding to TIGIT

Figure 11B:
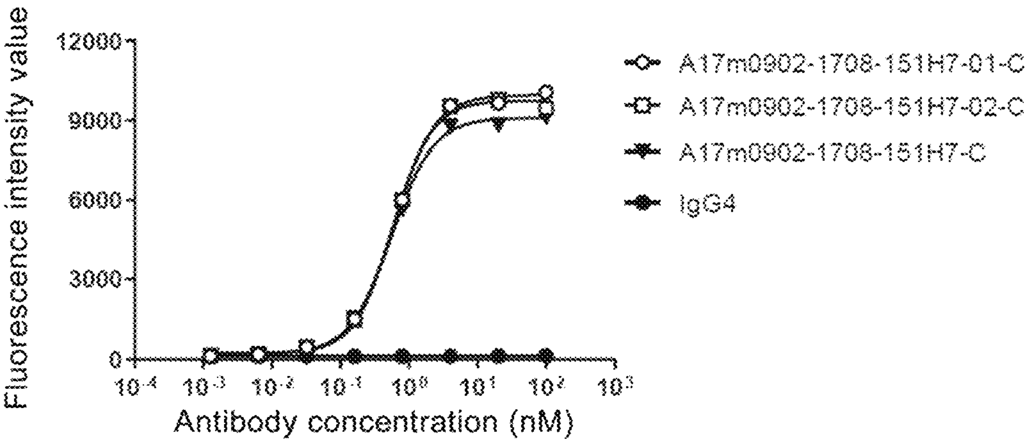

The two trispecific antibody molecules A17m0902-1708-151H7-01-C and A17m0902-1708-151H7-02-C showed relatively similar activity to the original trispecific antibody molecule A17m0902-1708-151H7-C in binding to human TIGIT expressed on cell surfaces; their EC50 values are similar, indicating that the mutation of the first-position amino acid of the PVRIG antibody did not affect the binding of the trispecific antibodies to TIGIT. The results are shown in Tables 41 and FIG. 11B.

TABLE 41

The $E_{MAX}$ and $EC_{50}$ of trispecific antibodies binding to cells expressing human TIGIT

| Antibody | $E_{MAX}$ | $EC_{50}$ (nM) |
|---|---|---|
| A17m0902-1708-151H7-01-C | 9964 | 0.6008 |
| A17m0902-1708-151H7-02-C | 9747 | 0.586 |
| A17m0902-1708-151H7-C | 9105 | 0.5577 |

3. Binding to PD-1

Figure 11C:
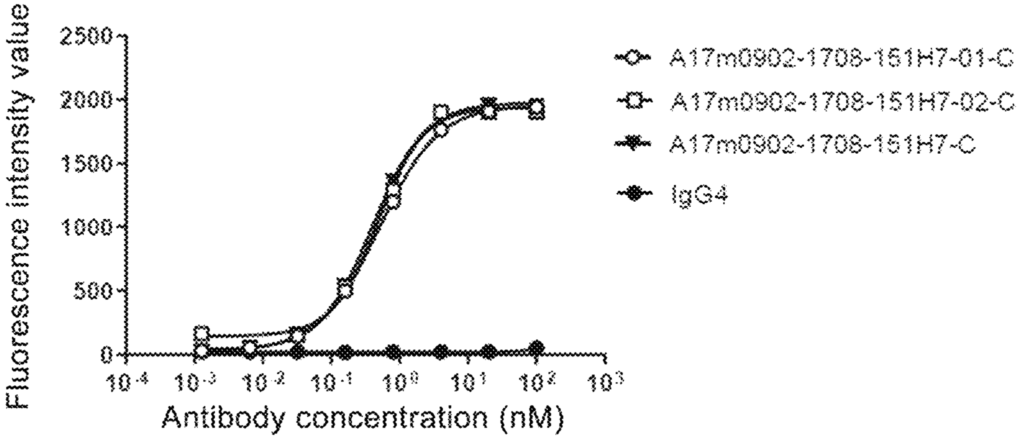

The two trispecific antibody molecules A17m0902-1708-151H7-01-C and A17m0902-1708-151H7-02-C showed similar activity to the original antibody A17m0902-1708-151H7-C in binding to human PD-1 expressed on cell surfaces; their EC50 values are similar, indicating that the mutation of the first-position amino acid of the PVRIG antibody did not affect the binding of the trispecific antibodies to PD-1. The results are shown in Tables 42 and FIG. 11C.

TABLE 42

The EMAX and $EC_{50}$ of trispecific antibodies binding to cells expressing human PD-1

| Antibody | $E_{MAX}$ | $EC_{50}$ (nM) |
|---|---|---|
| A17m0902-1708-151H7-01-C | 1956 | 0.5027 |
| A17m0902-1708-151H7-02-C | 1937 | 0.4806 |
| A17m0902-1708-151H7-C | 1974 | 0.4006 |

It can be concluded from the above binding activity results that the affinities of the two trispecific antibody molecules A17m0902-1708-151H7-01-C and A17m0902-1708-151H7-02-C obtained by mutation of the first-position amino acid of the PVRIG antibody for PVRIG, TIGIT, and PD-1 antigens expressed on cell surfaces are similar to those of the parent antibody A17m0902-1708-151H7-C; these mutations did not affect the binding of the trispecific antibodies to PVRIG, TIGIT, and PD-1.

Figure 12A:
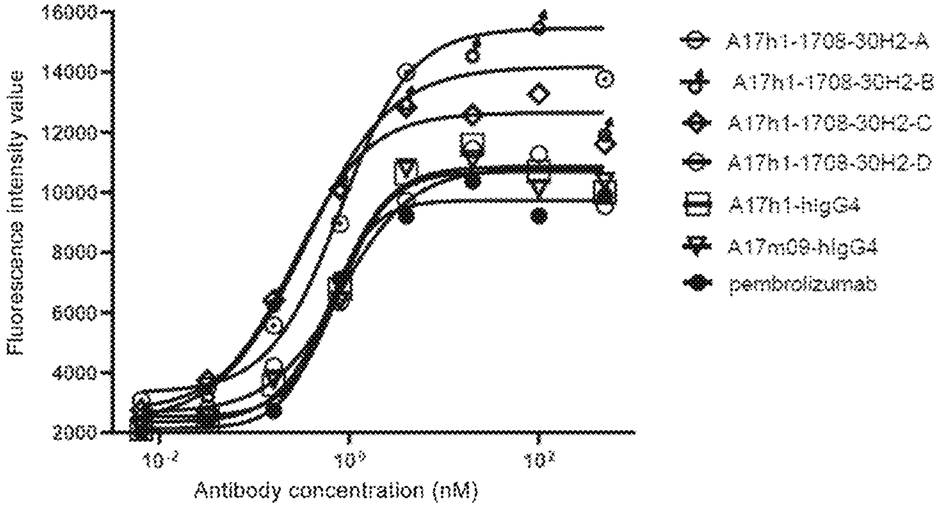
FIGS. 12A to 12B show the blocking of PD-L1/PD-1 binding in a PD-1/PD-L1 NFAT reporter gene system by A17h1-1708-30H2 and A17h1-1708-151H7 antibodies of 4 configurations, respectively.
Figure 12B:
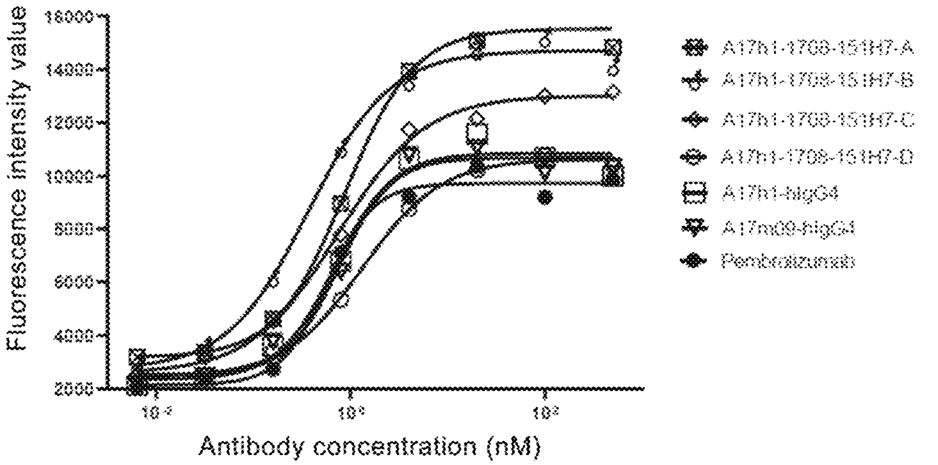

Example 3-5. PD-1/PD-L1 Reporter Gene System Test of Blocking of PD-1 by Anti-PD-1/PVRIG/TIGIT Trispecific Antibodies A test was performed using the method of Example 1-4. As shown in FIGS. 12A and 12B and Table 43, all the trispecific antibodies of the four configurations formed using A17h1 as a PD-1 end can block PD-1, and the reporter gene activity of the type B and type C trispecific antibodies is better.

TABLE 43

The NFAT reporter gene system $IC_{50}$ values of trispecific antibodies

| Antibody No. | IC50 (nM) |
|---|---|
| A17h1-1708-30H2-A | 0.8007 |
| A17h1-1708-30H2-B | 0.3436 |
| A17h1-1708-30H2-C | 0.2643 |
| A17h1-1708-30H2-D | 0.825 |
| A17m09-hIgG4 | 0.7716 |
| A17h1-hIgG4 | 0.696 |
| pembrolizumab | 0.573 |

Figure 13A:
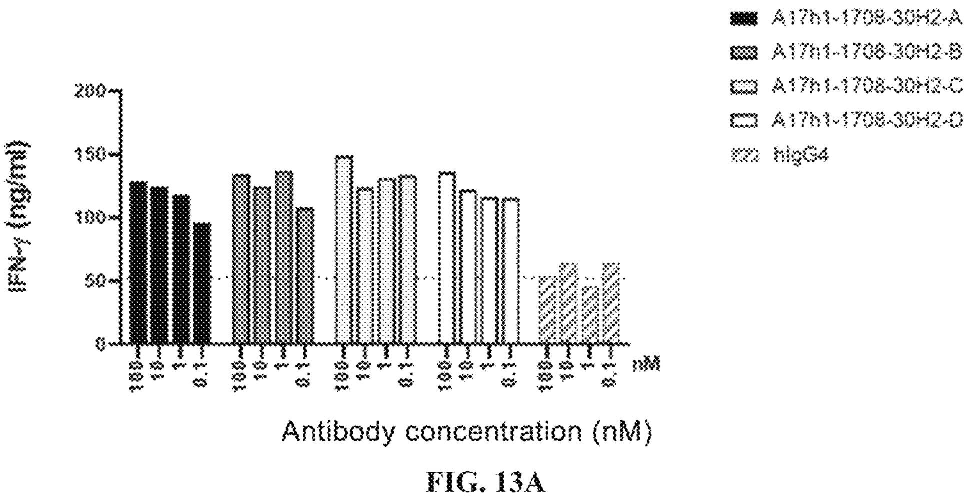
FIGS. 13A to 13B show the MLR test results for A17h1-1708-30H2 and A17h1-1708-151H7 of 4 configurations, respectively.
Figure 13B:
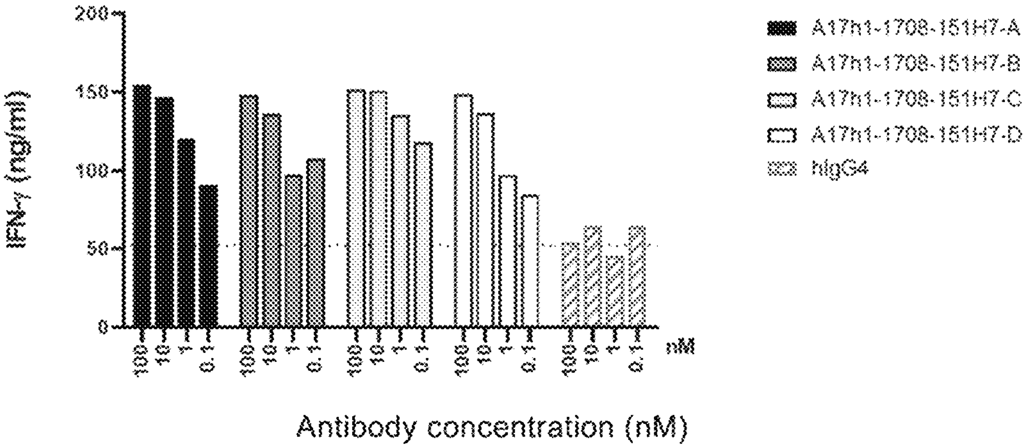

Example 3-6. MLR Tests of Activation of T Cells by Anti-PD-1/PVRIG/TIGIT Trispecific Antibodies Cells from human subjects were subjected to a DC:T mix lymphocyte reaction experiment using the method of Example 1-6, and the results are shown in FIGS. 13A and 13B and Table 44. The results show that the trispecific antibodies of 4 configurations can all effectively promote T cell activation, eliminate PD-1/PD-L1 inhibition, and promote cytokine secretion by T cells, and they all have relatively strong in vitro efficacy and activity.

TABLE 44

The MLR results for trispecific antibodies of the four configurations

| Antibody No. | Antibody concentration (nM) | | | |
|---|---|---|---|---|
| | 100 | 10 | 1 | 0.1 |
| A17h1-1708-30H2-A | 128.3 | 124.2 | 118.2 | 118.2 |
| A17h1-1708-30H2-B | 134.1 | 124.8 | 136.9 | 107.8 |
| A17h1-1708-30H2-C | 148.8 | 123.3 | 131.2 | 133.2 |
| A17h1-1708-30H2-D | 135.5 | 121.8 | 116 | 115 |
| A17h1-1708-151H7-A | 155.1 | 146.9 | 120.8 | 91.3 |
| A17h1-1708-151H7-B | 148.3 | 136.2 | 97.8 | 107.6 |
| A17h1-1708-151H7-C | 151.6 | 150.9 | 135.6 | 117.8 |
| A17h1-1708-151H7-D | 148.8 | 136.7 | 97.3 | 84.8 |
| hIgG4 | 54.2 | 64.5 | 45.9 | 64.5 |

Figure 14A:
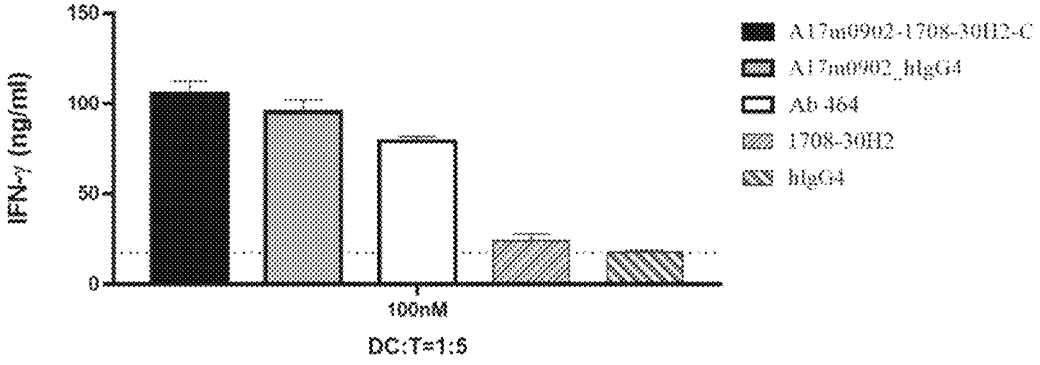
FIGS. 14A to 14B show the MLR test results for A17m0902-1708-30H2-C in two subjects.
Figure 14B:
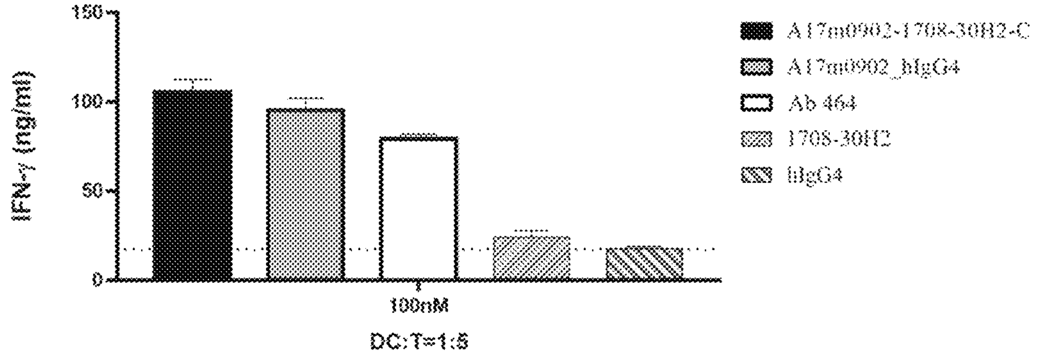

A17m0902-1708-30H2-C, which performed better, was selected and further verified through another DC:T mix lymphocyte reaction experiment. The results in FIGS. 14A and 14B and Tables 45 and 46 show that in activating T cells at an antibody concentration of 100 nM, the trispecific antibody A17m0902-1708-30H2-C is far superior to the bispecific antibody 1708-30H2, is superior to the anti-PD-1 mAb Ab 464, and is slightly superior to the anti-PD-1 mAb A17m0902_hIgG4.

TABLE 45

The MLR test results for subject 1

| Antibody name | IFN-γ (ng/mL): mean ± standard deviation | | | |
|---|---|---|---|---|
| | 100 nM | 10 nM | 1 nM | 0.1 nM |
| A17m0902-1708-30H2-C | 105.6 ± 9.9 | 83 ± 1.9 | 75.4 ± 11.3 | 49.5 ± 11.6 |
| A17m0902_hIgG4 | 95.4 ± 9.6 | 88.3 ± 4.5 | 67.2 ± 2.3 | 45.6 ± 3.0 |
| Ab 464 | 79.2 ± 3.7 | 74.2 ± 4.4 | 66.5 ± 3.2 | 39.2 ± 2.7 |
| 1708-30H2 | 24.2 ± 5.2 | 15.4 ± 4.1 | 16.4 ± 4 | 14.3 ± 4.3 |
| hIgG4 | 17.7 ± 1.8 | 15.4 ± 2.1 | 24.2 ± 6.3 | 14.2 ± 0.5 |

TABLE 46

| The MLR test results for subject 2 | | | | |
|---|---|---|---|---|
| | IFN-γ (ng/mL): mean ± standard deviation | | | |
| Antibody name | 100 nM | 10 nM | 1 nM | 0.1 nM |
| A17m0902-1708-30H2-C | 65.7 ± 7.3 | 58.3 ± 1.6 | 44.2 ± 7 | 27.1 ± 5.6 |
| A17m0902_hIgG4 | 53.6 ± 7.4 | 54.7 ± 0.6 | 40.5 ± 2 | 27.9 ± 1.6 |
| Ab 464 | 52 ± 4.4 | 41.5 ± 4.6 | 33.5 ± 2.9 | 22.1 ± 0.8 |
| 1708-30H2 | 10 ± 2.9 | 10.4 ± 0.4 | 10.3 ± 0.8 | 9.2 ± 4.4 |
| hIgG4 | 7.3 ± 3.0 | 6.1 ± 1.7 | 9.2 ± 3.0 | 8.2 ± 1.3 |

Example 3-7. NK92 Killing Test of Activation of NK Cells by Anti-PD-1/PVRIG/TIGIT Trispecific Antibodies An NK cell killing experiment can be used to test the in vitro efficacy of the anti-PD-1/PVRIG/TIGIT trispecific antibodies. A cell killing experiment was conducted using NK92 cells as effector cells and K562 cells as target cells. First, NK92 cells were co-incubated with different concentrations of a candidate antibody at 37° C. for 30 min. Then, the NK92 cells pre-incubated with the antibody were mixed with CTV (Cat: C34557, Thermo)-labeled K562 cells at an effector-to-target ratio of 10:1, and the mixture was incubated at 37° C. in 1640+10% FBS+10 ng/mL IL-2 for 4 h. After the mixture was centrifuged and the supernatant was removed, the cells were resuspended in a 10 μg/mL propidium iodide solution to stain dead cells. After 10 min of staining at room temperature, the proportion of dead cells (PI positive) among the CTV-labeled K562 cells was measured by FACS, and killing activity was calculated.

Figure 15A:
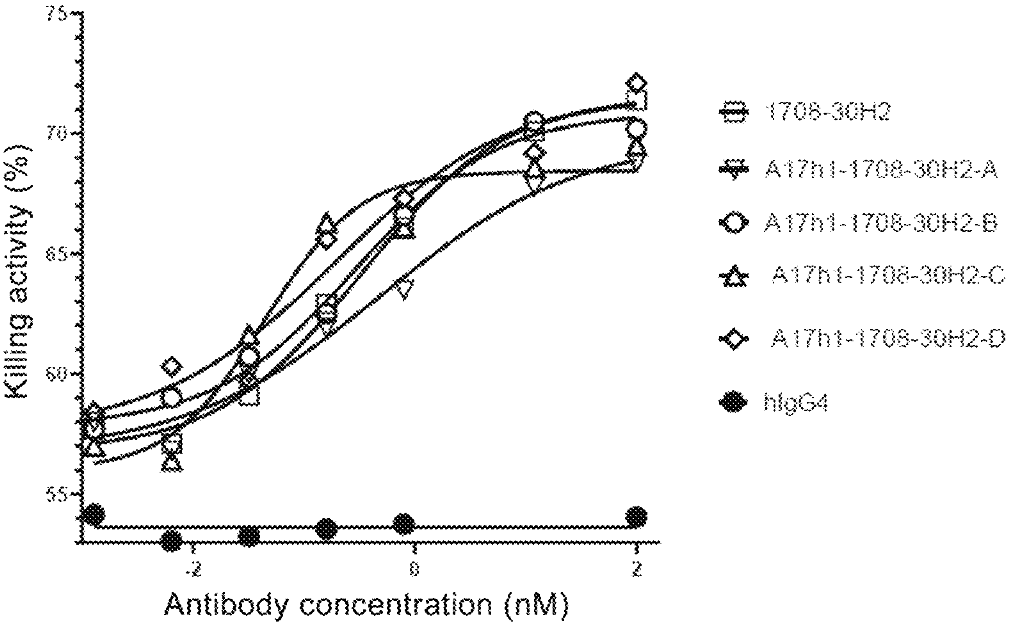
FIGS. 15A to 15B show the results of NK cell killing function experiments for A17h1-1708-30H2 and A17h1-1708-151H7 antibodies of 4 configurations, respectively.
Figure 15B:
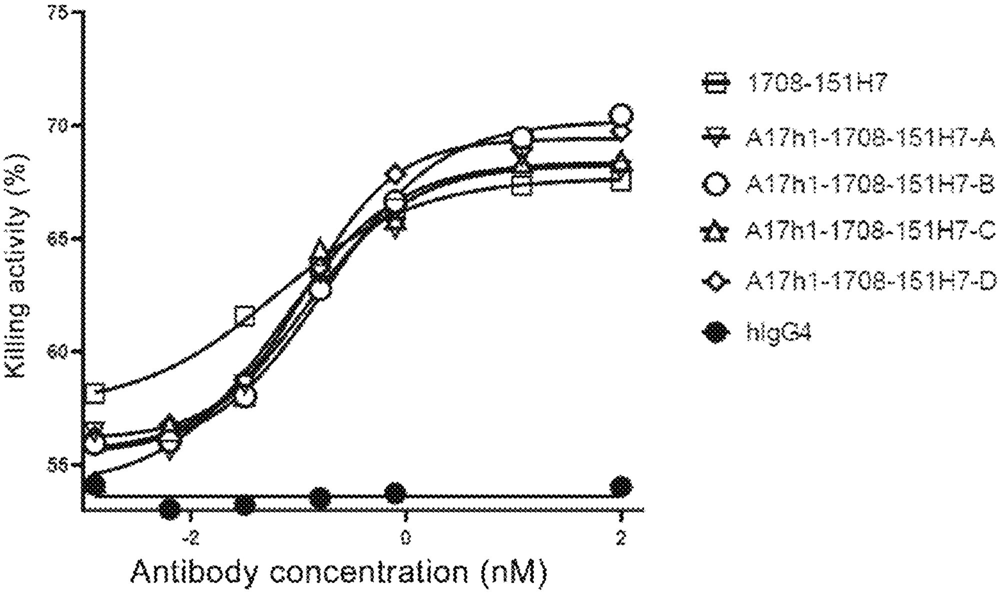

As shown in FIGS. 15A and 15B, the trispecific antibodies retained the anti-PVRIG/TIGIT bispecific antibodies' biological function of promoting NK cell killing, and the $IC_{50}$ values for all the configurations are similar. See Table 47.

TABLE 47

| The NK cell killing function of trispecific antibodies of 4 configurations | |
|---|---|
| Antibody name | $EC_{50}$ (nM) |
| A17h1-1708-151H7 -A | 0.116 |
| A17h1-1708-151H7 -B | 0.182 |
| A17h1-1708-151H7 -C | 0.07 |
| A17h1-1708-151H7 -D | 0.121 |
| 1708-151H7 | 0.066 |
| A17h1-1708-30H2-A | 0.484 |
| A17h1-1708-30H2-B | 0.291 |
| A17h1-1708-30H2-C | 0.044 |
| A17h1-1708-30H2-D | 0.192 |
| 1708-30H2 | 0.325 |

Example 3-8. Evaluation of Anti-Tumor Effect of PD-1/PVRIG/TIGIT Trispecific Antibody on Mouse Subcutaneous Xenograft Tumor Model of Human Melanoma A375 Mixed with Human PBMCs Responsive to PD-1 mAb In this example, the in vivo efficacy of the PD-1/PVRIG/TIGIT trispecific antibody on an in vivo tumor model of human melanoma A375 mixed with human PBMCs responsive to the PD-1 mAb was verified.

NCG mice, female, aged 4-8 weeks, weighing about 18-22 g (the mice were purchased from Jiangsu GemPharmatech Co., Ltd.). The mice were kept in an SPF animal house with an IVC constant-temperature and constant-pressure system.

Donor PBMCs responsive to the PD-1 mAb in the in vivo efficacy model were selected from frozen PBMCs and counted. The PBMCs were resuspended to a certain concentration in RPMI 1640 medium containing IL-2 and 10% FBS. The PBMCs were added to A375 cells which had been treated with Mitomycin C for 2 h. PBMCs were harvested after 5 days of co-culture with A375. A375 cells were cultured in DMEM medium containing 10% fetal bovine serum (FBS), and freshly digested A375 cells were harvested. Each mouse was inoculated with $5\times10^5$ PBMCs and $4\times10^6$ A375 cells; the inoculation volume was 0.2 mL/mouse (containing 50% Matrigel); the cells were inoculated subcutaneously into the right side of female NCG mice. The day of the inoculation was day 0, and at day 1, the mice were randomized into groups according to body weight and dosed.

Given that the molecular weight of A17m0902_hIgG4 is 76 kDa; the molecular weight of 1708-151H7 is 173.5 kDa; and the molecular weight of A17m0902-1708-151H7-C is 200 kDa, an equimolar administration regimen was designed. The administration regimen, the doses, and the route of administration are detailed in Table 48.

TABLE 48

| The experimental groups of mice and the administration regimen | | | | |
|---|---|---|---|---|
| Group | Drug or control | N | Dose (mg/kg) | Frequency of administration (Route of administration) |
| Group 1 | Blank control | 7 | 10 | BIW * 8 |
| Group 2 | 1708-151H7 | 7 | 11.5 | (i.p.) |
| Group 3 | A17m0902_hIgG4 | 7 | 5 | |
| Group 4 | 1708-151H7 + A17m0902-hIgG4 | 7 | 11.5 + 5 | |
| Group 5 | A17m0902-1708-151H7-C | 7 | 13.3 | |

(Note:

N: the number of animals used; i.p.: intraperitoneal injection; BIW * 8: 2 times weekly, 8 injections in total)

After the start of administration, the body weight and tumor volume of the mice were measured 2 times a week.

After day 21 of administration, the tumor growth inhibition rates (TGI) of the 1708-151H7 (11.5 mg/kg) administration group, the A17m0902_hIgG4 (5 mg/kg) administration group, the A17m0902-1708-151H7-C (13.3 mg/kg) administration group, and the 1708-151H7 (11.5 mg/kg)+A17m0902_hIgG4 (5 mg/kg) administration group were 7.05%, 79.91%, 91.63%, and 88.25%, respectively, as compared to the control group. The efficacy of the administration group of the trispecific antibody A17m0902-1708-151H7-C is significantly better than that of the administration group of the anti-PD-1 mAb A17m0902_hIgG4 and is better than the PVRIG/TIGIT bispecific antibody+PD-1 mAb combination group.

Figure 16A:
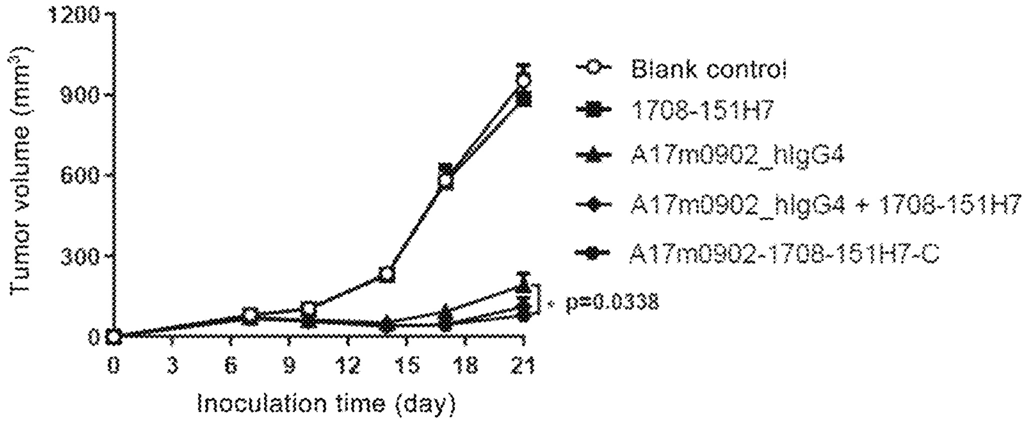
FIGS. 16A to 16B show an evaluation of the anti-tumor effect of an anti-PD-1/PVRIG/TIGIT trispecific antibody on a mouse subcutaneous xenograft tumor model of human melanoma A375 mixed with human PBMCs responsive to the PD-1 mAb.
Figure 16B:
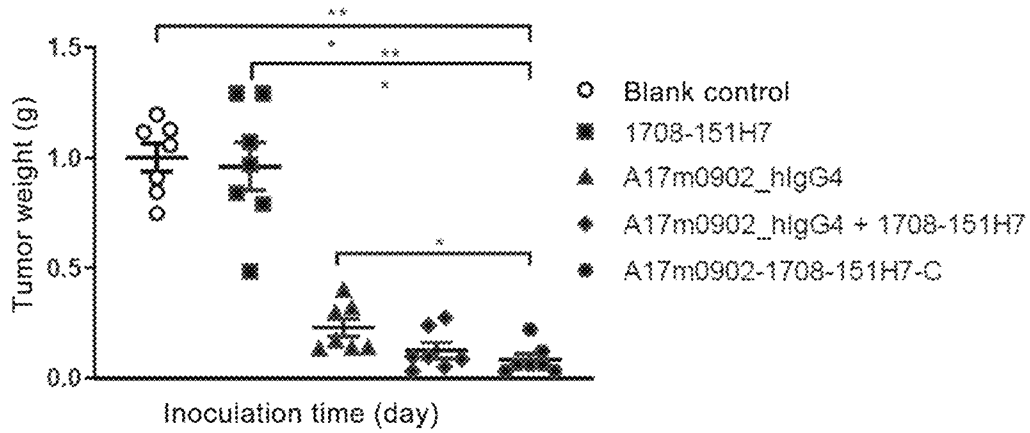

The experiment was ended after day 21 after administration. All the mice were euthanized, and their tumors were separated, weighed, and photographed. The tumor weight TGI was calculated, and it showed a similar trend to the tumor volume TGI. The results also show that the efficacy of the administration group of the trispecific antibody A17m0902-1708-151H7-C is significantly better than that of the administration group of the PD-1 mAb A17m0902_hIgG4 and is better than the PVRIG/TIGIT bispecific antibody+PD-1 mAb combination group. The experimental results are shown in Table 49 and FIGS. 16A and 16B.

TABLE 49

The anti-tumor effect of the anti-PD-1/PVRIG/TIGIT trispecific antibody in the human A375 tumor mouse model responsive to the PD-1 mAb

| Group | Drug | Tumor volume TGI (%) | Tumor weight TGI (%) |
|---|---|---|---|
| 1 | Blank control | / | / |
| 2 | 1708-151H7 | 7.05 | 3.84 |
| 3 | A17m0902_hIgG4 | 79.91 | 77.20 |
| 4 | A17m0902_hIgG4 + 1708-151H7 | 88.25 | 87.60 |
| 5 | A17m0902-1708-151H7-C | 91.63 | 91.50 |

(Note:
N: the number of animals used; i.p.: intraperitoneal injection; BIW: 2 times weekly)

Example 3-9. Evaluation of Anti-Tumor Effect of PD-1/PVRIG/TIGIT Trispecific Antibody on Mouse Subcutaneous Xenograft Tumor Model of Human Melanoma A375 Mixed with Human PBMCs Non-Responsive to PD-1 mAb In this example, the in vivo efficacy of the anti-PD-1/PVRIG/TIGIT trispecific antibody on an in vivo tumor model of human melanoma A375 mixed with human PBMCs non-responsive to the anti-PD-1 mAb was verified.

NCG mice, female, aged 4-8 weeks, weighing about 18-22 g (purchased from Jiangsu GemPharmatech Co., Ltd.) were kept in an SPF animal house with an IVC constant-temperature and constant-pressure system.

Donor PBMCs non-responsive to the anti-PD-1 mAb in the in vivo efficacy model were selected from frozen PBMCs. The experimental protocol was the same as the method described in Example 3-8. The experimental groups of mice and the administration regimen are shown in Table 50.

TABLE 50

The experimental groups of mice and the administration regimen

| Group | Drug or control | N | Dose (mg/kg) | Frequency of administration (Route of administration) |
|---|---|---|---|---|
| Group 1 | Blank control | 7 | 30 | BIW * 8 |
| Group 2 | 1708-151H7 | 7 | 35.8 | (i.p.) |
| Group 3 | A17m0902_hIgG4 | 7 | 15.5 | |
| Group 4 | 1708-151H7 + A17m0902_hIgG4 | | 35.8 + 15.5 | |
| Group 5 | A17m0902-1708-151H7 -C | 7 | 41.3 | |

(Note:
N: the number of animals used; i.p.: intraperitoneal injection; BIW * 8: 2 times weekly, 8 injections in total
)

After the start of administration, the body weight and tumor volume of the mice were measured 2 times a week.

At day 17 after administration, the tumor growth inhibition rates (TGI %) of the experimental groups 1708-151H7, A17m0902_hIgG4, A17m0902-1708-151H7-C, and 1708-151H7+A17m0902_hIgG4 were 4.53%, 20.75%, 36.70%, and 31.95%, respectively, as compared to the IgG control group, according to the measured average tumor volumes of the mice in these groups.

Figure 17A:
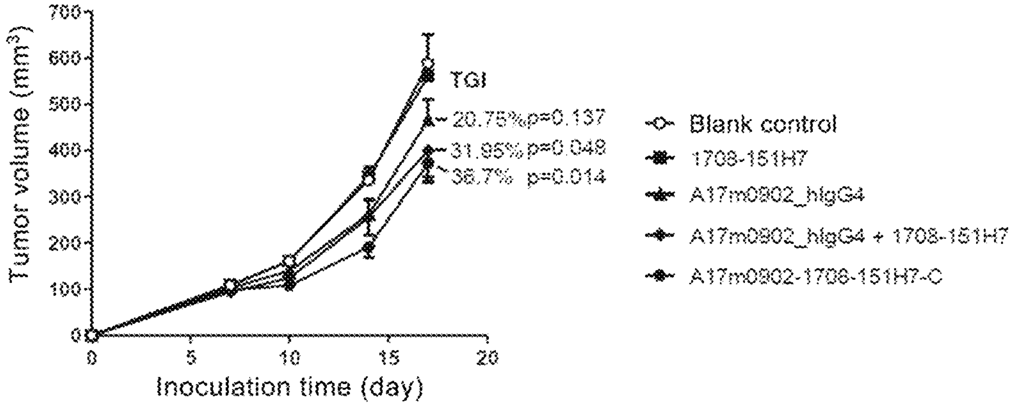
FIGS. 17A to 17B show an evaluation of the anti-tumor effect of an anti-PD-1/PVRIG/TIGIT trispecific antibody on a mouse subcutaneous xenograft tumor model of human melanoma A375 mixed with human PBMCs non-responsive to the PD-1 mAb.
Figure 17B:
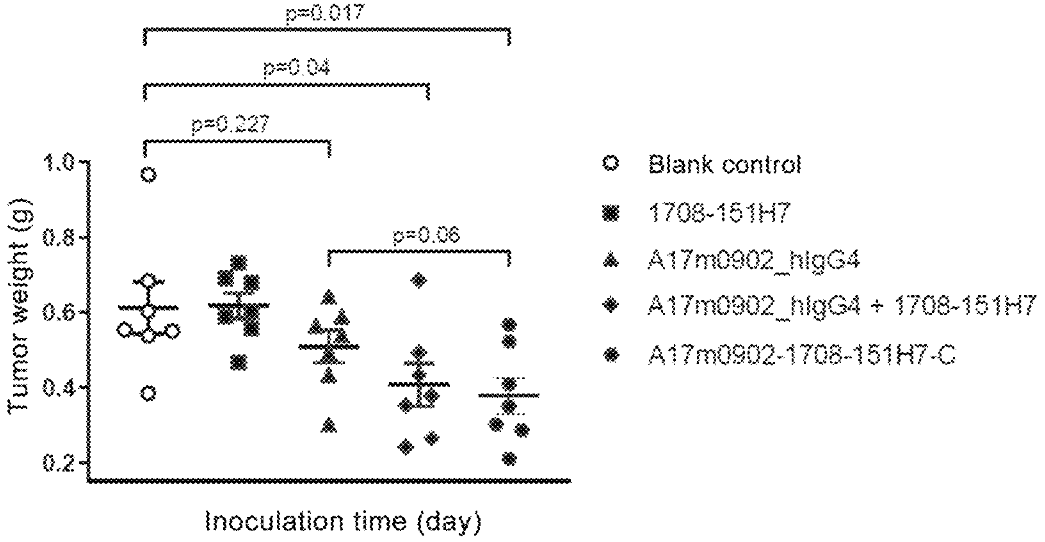

The experiment was ended after day 17 after administration. All the mice were euthanized, and their tumors were separated, weighed, and photographed. The tumor growth inhibition rates (tumor weight TGI %) of the experimental groups 1708-151H7, A17m0902_hIgG4, A17m0902-1708-151H7-C, and 1708-151H7+A17m0902_hIgG4 were 0%, 16.8%, 38.2%, and 33.4%, respectively, as compared to the IgG control group, according to the measured tumor weights of the mice in these groups. The tumor weight TGI showed a similar trend to the tumor volume TGI. The experimental results are shown in Table 51 and FIGS. 17A and 17B.

Compared to the IgG control group, the A17m0902-1708-151H7-C administration group and the 1708-151H7+A17m0902_hIgG4 administration group showed significant reductions in both tumor volume and weight (FIGS. 17A and 17B, $P<0.05$), indicating significant tumor-inhibiting effects. During this experiment, all the mice did not exhibit significant weight losses or behavioral abnormalities, indicating that the mice well tolerated the test drugs under these experimental conditions.

TABLE 51

The anti-tumor effect of the anti-PD-1/PVRIG/TIGIT trispecific antibody in the human A375 tumor mouse model non-responsive to the PD-1 mAb

| Group | Drug | Day 0 Tumor volume ($mm^3$) | Tumor volume at day 17 ($mm^3$) (mean ± standard deviation) | Tumor volume TGI (%) | Tumor weight at day 17 (g) (mean ± standard deviation) | Tumor weight TGI (%) |
|---|---|---|---|---|---|---|
| 1 | Blank control | 0 | 588.39 ± 62.69 | / | 0.611 ± 0.068 | / |
| 2 | 1708-151H7 | 0 | 561.76 ± 31.34 | 4.53 | 0.616 ± 0.034 | 0 |
| 3 | A17m0902_hIgG4 | 0 | 466.28 ± 44.23 | 20.75 | 0.508 ± 0.043 | 16.8 |
| 4 | A17m0902_hIgG4 + 1708-151H7 | 0 | 400.39 ± 57.75 | 31.95* | 0.406 ± 0.057 | 33.4* |
| 5 | A17m0902-1708-151H7-C | 0 | 372.45 ± 40.80 | 36.7* | 0.377 ± 0.049 | 38.2* |

(Note:
*P < 0.05, P < 0.01, and *P < 0.001 are thought to indicate significant differences compared to the control group (hIgG1))

The invention claimed is:

1. A PD-1-binding protein, comprising an immunoglobulin single variable domain, wherein the immunoglobulin single variable domain comprises:
   a CDR1, a CDR2, and a CDR3 from the amino acid sequence set forth in any of SEQ ID NOs: 33, 3, 13-15, 17-32, and 34-35, or a CDR1, a CDR2, and a CDR3 from the amino acid sequence set forth in any of SEQ ID NOs: 2 and 16; the CDR1, CDR2, and CDR3 are defined according to the Kabat, IMGT, Chothia, AbM, or Contact numbering scheme.

2. The PD-1-binding protein according to claim 1, wherein the immunoglobulin single variable domain undergoes a modification selected from any of the following or a combination thereof: humanization, affinity maturation, T cell epitope removal, reduction of antibody deamidation, and reduction of antibody isomerization.

3. The PD-1-binding protein according to claim 1, wherein the amino acid sequence of the immunoglobulin single variable domain:
   is set forth in any of SEQ ID NOs: 33, 3, 13-15, 17-32, and 34-35 or has at least 90% sequence identity thereto; or
   is set forth in any of SEQ ID NOs: 2 and 16 or has at least 90% sequence identity thereto.

4. The PD-1-binding protein according to claim 1, further comprising a human immunoglobulin Fc region.

5. A PD-1/PVRIG/TIGIT-binding protein, comprising:
   a first antigen-binding domain that specifically binds to PD-1,
   a second antigen-binding domain that specifically binds to PVRIG, and
   a third antigen-binding domain that specifically binds to TIGIT,
   wherein the first antigen-binding domain comprises the PD-1-binding protein according to claim 1.

6. The PD-1/PVRIG/TIGIT-binding protein according to claim 5, wherein:
   the second antigen-binding domain comprises an immunoglobulin single variable domain, and the immunoglobulin single variable domain comprises:
   a CDR1, a CDR2, and a CDR3 from the amino acid sequence set forth in any of SEQ ID NOs: 95-96, 45, and 62-66, or a CDR1, a CDR2, and a CDR3 from the amino acid sequence set forth in any of SEQ ID NOs: 44 and 57-61; the CDR1, CDR2, and CDR3 are defined according to the Kabat, IMGT, Chothia, AbM, or Contact numbering scheme.

7. The PD-1/PVRIG/TIGIT-binding protein according to claim 5, wherein:
   the third antigen-binding domain comprises a heavy chain variable region (VH) and a light chain variable region (VL), wherein:
   the VH comprises a HCDR1, a HCDR2, and a HCDR3, the amino acid sequences of which are set forth in SEQ ID NOs: 73, 74, and 75, respectively; the VL comprises a LCDR1, a LCDR2, and a LCDR3, the amino acid sequences of which are set forth in SEQ ID NOs: 76, 77, and 78, respectively.

8. The PD-1/PVRIG/TIGIT-binding protein according to claim 5, wherein:
   the first antigen-binding domain comprises:
   the amino acid sequence set forth in any of SEQ ID NOs: 33, 3, 13-15, 17-32, and 34-35 or an amino acid sequence having at least 90% sequence identity thereto; or the amino acid sequence set forth in any of SEQ ID NOs: 2 and 16 or an amino acid sequence having at least 90% sequence identity thereto.

9. The PD-1/PVRIG/TIGIT-binding protein according to claim 5, wherein:
   the second antigen-binding domain comprises:
   the amino acid sequence set forth in any of SEQ ID NOs: 95-96, 45, and 62-66 or an amino acid sequence having at least 90% sequence identity thereto; or the amino acid sequence set forth in any of SEQ ID NOs: 44 and 57-61 or an amino acid sequence having at least 90% sequence identity thereto.

10. The PD-1/PVRIG/TIGIT-binding protein according to claim 5, wherein:
   the third antigen-binding domain comprises a VH and a VL, wherein:
   the VH comprises the amino acid sequence set forth in any of SEQ ID NOs: 79-81 or an amino acid sequence having at least 90% sequence identity thereto;
   the VL comprises the amino acid sequence set forth in SEQ ID NO: 83 or 82 or an amino acid sequence having at least 90% sequence identity thereto.

11. The PD-1/PVRIG/TIGIT-binding protein according to claim 5, comprising:
   a first polypeptide chain, and
   a second polypeptide chain,
   wherein in order from N-terminus to C-terminus:
   (I) the first polypeptide chain is represented by the following structure: [the first antigen-binding domain]-[linker 1]a-[the second antigen-binding domain]-[linker 2]b-[the VH of the third antigen-binding domain]-CH1-Fc, and
   the second polypeptide chain is represented by the following structure: [the VL of the third antigen-binding domain]-Cκ; or
   (II) the first polypeptide chain is represented by the following structure: [the second antigen-binding domain]-[linker 2]b-[the VH of the third antigen-binding domain]-CH1-Fc, and the second polypeptide chain is represented by the following structure: [the first antigen-binding domain]-[linker 3]c-[the VL of the third antigen-binding domain]-Cκ: or
   (III) the first polypeptide chain is represented by the following structure: [the second antigen-binding domain]-[linker 2]b-[the VH of the third antigen-binding domain]-CH1-Fc-[linker 4]d-[the first antigen-binding domain], and
   the second polypeptide chain is represented by the following structure: [the VL of the third antigen-binding domain]-Cκ; or
   (IV) the first polypeptide chain is represented by the following structure: [the second antigen-binding domain]-[linker 2]b-[the VH of the third antigen-binding domain]-CH1-Fc, and the second polypeptide chain is represented by the following structure: [the VL of the third antigen-binding domain]-Cκ-[linker 5]e-[the first antigen-binding domain];

wherein-represents a peptide bond;

the linker 1, linker 2, linker 3, linker 4, and linker 5 may be identical or different; a, b, c, d, and e are optionally independently 0 or 1.

12. The PD-1/PVRIG/TIGIT-binding protein according to claim 5, comprising a first polypeptide chain and a second polypeptide chain, wherein the first polypeptide chain and the second polypeptide chain are selected from any of the following groups:

the first and second polypeptide chains comprising the amino acid sequences set forth in SEQ ID NOs: 97 and 68, respectively;

the first and second polypeptide chains comprising the amino acid sequences set forth in SEQ ID NOs: 98 and 68, respectively;

the first and second polypeptide chains comprising the amino acid sequences set forth in SEQ ID NOs: 87 and 68, respectively;

the first and second polypeptide chains comprising the amino acid sequences set forth in SEQ ID NOs: 84 and 88, respectively;

the first and second polypeptide chains comprising the amino acid sequences set forth in SEQ ID NOs: 89 and 68, respectively;

the first and second polypeptide chains comprising the amino acid sequences set forth in SEQ ID NOs: 84 and 90, respectively;

the first and second polypeptide chains comprising the amino acid sequences set forth in SEQ ID NOs: 91 and 68, respectively;

the first and second polypeptide chains comprising the amino acid sequences set forth in SEQ ID NOs: 85 and 92, respectively;

the first and second polypeptide chains comprising the amino acid sequences set forth in SEQ ID NOs: 93 and 68, respectively;

the first and second polypeptide chains comprising the amino acid sequences set forth in SEQ ID NOs: 85 and 94, respectively;

and a combination of amino acid sequences having at least 90% sequence identity to the first and second polypeptide chains, respectively.

13. A PD-1/PVRIG-binding protein, comprising:

the PD-1-binding protein according to claim 1, and an antigen-binding domain that specifically binds to PVRIG.

14. A PD-1/TIGIT-binding protein, comprising:

the PD-1-binding protein according to claim 1, and an antigen-binding domain that specifically binds to TIGIT.

15. A polynucleotide, encoding the PD-1/PVRIG/TIGIT-binding protein according to claim 5.

16. A host cell, comprising the polynucleotide according to claim 15.

17. A method for preparing a PD-1/PVRIG/TIGIT-binding protein, comprising:

1) culturing the host cell according to claim 16, and 2) isolating the expressed PD-1/PVRIG/TIGIT-binding protein.

18. A pharmaceutical composition, comprising:

at least one pharmaceutically acceptable excipient, diluent, or carrier; and the PD-1/PVRIG/TIGIT-binding protein according to claim 5.

19. A method for treating cancer, comprising the step of:

administering to a subject a therapeutically effective amount of the PD-1/PVRIG/TIGIT-binding protein according to claim 5.

20. A method for activating NK cells, γδT cells, and/or Th1 cells, comprising the step of:

administering to a subject in need thereof an effective amount of the PD-1/PVRIG/TIGIT-binding protein according to claim 5.

21. A method for increasing IFN-γ production and/or proinflammatory cytokine secretion in a subject, comprising the step of: administering to the subject in need thereof an effective amount of the PD-1/PVRIG/TIGIT-binding protein according to claim 5.

22. A method for inhibiting PD-1 activity and/or promoting T cell proliferation in a subject, comprising the step of:

administering to the subject in need thereof an effective amount of the PD-1/PVRIG/TIGIT-binding protein according to claim 5.

23. The PD-1-binding protein according to claim 1, wherein the amino acid sequences of the CDR1, CDR2, and CDR3 of the immunoglobulin single variable domain comprise the amino acid sequences of:

SEQ ID NOs: 7, 38, and 41, respectively;
SEQ ID NOs: 7, 8, and 9, respectively;
SEQ ID NOs: 7, 8, and 42, respectively;
SEQ ID NOs: 7, 38, and 9, respectively;
SEQ ID NOs: 7, 39, and 9, respectively;
SEQ ID NOs: 7, 40, and 9, respectively;
SEQ ID NOs: 7, 8, and 41, respectively;
SEQ ID NOs: 7, 8, and 42, respectively;
SEQ ID NOs: 7, 38, and 41, respectively;
SEQ ID NOs: 7, 38, and 42, respectively;
SEQ ID NOs: 7, 39, and 41, respectively;
SEQ ID NOs: 7, 39, and 42, respectively;
SEQ ID NOs: 7, 40, and 41, respectively;
SEQ ID NOs: 7, 40, and 42, respectively;
SEQ ID NOs: 7, 101, and 41, or SEQ ID NOs: 4, 5, and 6, respectively.

24. The PD-1/PVRIG/TIGIT-binding protein according to claim 5, wherein the PD-1/PVRIG/TIGIT-binding protein is an anti-PD-1/PVRIG/TIGIT trispecific antibody.

* * * * *

SEQUENCE LISTING

```
Sequence total quantity: 101
SEQ ID NO: 1           moltype = AA  length = 288
FEATURE                Location/Qualifiers
source                 1..288
                       mol_type = protein
                       organism = synthetic construct
SEQUENCE: 1
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL                288

SEQ ID NO: 2           moltype = AA  length = 122
FEATURE                Location/Qualifiers
source                 1..122
                       mol_type = protein
                       organism = synthetic construct
SEQUENCE: 2
EVQLVESGGG LVQAGGSLRL SCAVSGRTFS SAAMGWFRQA PGKEREFVAA ISWSFGSTYY  60
ADSVKGRFTI SRDNAKNTVY LQMNSLKPED TAVYYCAADP SIETMGGGWD YWGQGTQVTV  120
SS                                                                  122

SEQ ID NO: 3           moltype = AA  length = 116
FEATURE                Location/Qualifiers
source                 1..116
                       mol_type = protein
                       organism = synthetic construct
SEQUENCE: 3
EVQVVESGGG LVQPGGSLRL SCVASGLTFS DYSMSWYRQA PGKERELVAI ISGSGVIAHY  60
VDSVKGRFTI SRDNAKSTVY LQMVSLKPED RGVYYCRAVS DWDDYWGQGT QVTVSS      116

SEQ ID NO: 4           moltype = AA  length = 5
FEATURE                Location/Qualifiers
source                 1..5
                       mol_type = protein
                       organism = synthetic construct
SEQUENCE: 4
SAAMG                                                               5

SEQ ID NO: 5           moltype = AA  length = 16
FEATURE                Location/Qualifiers
source                 1..16
                       mol_type = protein
                       organism = synthetic construct
SEQUENCE: 5
ISWSFGSTYY ADSVKG                                                   16
```

```
SEQ ID NO: 6            moltype = AA  length = 13
FEATURE                 Location/Qualifiers
source                  1..13
                        mol_type = protein
                        organism = synthetic construct
SEQUENCE: 6
DPSIETMGGG WDY                                                     13

SEQ ID NO: 7            moltype = AA  length = 5
FEATURE                 Location/Qualifiers
source                  1..5
                        mol_type = protein
                        organism = synthetic construct
SEQUENCE: 7
DYSMS                                                              5

SEQ ID NO: 8            moltype = AA  length = 17
FEATURE                 Location/Qualifiers
source                  1..17
                        mol_type = protein
                        organism = synthetic construct
SEQUENCE: 8
IISGSGVIAH YVDSVKG                                                 17

SEQ ID NO: 9            moltype = AA  length = 7
FEATURE                 Location/Qualifiers
source                  1..7
                        mol_type = protein
                        organism = synthetic construct
SEQUENCE: 9
VSDWDDY                                                            7

SEQ ID NO: 10           moltype = AA  length = 229
FEATURE                 Location/Qualifiers
source                  1..229
                        mol_type = protein
                        organism = synthetic construct
SEQUENCE: 10
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK          229

SEQ ID NO: 11           moltype = AA  length = 351
FEATURE                 Location/Qualifiers
source                  1..351
                        mol_type = protein
                        organism = synthetic construct
SEQUENCE: 11
EVQLVESGGG LVQAGGSLRL SCAVSGRTFS SAAMGWFRQA PGKEREFVAA ISWSFGSTYY  60
ADSVKGRFTI SRDNAKNTVY LQMNSLKPED TAVYYCAADP SIETMGGGWD YWGQGTQVTV  120
SSESKYGPPC PPCPAPEFLG GPSVFLFPPK PKDTLMISRT PEVTCVVVDV SQEDPEVQFN  180
WYVDGVEVHN AKTKPREEQF NSTYRVVSVL TVLHQDWLNG KEYKCKVSNK GLPSSIEKTI  240
SKAKGQPREP QVYTLPPSQE EMTKNQVSLT CLVKGFYPSD IAVEWESNGQ PENNYKTTPP  300
VLDSDGSFFL YSRLTVDKSR WQEGNVFSCS VMHEALHNHY TQKSLSLSLG K          351

SEQ ID NO: 12           moltype = AA  length = 345
FEATURE                 Location/Qualifiers
source                  1..345
                        mol_type = protein
                        organism = synthetic construct
SEQUENCE: 12
EVQVVESGGG LVQPGGSLRL SCVASGLTFS DYSMSWYRQA PGKERELVAI ISGSGVIAHY  60
VDSVKGRFTI SRDNAKSTVY LQMVSLKPED RGVYYCRAVS DWDDYWGQGT QVTVSSESKY  120
GPPCPPCPAP EFLGGPSVFL FPPKPKDTLM ISRTPEVTCV VVDVSQEDPE VQFNWYVDGV  180
EVHNAKTKPR EEQFNSTYRV VSVLTVLHQD WLNGKEYKCK VSNKGLPSSI EKTISKAKGQ  240
PREPQVYTLP PSQEEMTKNQ VSLTCLVKGF YPSDIAVEWE SNGQPENNYK TTPPVLDSDG  300
SFFLYSRLTV DKSRWQEGNV FSCSVMHEAL HNHYTQKSLS LSLGK                345

SEQ ID NO: 13           moltype = AA  length = 116
FEATURE                 Location/Qualifiers
source                  1..116
                        mol_type = protein
                        organism = synthetic construct
SEQUENCE: 13
EVQLQESGGG LVQPGGSLRL SCTASGLTFS DYSMSWYRQA PGKGRELVAI ISGSGVIAHY  60
VDSVKGRFTI SRDNSKNTVY LQMRSLTPED RAVYYCRAVS DWDDYWGQGT QVTVSS      116
```

```
SEQ ID NO: 14          moltype = AA  length = 116
FEATURE                Location/Qualifiers
source                 1..116
                       mol_type = protein
                       organism = synthetic construct
SEQUENCE: 14
EVQLVESGGG LVQPGGSLRL SCAASGLTFS DYSMSWVRQA PGKGLEWVAI ISGSGVIAHY  60
VDSVKGRFTI SRDNSKNTVY LQMNSLRAED TAVYYCRAVS DWDDYWGQGT QVTVSS      116

SEQ ID NO: 15          moltype = AA  length = 116
FEATURE                Location/Qualifiers
source                 1..116
                       mol_type = protein
                       organism = synthetic construct
SEQUENCE: 15
EVQLVESGGG LVQPGGSLRL SCAASGLTFS DYSMSWVRQA PGKGLEWVAI ISGSGVIAHY  60
VDSVKGRFTI SRDNSKNTVY LQMNSLRAED TAVYYCRAVS DWDEYWGQGT QVTVSS      116

SEQ ID NO: 16          moltype = AA  length = 122
FEATURE                Location/Qualifiers
source                 1..122
                       mol_type = protein
                       organism = synthetic construct
SEQUENCE: 16
EVQLLESGGG LVQAGGSLRL SCATSGRTFS SAAMGWFRQA PGKGLEWVAA ISWSFGSTYY  60
ADSVKGRFTI SRDNSKNTVY LQMNSLRPED TAVYYCAADP SIETMGGGWD YWGQGTQVTV  120
SS                                                                 122

SEQ ID NO: 17          moltype = AA  length = 116
FEATURE                Location/Qualifiers
source                 1..116
                       mol_type = protein
                       organism = synthetic construct
SEQUENCE: 17
EVQLQESGGG LVQPGGSLRL SCTASGLTFS DYSMSWYRQA PGKGRELVAI ISGSGVIAHY  60
VDSVKGRFTI SRDNAKNTVY LQMRSLTPED RAVYYCRAVS DWDDYWGQGT QVTVSS      116

SEQ ID NO: 18          moltype = AA  length = 116
FEATURE                Location/Qualifiers
source                 1..116
                       mol_type = protein
                       organism = synthetic construct
SEQUENCE: 18
EVQLQESGGG LVQPGGSLRL SCTASGLTFS DYSMSWYRQA PGKGRELVAI ISGSGVITHY  60
VDSVKGRFTI SRDNSKNTVY LQMRSLTPED RAVYYCRAVS DWDDYWGQGT QVTVSS      116

SEQ ID NO: 19          moltype = AA  length = 116
FEATURE                Location/Qualifiers
source                 1..116
                       mol_type = protein
                       organism = synthetic construct
SEQUENCE: 19
EVQLQESGGG LVQPGGSLRL SCTASGLTFS DYSMSWYRQA PGKGRELVAI ISGSGGIAHY  60
VDSVKGRFTI SRDNSKNTVY LQMRSLTPED RAVYYCRAVS DWDDYWGQGT QVTVSS      116

SEQ ID NO: 20          moltype = AA  length = 116
FEATURE                Location/Qualifiers
source                 1..116
                       mol_type = protein
                       organism = synthetic construct
SEQUENCE: 20
EVQLQESGGG LVQPGGSLRL SCTASGLTFS DYSMSWYRQA PGKGRELVAI ISGSGVSAHY  60
VDSVKGRFTI SRDNSKNTVY LQMRSLTPED RAVYYCRAVS DWDDYWGQGT QVTVSS      116

SEQ ID NO: 21          moltype = AA  length = 116
FEATURE                Location/Qualifiers
source                 1..116
                       mol_type = protein
                       organism = synthetic construct
SEQUENCE: 21
EVQLQESGGG LVQPGGSLRL SCTASGLTFS DYSMSWYRQA PGKGRELVAI ISGSGVIAHY  60
VDSVKGRFTI SRDNSKNTVY LQMRSLTPED RAVYYCRAVS DWEDYWGQGT QVTVSS      116

SEQ ID NO: 22          moltype = AA  length = 116
FEATURE                Location/Qualifiers
source                 1..116
                       mol_type = protein
                       organism = synthetic construct
```

```
SEQUENCE: 22
EVQLQESGGG LVQPGGSLRL SCTASGLTFS DYSMSWYRQA PGKGRELVAI ISGSGVIAHY  60
VDSVKGRFTI SRDNSKNTVY LQMRSLTPED RAVYYCRAVS DWDEYWGQGT QVTVSS      116

SEQ ID NO: 23          moltype = AA  length = 116
FEATURE                Location/Qualifiers
source                 1..116
                       mol_type = protein
                       organism = synthetic construct
SEQUENCE: 23
EVQLQESGGG LVQPGGSLRL SCTASGLTFS DYSMSWYRQA PGKGRELVAI ISGSGVIAHY  60
VDSVKGRFTI SRDNAKNTVY LQMRSLTPED RAVYYCRAVS DWEDYWGQGT QVTVSS      116

SEQ ID NO: 24          moltype = AA  length = 116
FEATURE                Location/Qualifiers
source                 1..116
                       mol_type = protein
                       organism = synthetic construct
SEQUENCE: 24
EVQLQESGGG LVQPGGSLRL SCTASGLTFS DYSMSWYRQA PGKGRELVAI ISGSGVIAHY  60
VDSVKGRFTI SRDNAKNTVY LQMRSLTPED RAVYYCRAVS DWDEYWGQGT QVTVSS      116

SEQ ID NO: 25          moltype = AA  length = 116
FEATURE                Location/Qualifiers
source                 1..116
                       mol_type = protein
                       organism = synthetic construct
SEQUENCE: 25
EVQLQESGGG LVQPGGSLRL SCTASGLTFS DYSMSWYRQA PGKGRELVAI ISGSGVITHY  60
VDSVKGRFTI SRDNAKNTVY LQMRSLTPED RAVYYCRAVS DWEDYWGQGT QVTVSS      116

SEQ ID NO: 26          moltype = AA  length = 116
FEATURE                Location/Qualifiers
source                 1..116
                       mol_type = protein
                       organism = synthetic construct
SEQUENCE: 26
EVQLQESGGG LVQPGGSLRL SCTASGLTFS DYSMSWYRQA PGKGRELVAI ISGSGVITHY  60
VDSVKGRFTI SRDNAKNTVY LQMRSLTPED RAVYYCRAVS DWDEYWGQGT QVTVSS      116

SEQ ID NO: 27          moltype = AA  length = 116
FEATURE                Location/Qualifiers
source                 1..116
                       mol_type = protein
                       organism = synthetic construct
SEQUENCE: 27
EVQLQESGGG LVQPGGSLRL SCTASGLTFS DYSMSWYRQA PGKGRELVAI ISGSGGIAHY  60
VDSVKGRFTI SRDNAKNTVY LQMRSLTPED RAVYYCRAVS DWEDYWGQGT QVTVSS      116

SEQ ID NO: 28          moltype = AA  length = 116
FEATURE                Location/Qualifiers
source                 1..116
                       mol_type = protein
                       organism = synthetic construct
SEQUENCE: 28
EVQLQESGGG LVQPGGSLRL SCTASGLTFS DYSMSWYRQA PGKGRELVAI ISGSGGIAHY  60
VDSVKGRFTI SRDNAKNTVY LQMRSLTPED RAVYYCRAVS DWDEYWGQGT QVTVSS      116

SEQ ID NO: 29          moltype = AA  length = 116
FEATURE                Location/Qualifiers
source                 1..116
                       mol_type = protein
                       organism = synthetic construct
SEQUENCE: 29
EVQLQESGGG LVQPGGSLRL SCTASGLTFS DYSMSWYRQA PGKGRELVAI ISGSGVSAHY  60
VDSVKGRFTI SRDNAKNTVY LQMRSLTPED RAVYYCRAVS DWEDYWGQGT QVTVSS      116

SEQ ID NO: 30          moltype = AA  length = 116
FEATURE                Location/Qualifiers
source                 1..116
                       mol_type = protein
                       organism = synthetic construct
SEQUENCE: 30
EVQLQESGGG LVQPGGSLRL SCTASGLTFS DYSMSWYRQA PGKGRELVAI ISGSGVSAHY  60
VDSVKGRFTI SRDNAKNTVY LQMRSLTPED RAVYYCRAVS DWDEYWGQGT QVTVSS      116

SEQ ID NO: 31          moltype = AA  length = 116
FEATURE                Location/Qualifiers
```

```
source                  1..116
                        mol_type = protein
                        organism = synthetic construct
SEQUENCE: 31
EVQLQESGGG LVQPGGSLRL SCTASGLTFS DYSMSWYRQA PGKGRELVAI ISGSGGITHY  60
VDSVKGRFTI SRDNAKNTVY LQMRSLTPED RAVYYCRAVS DWEDYWGQGT QVTVSS      116

SEQ ID NO: 32           moltype = AA  length = 116
FEATURE                 Location/Qualifiers
source                  1..116
                        mol_type = protein
                        organism = synthetic construct
SEQUENCE: 32
EVQLVESGGG LVQPGGSLRL SCAASGFTFS DYSMSWYRQA PGKGRELVAI ISGSGVITHY  60
VDSVKGRFTI SRDNAKNTLY LQMRSLRAED TAVYYCRAVS DWEDYWGQGT QVTVSS      116

SEQ ID NO: 33           moltype = AA  length = 116
FEATURE                 Location/Qualifiers
source                  1..116
                        mol_type = protein
                        organism = synthetic construct
SEQUENCE: 33
EVQLVESGGG LVQPGGSLRL SCAASGLTFS DYSMSWYRQA PGKGRELVAI ISGSGVITHY  60
VDSVKGRFTI SRDNAKNTLY LQMRSLRAED TAVYYCRAVS DWEDYWGQGT QVTVSS      116

SEQ ID NO: 34           moltype = AA  length = 116
FEATURE                 Location/Qualifiers
source                  1..116
                        mol_type = protein
                        organism = synthetic construct
SEQUENCE: 34
EVQLVESGGG LVQPGGSLRL SCAASGLTFS DYSMSWYRQA PGKGRELVAI ISGSGVITHY  60
VDSVKGRFTI SRDNAKNTVY LQMRSLRAED TAVYYCRAVS DWEDYWGQGT QVTVSS      116

SEQ ID NO: 35           moltype = AA  length = 116
FEATURE                 Location/Qualifiers
source                  1..116
                        mol_type = protein
                        organism = synthetic construct
SEQUENCE: 35
EVQLVESGGG LVQPGGSLRL SCAASGLTFS DYSMSWYRQA PGKGRELVAI ISGSGVITHY  60
VDSVKGRFTI SRDNAKNTVY LQMRSLRAED RAVYYCRAVS DWEDYWGQGT QVTVSS      116

SEQ ID NO: 36           moltype = AA  length = 17
FEATURE                 Location/Qualifiers
source                  1..17
                        mol_type = protein
                        organism = synthetic construct
VARIANT                 7
                        note = X is V or G
VARIANT                 9
                        note = X is T or A
VARIANT                 8
                        note = X is I or S
SEQUENCE: 36
IISGSGXXXH YVDSVKG                                                 17

SEQ ID NO: 37           moltype = AA  length = 7
FEATURE                 Location/Qualifiers
source                  1..7
                        mol_type = protein
                        organism = synthetic construct
VARIANT                 5
                        note = X is D or E
VARIANT                 6
                        note = X is D or E
SEQUENCE: 37
VSDWXXY                                                            7

SEQ ID NO: 38           moltype = AA  length = 17
FEATURE                 Location/Qualifiers
source                  1..17
                        mol_type = protein
                        organism = synthetic construct
SEQUENCE: 38
IISGSGVITH YVDSVKG                                                 17

SEQ ID NO: 39           moltype = AA  length = 17
FEATURE                 Location/Qualifiers
```

```
source                  1..17
                        mol_type = protein
                        organism = synthetic construct
SEQUENCE: 39
IISGSGGIAH YVDSVKG                                              17

SEQ ID NO: 40           moltype = AA  length = 17
FEATURE                 Location/Qualifiers
source                  1..17
                        mol_type = protein
                        organism = synthetic construct
SEQUENCE: 40
IISGSGVSAH YVDSVKG                                              17

SEQ ID NO: 41           moltype = AA  length = 7
FEATURE                 Location/Qualifiers
source                  1..7
                        mol_type = protein
                        organism = synthetic construct
SEQUENCE: 41
VSDWEDY                                                         7

SEQ ID NO: 42           moltype = AA  length = 7
FEATURE                 Location/Qualifiers
source                  1..7
                        mol_type = protein
                        organism = synthetic construct
SEQUENCE: 42
VSDWDEY                                                         7

SEQ ID NO: 43           moltype = AA  length = 137
FEATURE                 Location/Qualifiers
source                  1..137
                        mol_type = protein
                        organism = synthetic construct
SEQUENCE: 43
TPEVWVQVQM EATELSSFTV HCGFLGPGSI SLVTVSWGGP DGAGGTKLAV LHPELGTRQW  60
APARQARWET QSSISLALED SGASSPFANT TFCCKFASFP EGSWESCGSL PPSSDPGLSA  120
PPTPVPILRA DHHHHHH                                              137

SEQ ID NO: 44           moltype = AA  length = 121
FEATURE                 Location/Qualifiers
source                  1..121
                        mol_type = protein
                        organism = synthetic construct
SEQUENCE: 44
HVQLVESGGG SVQAGGSLRL SCEASGYSYS GDCMGWFRRA PGKERDEGVA TIDNAGRIKY  60
ADSVKGRFTI SHGNGKYILY LQMNSLKPED TDMYYCAAGW TFGGNCSPAD WGQGTQVTVS  120
S                                                               121

SEQ ID NO: 45           moltype = AA  length = 127
FEATURE                 Location/Qualifiers
source                  1..127
                        mol_type = protein
                        organism = synthetic construct
SEQUENCE: 45
HVQLVESGGG SVQAGGSLRL SCVASASGFT YRPYCMAWFR QAPGKEREAV AGIDIFGGTT  60
YADSVKGRFT ASRDNAGFSL FLQMNDLKPE DTAMYYCAAG DSPDGRCPPL GQGLNYWGQG  120
TQVTVSS                                                         127

SEQ ID NO: 46           moltype = AA  length = 5
FEATURE                 Location/Qualifiers
source                  1..5
                        mol_type = protein
                        organism = synthetic construct
SEQUENCE: 46
GDCMG                                                           5

SEQ ID NO: 47           moltype = AA  length = 16
FEATURE                 Location/Qualifiers
source                  1..16
                        mol_type = protein
                        organism = synthetic construct
SEQUENCE: 47
TIDNAGRIKY ADSVKG                                               16

SEQ ID NO: 48           moltype = AA  length = 12
FEATURE                 Location/Qualifiers
```

```
source                  1..12
                        mol_type = protein
                        organism = synthetic construct
SEQUENCE: 48
GWTFGGNCSP AD                                                12

SEQ ID NO: 49           moltype = AA  length = 7
FEATURE                 Location/Qualifiers
source                  1..7
                        mol_type = protein
                        organism = synthetic construct
SEQUENCE: 49
YRPYCMA                                                      7

SEQ ID NO: 50           moltype = AA  length = 16
FEATURE                 Location/Qualifiers
source                  1..16
                        mol_type = protein
                        organism = synthetic construct
SEQUENCE: 50
GIDIFGGTTY ADSVKG                                            16

SEQ ID NO: 51           moltype = AA  length = 17
FEATURE                 Location/Qualifiers
source                  1..17
                        mol_type = protein
                        organism = synthetic construct
SEQUENCE: 51
GDSPDGRCPP LGQGLNY                                           17

SEQ ID NO: 52           moltype = AA  length = 229
FEATURE                 Location/Qualifiers
source                  1..229
                        mol_type = protein
                        organism = synthetic construct
SEQUENCE: 52
ESKYGPPCPP CPAPEAAGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGA          229

SEQ ID NO: 53           moltype = AA  length = 350
FEATURE                 Location/Qualifiers
source                  1..350
                        mol_type = protein
                        organism = synthetic construct
SEQUENCE: 53
HVQLVESGGG SVQAGGSLRL SCEASGYSYS GDCMGWFRRA PGKERDEGVA TIDNAGRIKY  60
ADSVKGRFTI SHGNGKYILY LQMNSLKPED TDMYYCAAGW TFGGNCSPAD WGQGTQVTVS  120
SESKYGPPCP PCPAPEAAGG PSVFLFPPKP KDTLMISRTP EVTCVVVDVS QEDPEVQFNW  180
YVDGVEVHNA KTKPREEQFN STYRVVSVLT VLHQDWLNGK EYKCKVSNKG LPSSIEKTIS  240
KAKGQPREPQ VYTLPPSQEE MTKNQVSLTC LVKGFYPSDI AVEWESNGQP ENNYKTTPPV  300
LDSDGSFFLY SRLTVDKSRW QEGNVFSCSV MHEALHNHYT QKSLSLSLGA            350

SEQ ID NO: 54           moltype = AA  length = 356
FEATURE                 Location/Qualifiers
source                  1..356
                        mol_type = protein
                        organism = synthetic construct
SEQUENCE: 54
HVQLVESGGG SVQAGGSLRL SCVASASGFT YRPYCMAWFR QAPGKEREAV AGIDIFGGTT  60
YADSVKGRFT ASRDNAGFSL FLQMNDLKPE DTAMYYCAAG DSPDGRCPPL GQGLNYWGQG  120
TQVTVSSESK YGPPCPPCPA PEAAGGPSVF LFPPKPKDTL MISRTPEVTC VVVDVSQEDP  180
EVQFNWYVDG VEVHNAKTKP REEQFNSTYR VVSVLTVLHQ DWLNGKEYKC KVSNKGLPSS  240
IEKTISKAKG QPREPQVYTL PPSQEEMTKN QVSLTCLVKG FYPSDIAVEW ESNGQPENNY  300
KTTPPVLDSD GSFFLYSRLT VDKSRWQEGN VFSCSVMHEA LHNHYTQKSL SLSLGA      356

SEQ ID NO: 55           moltype = AA  length = 449
FEATURE                 Location/Qualifiers
source                  1..449
                        mol_type = protein
                        organism = synthetic construct
SEQUENCE: 55
EVQLVESGGG VVKPGGSLRL SCAASGFTFG TSSMNWVRQA PGKGLEWVAV ISFDGTEIHY  60
ADSVKGRFTI SRDNSKSTVF LQMNSLRPDD TALYYCAKGS GNIYFYSGMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEAAGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
```

```
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGA                                   449

SEQ ID NO: 56           moltype = AA  length = 214
FEATURE                 Location/Qualifiers
source                  1..214
                        mol_type = protein
                        organism = synthetic construct
SEQUENCE: 56
DIQMTQSPST LSASVGDRVT ITCRAGQSIS GWLAWFQQKP GKAPNLLIYE TSTLESGVPS  60
RFSGSGSGTE YTLTISSLQP DDFATYYCQQ YYSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 57           moltype = AA  length = 120
FEATURE                 Location/Qualifiers
source                  1..120
                        mol_type = protein
                        organism = synthetic construct
SEQUENCE: 57
EVQLVESGGG LVQPGGSLRL SCAASGFTFS GDCMGWFRQA PGKGLEGVAT IDNAGRIKYA  60
DSVKGRFTIS RDNAKNSLYL QMNSLRAEDT AVYYCAAGWT FGGQCSPADW GQGTQVTVSS  120

SEQ ID NO: 58           moltype = AA  length = 121
FEATURE                 Location/Qualifiers
source                  1..121
                        mol_type = protein
                        organism = synthetic construct
SEQUENCE: 58
EVQLVESGGG LVQPGGSLRL SCAASGFTFS GDCMGWFRQA PGKGLDEGVA TIDNAGRIKY  60
ADSVKGRFTI SRDNAKNSLY LQMNSLRAED TAVYYCAAGW TFGGQCSPAD WGQGTQVTVS  120
S                                                                 121

SEQ ID NO: 59           moltype = AA  length = 121
FEATURE                 Location/Qualifiers
source                  1..121
                        mol_type = protein
                        organism = synthetic construct
SEQUENCE: 59
EVQLVESGGG LVQPGGSLRL SCAASGYSYS GDCMGWFRQA PGKGLDEGVA TIDNAGRIKY  60
ADSVKGRFTI SRDNAKNSLY LQMNSLRAED TAVYYCAAGW TFGGQCSPAD WGQGTQVTVS  120
S                                                                 121

SEQ ID NO: 60           moltype = AA  length = 121
FEATURE                 Location/Qualifiers
source                  1..121
                        mol_type = protein
                        organism = synthetic construct
SEQUENCE: 60
EVQLVESGGG LVQPGGSLRL SCAASGFTFS GDCMGWFRQA PGKGLDEGVA TIDNAGRIKY  60
ADSVKGRFTI SHGNAKYILY LQMNSLRAED TAVYYCAAGW TFGGQCSPAD WGQGTQVTVS  120
S                                                                 121

SEQ ID NO: 61           moltype = AA  length = 121
FEATURE                 Location/Qualifiers
source                  1..121
                        mol_type = protein
                        organism = synthetic construct
SEQUENCE: 61
EVQLVESGGG LVQPGGSLRL SCAASGYSYS GDCMGWFRQA PGKGLDEGVA TIDNAGRIKY  60
ADSVKGRFTI SHGNAKYILY LQMNSLRAED TAVYYCAAGW TFGGQCSPAD WGQGTQVTVS  120
S                                                                 121

SEQ ID NO: 62           moltype = AA  length = 125
FEATURE                 Location/Qualifiers
source                  1..125
                        mol_type = protein
                        organism = synthetic construct
SEQUENCE: 62
EVQLVESGGG LVQPGGSLRL SCAASGFTYR PYCMAWFRQA PGKGLEAVAG IDIFGGTTYA  60
DSVKGRFTIS RDNAKNSLYL QMNSLRAEDT AVYYCAAGDS PDGRCPPLGQ GLNYWGQGTM  120
VTVSS                                                             125

SEQ ID NO: 63           moltype = AA  length = 127
FEATURE                 Location/Qualifiers
source                  1..127
                        mol_type = protein
                        organism = synthetic construct
```

```
SEQUENCE: 63
EVQLVESGGG LVQPGGSLRL SCVASASGFT YRPYCMAWFR QAPGKGLEAV AGIDIFGGTT  60
YADSVKGRFT ISRDNAKNSL YLQMNSLRAE DTAVYYCAAG DSPDGRCPPL GQGLNYWGQG  120
TMVTVSS                                                            127

SEQ ID NO: 64          moltype = AA  length = 127
FEATURE                Location/Qualifiers
source                 1..127
                       mol_type = protein
                       organism = synthetic construct
SEQUENCE: 64
HVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSS                                                            127

SEQ ID NO: 65          moltype = AA  length = 127
FEATURE                Location/Qualifiers
source                 1..127
                       mol_type = protein
                       organism = synthetic construct
SEQUENCE: 65
EVQLVESGGG LVQPGGSLRL SCVASASGFT YRPYCMAWFR QAPGKGLEAV AGIDIFGGTT  60
YADSVKGRFT ISRDNAGFSL YLQMNSLRAE DTAVYYCAAG DSPDGRCPPL GQGLNYWGQG  120
TMVTVSS                                                            127

SEQ ID NO: 66          moltype = AA  length = 127
FEATURE                Location/Qualifiers
source                 1..127
                       mol_type = protein
                       organism = synthetic construct
SEQUENCE: 66
HVQLVESGGG LVQPGGSLRL SCVASASGFT YRPYCMAWFR QAPGKGLEAV AGIDIFGGTT  60
YADSVKGRFT ASRDNAGFSL YLQMNSLRAE DTAVYYCAAG DSPDGRCPPL GQGLNYWGQG  120
TMVTVSS                                                            127

SEQ ID NO: 67          moltype = AA  length = 446
FEATURE                Location/Qualifiers
source                 1..446
                       mol_type = protein
                       organism = synthetic construct
SEQUENCE: 67
EVQLVQSGAE VKKPGASVKV SCKASGYTFT NYWMHWVRQA PGQGLEWMGR IDPDSTGSKY  60
NEKFKTRVTM TRDTSTSTVY MELSSLRSED TAVYYCAREG AYGYYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 68          moltype = AA  length = 214
FEATURE                Location/Qualifiers
source                 1..214
                       mol_type = protein
                       organism = synthetic construct
SEQUENCE: 68
DIQMTQSPSS LSASVGDRVT ITCRASENIY SYLAWYQQKP GKSPKLLIYN ARTLAEGVPS  60
RFSGSGSGTD FTLTISSLQP EDFATYYCQY HSGSPLPFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 69          moltype = AA  length = 583
FEATURE                Location/Qualifiers
source                 1..583
                       mol_type = protein
                       organism = synthetic construct
SEQUENCE: 69
HVQLVESGGG SVQAGGSLRL SCVASASGFT YRPYCMAWFR QAPGKEREAV AGIDIFGGTT  60
YADSVKGRFT ASRDNAGFSL FLQMNDLKPE DTAMYYCAAG DSPDGRCPPL GQGLNYWGQG  120
TQVTVSSGGG GSGGGGSEVQ LVQSGAEVKK PGASVKVSCK ASGYTFTNYW MHWVRQAPGQ  180
GLEWMGRIDP DSTGSKYNEK FKTRVTMTRD TSTSTVYMEL SSLRSEDTAV YYCAREGAYG  240
YYFDYWGQGT LVTVSSASTK GPSVFPLAPC SRSTSESTAA LGCLVKDYFP EPVTVSWNSG  300
ALTSGVHTFP AVLQSSGLYS LSSVVTVPSS SLGTKTYTCN VDHKPSNTKV DKRVESKYGP  360
PCPPCPAPEF LGGPSVFLFP PKPKDTLMIS RTPEVTCVVV DVSQEDPEVQ FNWYVDGVEV  420
HNAKTKPREE QFNSTYRVVS VLTVLHQDWL NGKEYKCKVS NKGLPSSIEK TISKAKGQPR  480
EPQVYTLPPS QEEMTKNQVS LTCLVKGFYP SDIAVEWESN GQPENNYKTT PPVLDSDGSF  540
FLYSRLTVDK SRWQEGNVFS CSVMHEALHN HYTQKSLSLS LGK                    583

SEQ ID NO: 70          moltype = AA  length = 583
```

```
FEATURE                 Location/Qualifiers
source                  1..583
                        mol_type = protein
                        organism = synthetic construct
SEQUENCE: 70
EVQLVQSGAE VKKPGASVKV SCKASGYTFT NYWMHWVRQA PGQGLEWMGR IDPDSTGSKY  60
NEKFKTRVTM TRDTSTSTVY MELSSLRSED TAVYYCAREG AYGYYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGKGGGG SGGGGSHVQL VESGGGSVQA GGSLRLSCVA  480
SASGFTYRPY CMAWFRQAPG KEREAVAGID IFGGTTYADS VKGRFTASRD NAGFSLFLQM  540
NDLKPEDTAM YYCAAGDSPD GRCPPLGQGL NYWGQGTQVT VSS                    583

SEQ ID NO: 71           moltype = AA  length = 351
FEATURE                 Location/Qualifiers
source                  1..351
                        mol_type = protein
                        organism = synthetic construct
SEQUENCE: 71
HVQLVESGGG SVQAGGSLRL SCVASASGFT YRPYCMAWFR QAPGKEREAV AGIDIFGGTT  60
YADSVKGRFT ASRDNAGFSL FLQMNDLKPE DTAMYYCAAG DSPDGRCPPL GQGLNYWGQG  120
TQVTVSSGGG GSGGGGSDIQ MTQSPSSLSA SVGDRVTITC RASENIYSYL AWYQQKPGKS  180
PKLLIYNART LAEGVPSRFS GSGSGTDFTL TISSLQPEDF ATYYCQYHSG SPLPFGGGTK  240
VEIKRTVAAP SVFIFPPSDE QLKSGTASVV CLLNNFYPRE AKVQWKVDNA LQSGNSQESV  300
TEQDSKDSTY SLSSTLTLSK ADYEKHKVYA CEVTHQGLSS PVTKSFNRGE C             351

SEQ ID NO: 72           moltype = AA  length = 351
FEATURE                 Location/Qualifiers
source                  1..351
                        mol_type = protein
                        organism = synthetic construct
SEQUENCE: 72
DIQMTQSPSS LSASVGDRVT ITCRASENIY SYLAWYQQKP GKSPKLLIYN ARTLAEGVPS  60
RFSGSGSGTD FTLTISSLQP EDFATYYCQY HSGSPLPFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSHVQLVE SGGGSVQAGG  240
SLRLSCVASA SGFTYRPYCM AWFRQAPGKE REAVAGIDIF GGTTYADSVK GRFTASRDNA  300
GFSLFLQMND LKPEDTAMYY CAAGDSPDGR CPPLGQGLNY WGQGTQVTVS S             351

SEQ ID NO: 73           moltype = AA  length = 5
FEATURE                 Location/Qualifiers
source                  1..5
                        mol_type = protein
                        organism = synthetic construct
SEQUENCE: 73
NYWMH                                                              5

SEQ ID NO: 74           moltype = AA  length = 17
FEATURE                 Location/Qualifiers
source                  1..17
                        mol_type = protein
                        organism = synthetic construct
SEQUENCE: 74
RIDPDSTGSK YNEKFKT                                                 17

SEQ ID NO: 75           moltype = AA  length = 10
FEATURE                 Location/Qualifiers
source                  1..10
                        mol_type = protein
                        organism = synthetic construct
SEQUENCE: 75
EGAYGYYFDY                                                         10

SEQ ID NO: 76           moltype = AA  length = 11
FEATURE                 Location/Qualifiers
source                  1..11
                        mol_type = protein
                        organism = synthetic construct
SEQUENCE: 76
RASENIYSYL A                                                       11

SEQ ID NO: 77           moltype = AA  length = 7
FEATURE                 Location/Qualifiers
source                  1..7
                        mol_type = protein
                        organism = synthetic construct
```

```
SEQUENCE: 77
NARTLAE                                                 7

SEQ ID NO: 78          moltype = AA  length = 9
FEATURE                Location/Qualifiers
source                 1..9
                       mol_type = protein
                       organism = synthetic construct
SEQUENCE: 78
QYHSGSPLP                                               9

SEQ ID NO: 79          moltype = AA  length = 119
FEATURE                Location/Qualifiers
source                 1..119
                       mol_type = protein
                       organism = synthetic construct
SEQUENCE: 79
EVQLVQSGAE VKKPGASVKV SCKASGYTFT NYWMHWVRQA PGQGLEWMGR IDPDSTGSKY  60
NEKFKTRVTM TRDTSTSTVY MELSSLRSED TAVYYCAREG AYGYYFDYWG QGTLVTVSS   119

SEQ ID NO: 80          moltype = AA  length = 119
FEATURE                Location/Qualifiers
source                 1..119
                       mol_type = protein
                       organism = synthetic construct
SEQUENCE: 80
EVQLVQSGAE VKKPGASVKV SCKASGYTFT NYWMHWVRQA PGQGLEWMGR IDPDSTGSKY  60
NEKFKTRVTM TVDTSTSTVY MELSSLRSED TAVYYCAREG AYGYYFDYWG QGTLVTVSS   119

SEQ ID NO: 81          moltype = AA  length = 119
FEATURE                Location/Qualifiers
source                 1..119
                       mol_type = protein
                       organism = synthetic construct
SEQUENCE: 81
EVQLVQSGAE VKKPGASVKV SCKASGYTFT NYWMHWVRQA PGQGLEWIGR IDPDSTGSKY  60
NEKFKTRVTM TVDTSTSTAY MELSSLRSED TAVYYCAREG AYGYYFDYWG QGTLVTVSS   119

SEQ ID NO: 82          moltype = AA  length = 107
FEATURE                Location/Qualifiers
source                 1..107
                       mol_type = protein
                       organism = synthetic construct
SEQUENCE: 82
DIQMTQSPSS LSASVGDRVT ITCRASENIY SYLAWYQQKP GKAPKLLIYN ARTLAEGVPS  60
RFSGSGSGTD FTLTISSLQP EDFATYYCQY HSGSPLPFGG GTKVEIK                107

SEQ ID NO: 83          moltype = AA  length = 107
FEATURE                Location/Qualifiers
source                 1..107
                       mol_type = protein
                       organism = synthetic construct
SEQUENCE: 83
DIQMTQSPSS LSASVGDRVT ITCRASENIY SYLAWYQQKP GKSPKLLIYN ARTLAEGVPS  60
RFSGSGSGTD FTLTISSLQP EDFATYYCQY HSGSPLPFGG GTKVEIK                107

SEQ ID NO: 84          moltype = AA  length = 577
FEATURE                Location/Qualifiers
source                 1..577
                       mol_type = protein
                       organism = synthetic construct
SEQUENCE: 84
EVQLVESGGG LVQPGGSLRL SCAASGFTFS GDCMGWFRQA PGKGLDEGVA TIDNAGRIKY  60
ADSVKGRFTI SRDNAKNSLY LQMNSLRAED TAVYYCAAGW TFGGQCSPAD WGQGTQVTVS  120
SGGGGSGGGG SEVQLVQSGA EVKKPGASVK VSCKASGYTF TNYWMHWVRQ APGQGLEWMG  180
RIDPDSTGSK YNEKFKTRVT MTRDTSTSTV YMELSSLRSE DTAVYYCARE GAYGYYFDYW  240
GQGTLVTVSS ASTKGPSVFP LAPCSRSTSE STAALGCLVK DYFPEPVTVS WNSGALTSGV  300
HTFPAVLQSS GLYSLSSVVT VPSSSLGTKT YTCNVDHKPS NTKVDKRVES KYGPPCPPCP  360
APEFLGGPSV FLFPPKPKDT LMISRTPEVT CVVVDVSQED PEVQFNWYVD GVEVHNAKTK  420
PREEQFNSTY RVVSVLTVLH QDWLNGKEYK CKVSNKGLPS SIEKTISKAK GQPREPQVYT  480
LPPSQEEMTK NQVSLTCLVK GFYPSDIAVE WESNGQPENN YKTTPPVLDS DGSFFLYSRL  540
TVDKSRWQEG NVFSCSVMHE ALHNHYTQKS LSLSLGK                            577

SEQ ID NO: 85          moltype = AA  length = 583
FEATURE                Location/Qualifiers
source                 1..583
                       mol_type = protein
                       organism = synthetic construct
```

SEQUENCE: 85
HVQLVESGGG LVQPGGSLRL SCVASASGFT YRPYCMAWFR QAPGKEREAV AGIDIFGGTT 60
YADSVKGRFT ASRDNAGFSL YLQMNSLRAE DTAVYYCAAG DSPDGRCPPL GQGLNYWGQG 120
TMVTVSSGGG GSGGGGSEVQ LVQSGAEVKK PGASVKVSCK ASGYTFTNYW MHWVRQAPGQ 180
GLEWMGRIDP DSTGSKYNEK FKTRVTMTRD TSTSTVYMEL SSLRSEDTAV YYCAREGAYG 240
YYFDYWGQGT LVTVSSASTK GPSVFPLAPC SRSTSESTAA LGCLVKDYFP EPVTVSWNSG 300
ALTSGVHTFP AVLQSSGLYS LSSVVTVPSS SLGTKTYTCN VDHKPSNTKV DKRVESKYGP 360
PCPPCPAPEF LGGPSVFLFP PKPKDTLMIS RTPEVTCVVV DVSQEDPEVQ FNWYVDGVEV 420
HNAKTKPREE QFNSTYRVVS VLTVLHQDWL NGKEYKCKVS NKGLPSSIEK TISKAKGQPR 480
EPQVYTLPPS QEEMTKNQVS LTCLVKGFYP SDIAVEWESN GQPENNYKTT PPVLDSDGSF 540
FLYSRLTVDK SRWQEGNVFS CSVMHEALHN HYTQKSLSLS LGK 583

SEQ ID NO: 86 moltype = AA length = 583
FEATURE Location/Qualifiers
source 1..583
mol_type = protein
organism = synthetic construct
SEQUENCE: 86
EVQLVESGGG LVQPGGSLRL SCVASASGFT YRPYCMAWFR QAPGKGLEAV AGIDIFGGTT 60
YADSVKGRFT ISRDNAGFSL YLQMNSLRAE DTAVYYCAAG DSPDGRCPPL GQGLNYWGQG 120
TMVTVSSGGG GSGGGGSEVQ LVQSGAEVKK PGASVKVSCK ASGYTFTNYW MHWVRQAPGQ 180
GLEWMGRIDP DSTGSKYNEK FKTRVTMTRD TSTSTVYMEL SSLRSEDTAV YYCAREGAYG 240
YYFDYWGQGT LVTVSSASTK GPSVFPLAPC SRSTSESTAA LGCLVKDYFP EPVTVSWNSG 300
ALTSGVHTFP AVLQSSGLYS LSSVVTVPSS SLGTKTYTCN VDHKPSNTKV DKRVESKYGP 360
PCPPCPAPEF LGGPSVFLFP PKPKDTLMIS RTPEVTCVVV DVSQEDPEVQ FNWYVDGVEV 420
HNAKTKPREE QFNSTYRVVS VLTVLHQDWL NGKEYKCKVS NKGLPSSIEK TISKAKGQPR 480
EPQVYTLPPS QEEMTKNQVS LTCLVKGFYP SDIAVEWESN GQPENNYKTT PPVLDSDGSF 540
FLYSRLTVDK SRWQEGNVFS CSVMHEALHN HYTQKSLSLS LGK 583

SEQ ID NO: 87 moltype = AA length = 703
FEATURE Location/Qualifiers
source 1..703
mol_type = protein
organism = synthetic construct
SEQUENCE: 87
EVQLVESGGG LVQPGGSLRL SCAASGLTFS DYSMSWYRQA PGKGRELVAI ISGSGVITHY 60
VDSVKGRFTI SRDNAKNTLY LQMRSLRAED TAVYYCRAVS DWEDYWGQGT QVTVSSGGGG 120
SGGGGSEVQL VESGGGLVQP GGSLRLSCAA SGFTFSGDCM GWFRQAPGKG LDEGVATIDN 180
AGRIKYADSV KGRFTISRDN AKNSLYLQMN SLRAEDTAVY YCAAGWTFGG QCSPADWGQG 240
TQVTVSSGGG GSGGGGSEVQ LVQSGAEVKK PGASVKVSCK ASGYTFTNYW MHWVRQAPGQ 300
GLEWMGRIDP DSTGSKYNEK FKTRVTMTRD TSTSTVYMEL SSLRSEDTAV YYCAREGAYG 360
YYFDYWGQGT LVTVSSASTK GPSVFPLAPC SRSTSESTAA LGCLVKDYFP EPVTVSWNSG 420
ALTSGVHTFP AVLQSSGLYS LSSVVTVPSS SLGTKTYTCN VDHKPSNTKV DKRVESKYGP 480
PCPPCPAPEF LGGPSVFLFP PKPKDTLMIS RTPEVTCVVV DVSQEDPEVQ FNWYVDGVEV 540
HNAKTKPREE QFNSTYRVVS VLTVLHQDWL NGKEYKCKVS NKGLPSSIEK TISKAKGQPR 600
EPQVYTLPPS QEEMTKNQVS LTCLVKGFYP SDIAVEWESN GQPENNYKTT PPVLDSDGSF 660
FLYSRLTVDK SRWQEGNVFS CSVMHEALHN HYTQKSLSLS LGK 703

SEQ ID NO: 88 moltype = AA length = 340
FEATURE Location/Qualifiers
source 1..340
mol_type = protein
organism = synthetic construct
SEQUENCE: 88
EVQLVESGGG LVQPGGSLRL SCAASGLTFS DYSMSWYRQA PGKGRELVAI ISGSGVITHY 60
VDSVKGRFTI SRDNAKNTLY LQMRSLRAED TAVYYCRAVS DWEDYWGQGT QVTVSSGGGG 120
SGGGGSDIQM TQSPSSLSAS VGDRVTITCR ASENIYSYLA WYQQKPGKSP KLLIYNARTL 180
AEGVPSRFSG SGSGTDFTLT ISSLQPEDFA TYYCQYHSGS PLPFGGGTKV EIKRTVAAPS 240
VFIFPPSDEQ LKSGTASVVC LLNNFYPREA KVQWKVDNAL QSGNSQESVT EQDSKDSTYS 300
LSSTLTLSKA DYEKHKVYAC EVTHQGLSSP VTKSFNRGEC 340

SEQ ID NO: 89 moltype = AA length = 703
FEATURE Location/Qualifiers
source 1..703
mol_type = protein
organism = synthetic construct
SEQUENCE: 89
EVQLVESGGG LVQPGGSLRL SCAASGFTFS GDCMGWFRQA PGKGLDEGVA TIDNAGRIKY 60
ADSVKGRFTI SRDNAKNSLY LQMNSLRAED TAVYYCAAGW TFGGQCSPAD WGQGTQVTVS 120
SGGGGSGGGG SEVQLVQSGA EVKKPGASVK VSCKASGYTF TNYWMHWVRQ APGQGLEWMG 180
RIDPDSTGSK YNEKFKTRVT MTRDTSTSTV YMELSSLRSE DTAVYYCARE GAYGYYFDYW 240
GQGTLVTVSS ASTKGPSVFP LAPCSRSTSE STAALGCLVK DYFPEPVTVS WNSGALTSGV 300
HTFPAVLQSS GLYSLSSVVT VPSSSLGTKT YTCNVDHKPS NTKVDKRVES KYGPPCPPCP 360
APEFLGGPSV FLFPPKPKDT LMISRTPEVT CVVVDVSQED PEVQFNWYVD GVEVHNAKTK 420
PREEQFNSTY RVVSVLTVLH QDWLNGKEYK CKVSNKGLPS SIEKTISKAK GQPREPQVYT 480
LPPSQEEMTK NQVSLTCLVK GFYPSDIAVE WESNGQPENN YKTTPPVLDS DGSFFLYSRL 540
TVDKSRWQEG NVFSCSVMHE ALHNHYTQKS LSLSLGKGGG GSGGGGSEVQ LVESGGGLVQ 600
PGGSLRLSCA ASGLTFSDYS MSWYRQAPGK GRELVAIISG SGVITHYVDS VKGRFTISRD 660
NAKNTLYLQM RSLRAEDTAV YYCRAVSDWE DYWGQGTQVT VSS 703

```
SEQ ID NO: 90          moltype = AA  length = 340
FEATURE                Location/Qualifiers
source                 1..340
                       mol_type = protein
                       organism = synthetic construct
SEQUENCE: 90
DIQMTQSPSS LSASVGDRVT ITCRASENIY SYLAWYQQKP GKSPKLLIYN ARTLAEGVPS  60
RFSGSGSGTD FTLTISSLQP EDFATYYCQY HSGSPLPFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSEVQLVE SGGGLVQPGG  240
SLRLSCAASG LTFSDYSMSW YRQAPGKGRE LVAIISGSGV ITHYVDSVKG RFTISRDNAK  300
NTLYLQMRSL RAEDTAVYYC RAVSDWEDYW GQGTQVTVSS                        340

SEQ ID NO: 91          moltype = AA  length = 709
FEATURE                Location/Qualifiers
source                 1..709
                       mol_type = protein
                       organism = synthetic construct
SEQUENCE: 91
EVQLVESGGG LVQPGGSLRL SCAASGLTFS DYSMSWYRQA PGKGRELVAI ISGSGVITHY  60
VDSVKGRFTI SRDNAKNTLY LQMRSLRAED TAVYYCRAVS DWEDYWGQGT QVTVSSGGGG  120
SGGGGSHVQL VESGGGLVQP GGSLRLSCVA SASGFTYRPY CMAWFRQAPG KEREAVAGID  180
IFGGTTYADS VKGRFTASRD NAGFSLYLQM NSLRAEDTAV YYCAAGDSPD GRCPPLGQGL  240
NYWGQGTMVT VSSGGGGSGG GGSEVQLVQS GAEVKKPGAS VKVSCKASGY TFTNYWMHWV  300
RQAPGQGLEW MGRIDPDSTG SKYNEKFKTR VTMTRDTSTS TVYMELSSLR SEDTAVYYCA  360
REGAYGYYFD YWGQGTLVTV SSASTKGPSV FPLAPCSRST SESTAALGCL VKDYFPEPVT  420
VSWNSGALTS GVHTFPAVLQ SSGLYSLSSV VTVPSSSLGT KTYTCNVDHK PSNTKVDKRV  480
ESKYGPPCPP CPAPEFLGGP SVFLFPPKPK DTLMISRTPE VTCVVVDVSQ EDPEVQFNWY  540
VDGVEVHNAK TKPREEQFNS TYRVVSVLTV LHQDWLNGKE YKCKVSNKGL PSSIEKTISK  600
AKGQPREPQV YTLPPSQEEM TKNQVSLTCL VKGFYPSDIA VEWESNGQPE NNYKTTPPVL  660
DSDGSFFLYS RLTVDKSRWQ EGNVFSCSVM HEALHNHYTQ KSLSLSLGK              709

SEQ ID NO: 92          moltype = AA  length = 340
FEATURE                Location/Qualifiers
source                 1..340
                       mol_type = protein
                       organism = synthetic construct
SEQUENCE: 92
EVQLVESGGG LVQPGGSLRL SCAASGLTFS DYSMSWYRQA PGKGRELVAI ISGSGVITHY  60
VDSVKGRFTI SRDNAKNTLY LQMRSLRAED TAVYYCRAVS DWEDYWGQGT QVTVSSGGGG  120
SGGGGSDIQM TQSPSSLSAS VGDRVTITCR ASENIYSYLA WYQQKPGKSP KLLIYNARTL  180
AEGVPSRFSG SGSGTDFTLT ISSLQPEDFA TYYCQYHSGS PLPFGGGTKV EIKRTVAAPS  240
VFIFPPSDEQ LKSGTASVVC LLNNFYPREA KVQWKVDNAL QSGNSQESVT EQDSKDSTYS  300
LSSTLTLSKA DYEKHKVYAC EVTHQGLSSP VTKSFNRGEC                        340

SEQ ID NO: 93          moltype = AA  length = 709
FEATURE                Location/Qualifiers
source                 1..709
                       mol_type = protein
                       organism = synthetic construct
SEQUENCE: 93
HVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSSGGG GSGGGGSEVQ LVQSGAEVKK PGASVKVSCK ASGYTFTNYW MHWVRQAPGQ  180
GLEWMGRIDP DSTGSKYNEK FKTRVTMTRD TSTSTVYMEL SSLRSEDTAV YYCAREGAYG  240
YYFDYWGQGT LVTVSSASTK GPSVFPLAPC SRSTSESTAA LGCLVKDYFP EPVTVSWNSG  300
ALTSGVHTFP AVLQSSGLYS LSSVVTVPSS SLGTKTYTCN VDHKPSNTKV DKRVESKYGP  360
PCPPCPAPEF LGGPSVFLFP PKPKDTLMIS RTPEVTCVVV DVSQEDPEVQ FNWYVDGVEV  420
HNAKTKPREE QFNSTYRVVS VLTVLHQDWL NGKEYKCKVS NKGLPSSIEK TISKAKGQPR  480
EPQVYTLPPS QEEMTKNQVS LTCLVKGFYP SDIAVEWESN GQPENNYKTT PPVLDSDGSF  540
FLYSRLTVDK SRWQEGNVFS CSVMHEALHN HYTQKSLSLS LGKGGGGSGG GGSEVQLVES  600
GGGLVQPGGS LRLSCAASGL TFSDYSMSWY RQAPGKGREL VAIISGSGVI THYVDSVKGR  660
FTISRDNAKN TLYLQMRSLR AEDTAVYYCR AVSDWEDYWG QGTQVTVSS              709

SEQ ID NO: 94          moltype = AA  length = 340
FEATURE                Location/Qualifiers
source                 1..340
                       mol_type = protein
                       organism = synthetic construct
SEQUENCE: 94
DIQMTQSPSS LSASVGDRVT ITCRASENIY SYLAWYQQKP GKSPKLLIYN ARTLAEGVPS  60
RFSGSGSGTD FTLTISSLQP EDFATYYCQY HSGSPLPFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSEVQLVE SGGGLVQPGG  240
SLRLSCAASG LTFSDYSMSW YRQAPGKGRE LVAIISGSGV ITHYVDSVKG RFTISRDNAK  300
NTLYLQMRSL RAEDTAVYYC RAVSDWEDYW GQGTQVTVSS                        340

SEQ ID NO: 95          moltype = AA  length = 127
```

```
FEATURE                Location/Qualifiers
source                 1..127
                       mol_type = protein
                       organism = synthetic construct
SEQUENCE: 95
EVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSS                                                            127

SEQ ID NO: 96          moltype = AA  length = 127
FEATURE                Location/Qualifiers
source                 1..127
                       mol_type = protein
                       organism = synthetic construct
SEQUENCE: 96
QVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSS                                                            127

SEQ ID NO: 97          moltype = AA  length = 709
FEATURE                Location/Qualifiers
source                 1..709
                       mol_type = protein
                       organism = synthetic construct
SEQUENCE: 97
EVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSSGGG GSGGGGSEVQ LVQSGAEVKK PGASVKVSCK ASGYTFTNYW MHWVRQAPGQ  180
GLEWMGRIDP DSTGSKYNEK FKTRVTMTRD TSTSTVYMEL SSLRSEDTAV YYCAREGAYG  240
YYFDYWGQGT LVTVSSASTK GPSVFPLAPC SRSTSESTAA LGCLVKDYFP EPVTVSWNSG  300
ALTSGVHTFP AVLQSSGLYS LSSVVTVPSS SLGTKTYTCN VDHKPSNTKV DKRVESKYGP  360
PCPPCPAPEF LGGPSVFLFP PKPKDTLMIS RTPEVTCVVV DVSQEDPEVQ FNWYVDGVEV  420
HNAKTKPREE QFNSTYRVVS VLTVLHQDWL NGKEYKCKVS NKGLPSSIEK TISKAKGQPR  480
EPQVYTLPPS QEEMTKNQVS LTCLVKGFYP SDIAVEWESN GQPENNYKTT PPVLDSDGSF  540
FLYSRLTVDK SRWQEGNVFS CSVMHEALHN HYTQKSLSLS LGKGGGGSGG GGSEVQLVES  600
GGGLVQPGGS LRLSCAASGL TFSDYSMSWY RQAPGKGREL VAIISGSGVI THYVDSVKGR  660
FTISRDNAKN TLYLQMRSLR AEDTAVYYCR AVSDWEDYWG QGTQVTVSS              709

SEQ ID NO: 98          moltype = AA  length = 709
FEATURE                Location/Qualifiers
source                 1..709
                       mol_type = protein
                       organism = synthetic construct
SEQUENCE: 98
QVQLVESGGG LVQPGGSLRL SCVASASGFT YRPYCMAWFR QAPGKEREAV AGIDIFGGTT  60
YADSVKGRFT ASRDNAGFSL YLQMNSLRAE DTAVYYCAAG DSPDGRCPPL GQGLNYWGQG  120
TMVTVSSGGG GSGGGGSEVQ LVQSGAEVKK PGASVKVSCK ASGYTFTNYW MHWVRQAPGQ  180
GLEWMGRIDP DSTGSKYNEK FKTRVTMTRD TSTSTVYMEL SSLRSEDTAV YYCAREGAYG  240
YYFDYWGQGT LVTVSSASTK GPSVFPLAPC SRSTSESTAA LGCLVKDYFP EPVTVSWNSG  300
ALTSGVHTFP AVLQSSGLYS LSSVVTVPSS SLGTKTYTCN VDHKPSNTKV DKRVESKYGP  360
PCPPCPAPEF LGGPSVFLFP PKPKDTLMIS RTPEVTCVVV DVSQEDPEVQ FNWYVDGVEV  420
HNAKTKPREE QFNSTYRVVS VLTVLHQDWL NGKEYKCKVS NKGLPSSIEK TISKAKGQPR  480
EPQVYTLPPS QEEMTKNQVS LTCLVKGFYP SDIAVEWESN GQPENNYKTT PPVLDSDGSF  540
FLYSRLTVDK SRWQEGNVFS CSVMHEALHN HYTQKSLSLS LGKGGGGSGG GGSEVQLVES  600
GGGLVQPGGS LRLSCAASGL TFSDYSMSWY RQAPGKGREL VAIISGSGVI THYVDSVKGR  660
FTISRDNAKN TLYLQMRSLR AEDTAVYYCR AVSDWEDYWG QGTQVTVSS              709

SEQ ID NO: 99          moltype = AA  length = 12
FEATURE                Location/Qualifiers
source                 1..12
                       mol_type = protein
                       organism = synthetic construct
SEQUENCE: 99
GWTFGGQCSP AD                                                      12

SEQ ID NO: 100         moltype = AA  length = 10
FEATURE                Location/Qualifiers
source                 1..10
                       mol_type = protein
                       organism = synthetic construct
SEQUENCE: 100
GGGGSGGGGS                                                         10

SEQ ID NO: 101         moltype = AA  length = 17
FEATURE                Location/Qualifiers
source                 1..17
                       mol_type = protein
                       organism = synthetic construct
```

-continued

```
SEQUENCE: 101
IISGSGGITH YVDSVKG                                                17
```